(12) United States Patent
Kim et al.

(10) Patent No.: US 12,331,086 B2
(45) Date of Patent: Jun. 17, 2025

(54) ARTIFICIALLY ENGINEERED SC FUNCTION CONTROL SYSTEM

(71) Applicant: TOOLGEN INCORPORATED, Seoul (KR)

(72) Inventors: Seok Joong Kim, Seoul (KR); Dong Woo Song, Seoul (KR); Young Bin Hong, Seoul (KR); Byung Ok Choi, Seoul (KR); Jae Young Lee, Seoul (KR); Jung Min Lee, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 1394 days.

(21) Appl. No.: 16/349,672

(22) PCT Filed: Sep. 28, 2017

(86) PCT No.: PCT/KR2017/010897
§ 371 (c)(1),
(2) Date: May 14, 2019

(87) PCT Pub. No.: WO2018/088694
PCT Pub. Date: May 17, 2018

(65) Prior Publication Data
US 2019/0276503 A1    Sep. 12, 2019

Related U.S. Application Data

(60) Provisional application No. 62/421,516, filed on Nov. 14, 2016.

(51) Int. Cl.
| | | |
|---|---|---|
| *C12N 15/113* | (2010.01) | |
| *A61K 35/30* | (2015.01) | |
| *C07K 14/315* | (2006.01) | |
| *C12N 15/86* | (2006.01) | |

(52) U.S. Cl.
CPC ............ *C07K 14/315* (2013.01); *A61K 35/30* (2013.01); *C12N 15/113* (2013.01); *C12N 15/86* (2013.01); *C12N 2310/10* (2013.01); *C12N 2310/20* (2017.05)

(58) Field of Classification Search
CPC .................................................. C12N 15/113
See application file for complete search history.

(56) References Cited

U.S. PATENT DOCUMENTS

2015/0284727 A1   10/2015   Kim et al.
2016/0237455 A1   8/2016   Glucksmann et al.

FOREIGN PATENT DOCUMENTS

| CN | 105164264 A | 12/2015 |
|---|---|---|
| KR | 10-2016-0044457 A | 4/2016 |
| KR | 10-2016-0102056 A | 8/2016 |
| KR | 10-1656237 B1 | 9/2016 |
| WO | WO-2008-154644 A1 | 12/2008 |
| WO | WO-2015/048577 A2 | 4/2015 |
| WO | WO-2015/188056 A1 | 12/2015 |
| WO | WO-2016/021973 A1 | 2/2016 |
| WO | WO-2017/070633 A2 | 4/2017 |

OTHER PUBLICATIONS

Miller, Jeffrey, 2015, US 20150353917 A1.*
Zhang et al., 2014, Geneseq Accession No. BBS43273, computer printout, pp. 1-3.*
Saberan-Djoneidi et al., 2000, GenEmbl Accession No. AF059314, computer printout, p. 1-2.*
Joung et al., 2014, Geneseq Accession No. BBN11743, computer printout, pp. 1-2.*
Charpentier et al., 2013, Geneseq Accession No. BAZ50216, computer printout, pp. 1-2.*
Sutter et al., 1995, GenEmbl Accession No. U08049, computer printout, pp. 1-2.*
Doench, et al: "Optimized sgRNA design to maximize activity and minimize off-target effects of CRISPR-Cas9.", *Nature Biotechnology*, vol. 34, No. 2, Jan. 18, 2016, pp. 184-191, XP55551151.
Pantera, et al: "A Genome Editing Approach to Studying Pmp22 Enhancer Functionality.", *The FASEB Journal*, Apr. 1, 2016, p. 584.2, XP55682926.
Lee, et al: "Targeted PMP22 TATA-box editing by CRISPR/Cas9 reduces demyelinating neuropathy of Charcot-Marie-Tooth disease type 1A in mice.", *Nucleic Acids Research*, vol. 48, Issue 1, Jan. 10, 2020, pp. 130-140, https://doi.org/10.1093/nar/gkz1070.
Van Paassen, et al: "PMP22 related neuropathies: Charcot-Marie-Tooth disease type 1A and Hereditary Neuropathy with liability to Pressure Palsies.", *Orphanet Journal of Rare Diseases*, 9:38, pp. 1-15, XPO21181110.
Arnold, et al: "The genetics of Charcot-Marie-Tooth disease: current trends and future implications for diagnosis and management.", *The Applications of Clinical Genetics*, 2015, 8:235-243. XP55682896.
Partial Supplementary European Search Report, dated May 26, 2020, issued for corresponding European Patent Application No. EP 17869218.2.

(Continued)

*Primary Examiner* — Anoop K Singh
*Assistant Examiner* — David A Montanari
(74) *Attorney, Agent, or Firm* — Harness, Dickey & Pierce, P.L.C.

(57) ABSTRACT

The present invention relates to an artificially manipulated SC function-controlling factor for SC function control and/or the treatment or alleviation of a disease due to an SC function disorder, and to a use thereof. More specifically, the present invention relates to a system capable of performing artificial SC function control and/or treating or alleviating a disease due to an SC function disorder, the system comprising: an artificially manipulated SC function-controlling factor for SC function control and/or the treatment or alleviation of a disease due to an SC function disorder; and/or a composition for treating or alleviating a disease due to an SC function disorder. In a specific aspect, the present invention relates to an SC function-controlling system by an SC function-controlling factor, such as artificially manipulated PMP22, and/or an expression product thereof.

5 Claims, 30 Drawing Sheets

Specification includes a Sequence Listing.

(56) References Cited

OTHER PUBLICATIONS

Liu, et al: "Knockdown of Peripheral Myelin Protein 22 Inhibits the Progression of Chronic Myeloid Leukemia." *Oncology Research*, 22:259-265, XP55682944.

Doench, et al: "Supplementary information to Optimized sgRNA design to maximize activity and minimize off-target effects of CRISPR-Cas9—Table 21, excerpt", XP55683076.

Doench, et al: "Supplementary information to Optimized sgRNA design to maximize activity and minimize off-target effects of CRISPR-Cas9—Table 22, excerpt", XP55683080.

Morales, et al: "Rewiring Integrin-Mediated Signaling and Cellular Response with the Peripheral Myelin Protein 22 and Epithelial Membrane Protein 2 Components of the Tetraspan Web", *IOVS*, Jul. 2011, vol. 52. No. 8, XP55683101.

Li, J., et al.; "*The PMP22* Gene and Its Related Diseases", Mol Neurobiol (2013) 47:673-698.

Hai, M., et al.; "Identification of a positive regulatory element in the myelin-specific promoter of the PMP22 gene", Journal of Neuroscience Research 65:508-519 (2001).

International Search Report from corresponding PCT Application No. PCT/KR2017/010897, dated Jan. 29, 2018.

Written Opinion of the International Searching Authority from corresponding PCT Application No. PCT/KR2017/010897, dated Jan. 29, 2018.

Search Report and Written Opinion from corresponding Singapore Patent Application No. 11201904241W, dated Jul. 2, 2020.

Office Action from corresponding Korean Patent Application No. 10-2017-0126636, issued Jul. 20, 2020.

Kim, H., et al.; "A simple, flexible and high-throughput cloning system for plant genome editing via CRISPR-Cas system", Journal of Integrative Plant Biology, vol. 58, pp. 702-712, 2016.

Office Action from corresponding Japanese Patent Application No. 2019-524226, issued Nov. 9, 2021.

Office Action from corresponding Russian Patent Application No. 2019118283, issued Apr. 26, 2021.

Avdeeva, Z.I et al., The safety of medicines of monoclonal antibodies connected with manifestation of their immunogenicity, Immunology, No. 4, 2015, p. 247-256 (see p. 248) [in Russian].

Avdeeva, Z.I. et al., Requirements for production and control of medicines based on monoclonal antibodies used for treatment, Biopreparations, 2010, pp. 11-14 (see p. 13) [in Russian].

Notice of Allowance from corresponding Russian Patent Application No. 2019118283, issued Dec. 7, 2021.

Suter U., et al.; "Regulation of Tissue-specific Expression of Alternative Peripheral Myelin Protein-22 (P M. 2 2) Gene Transcripts by Two Promoters", J. Biol. Chem., vol. 269, No. 41, Oct. 14, 1994 (Oct. 14, 1994), pp. 25795-25808.

Extended European Search Report from corresponding European Patent Application No. 21166447.9, issued Sep. 22, 2021.

Shijie Huaren Xiaohua Zashi, 2015, vol. 23, p. 3742-3748.

Mehreen Hai et al: Competitive Binding of Triplex-Forming Oligonucleotides in the Two Alternate Promoters of the PMP22 Gene11? Antisense & Nucleic Acid Drug Development., vol. 11, No. 4, Aug. 2001 (Aug. 2001) pp. 233-246, P055643869, US ISSN: 1087-2906, DOI: 10.1089/108729001317022232 p. 245 left-hand column.

Office Action from corresponding Japanese Patent Application No. 2019-524226, dated Jul. 5, 2022.

Journal of Integrative Plant Biology, Aug. 2016, vol. 58, p. 705-712.

Office Action from corresponding Chinese Patent Application No. 201780083263.5, dated Sep. 28, 2022.

\* cited by examiner

| sgRNAs | Direction | Mismatch 0 | Mismatch 1 | Mismatch 2 | Indel ratio(%) |
|---|---|---|---|---|---|
| sgRNA_CDS_Sp#1 | - | 1 | 0 | 0 | 76.80 |
| sgRNA_CDS_Sp#2 | - | 1 | 0 | 0 | 21.20 |
| sgRNA_CDS_Sp#3 | + | 1 | 0 | 0 | 66.30 |
| sgRNA_CDS_Sp#4 | - | 1 | 0 | 0 | 65.90 |
| sgRNA_CDS_Sp#5 | - | 1 | 0 | 0 | 66.50 |
| sgRNA_CDS_Sp#6 | + | 1 | 0 | 0 | 43.10 |
| sgRNA_CDS_Sp#7 | - | 1 | 0 | 0 | 75.00 |
| sgRNA_CDS_Sp#8 | + | 1 | 0 | 0 | 19.90 |

FIG. 1A

| sgRNAs | Direction | Mismatch 0 | Mismatch 1 | Mismatch 2 | Indel ratio(%) |
|---|---|---|---|---|---|
| sgRNA_TATA_Sp#1 | - | 1 | 0 | 1 | 32.80 |
| sgRNA_TATA_Sp#2 | + | 1 | 0 | 0 | 42.00 |
| sgRNA_TATA_Sp#3 | + | 1 | 0 | 0 | 25.20 |
| sgRNA_TATA_Sp#4 | + | 1 | 0 | 2 | 59.10 |
| sgRNA_TATA_Sp#5 | + | 1 | 0 | 0 | 16.20 |
| sgRNA_TATA_Sp#6 | + | 1 | 0 | 1 | 30.30 |
| sgRNA_TATA_Sp#7 | - | 1 | 0 | 1 | 53.80 |
| sgRNA_TATA_Sp#8 | + | 1 | 0 | 0 | 7.30 |
| sgRNA_TATA_Sp#9 | - | 1 | 0 | 1 | 26.90 |
| sgRNA_TATA_Sp#10 | - | 1 | 0 | 1 | 15.90 |
| sgRNA_TATA_Sp#11 | - | 1 | 0 | 2 | 24.20 |
| sgRNA_TATA_Sp#12 | - | 1 | 0 | 2 | 38.20 |
| sgRNA_TATA_Sp#13 | - | 1 | 0 | 0 | 6.90 |
| sgRNA_TATA_Sp#14 | + | 1 | 0 | 1 | 62.00 |
| sgRNA_TATA_Sp#15 | + | 1 | 0 | 1 | 54.60 |
| sgRNA_TATA_Sp#16 | - | 1 | 0 | 1 | 32.50 |

FIG. 1B

| sgRNAs | Direction | Mismatch 0 | Mismatch 1 | Mismatch 2 | Indel ratio(%) |
|---|---|---|---|---|---|
| sgRNA_Enh_Sp#1 | - | 1 | 0 | 1 | 66.30 |
| sgRNA_Enh_Sp#2 | + | 1 | 0 | 0 | 18.80 |
| sgRNA_Enh_Sp#3 | - | 1 | 0 | 1 | 24.40 |
| sgRNA_Enh_Sp#4 | + | 1 | 0 | 0 | 44.00 |
| sgRNA_Enh_Sp#5 | - | 1 | 0 | 2 | 41.30 |
| sgRNA_Enh_Sp#6 | + | 1 | 0 | 1 | 8.60 |
| sgRNA_Enh_Sp#10 | - | 1 | 0 | 2 | 19.30 |
| sgRNA_Enh_Sp#11 | - | 1 | 0 | 2 | 21.90 |
| sgRNA_Enh_Sp#12 | - | 1 | 0 | 2 | 2.50 |
| sgRNA_Enh_Sp#13 | - | 1 | 0 | 1 | 12.80 |
| sgRNA_Enh_Sp#14 | - | 1 | 0 | 1 | 11.40 |
| sgRNA_Enh_Sp#15 | + | 1 | 0 | 1 | 21.80 |
| sgRNA_Enh_Sp#16 | + | 1 | 0 | 1 | 47.40 |

FIG. 1C

| sgRNAs | Direction | Mismatch 0 | Mismatch 1 | Mismatch 2 | Indel ratio(%) |
|---|---|---|---|---|---|
| sgRNA_CDS_Cj#1 | - | 1 | 0 | 0 | 12.90 |
| sgRNA_CDS_Cj#2 | + | 1 | 0 | 0 | 3.90 |
| sgRNA_CDS_Cj#3 | + | 1 | 0 | 0 | 0.10 |
| sgRNA_CDS_Cj#4 | + | 1 | 0 | 0 | 2.80 |
| sgRNA_CDS_Cj#5 | - | 1 | 0 | 0 | 0.70 |

FIG. 2A

| sgRNAs | Direction | Mismatch 0 | Mismatch 1 | Mismatch 2 | Indel ratio(%) |
|---|---|---|---|---|---|
| sgRNA_TATA_Cj#1 | + | 1 | 0 | 0 | 0.35 |
| sgRNA_TATA_Cj#2 | + | 1 | 0 | 0 | 0.07 |
| sgRNA_TATA_Cj#3 | + | 1 | 0 | 0 | 0.04 |
| sgRNA_TATA_Cj#4 | + | 1 | 0 | 1 | 3.80 |
| sgRNA_TATA_Cj#5 | + | 1 | 0 | 0 | 36.10 |
| sgRNA_TATA_Cj#6 | - | 1 | 0 | 0 | 0.02 |
| sgRNA_TATA_Cj#7 | + | 1 | 0 | 0 | 0.02 |
| sgRNA_TATA_Cj#8 | - | 1 | 0 | 0 | 0.06 |
| sgRNA_TATA_Cj#9 | - | 1 | 0 | 0 | 0.15 |
| sgRNA_TATA_Cj#10 | - | 1 | 0 | 0 | 13.10 |
| sgRNA_TATA_Cj#11 | - | 1 | 0 | 0 | 0.12 |

FIG. 2B

| sgRNAs | Direction | Mismatch 0 | Mismatch 1 | Mismatch 2 | Indel ratio(%) |
|---|---|---|---|---|---|
| sgRNA_Enh_Cj#1 | + | 1 | 0 | 0 | 16.70 |
| sgRNA_Enh_Cj#2 | + | 1 | 0 | 0 | 0.07 |
| sgRNA_Enh_Cj#3 | - | 1 | 0 | 0 | 0 |
| sgRNA_Enh_Cj#4 | + | 1 | 0 | 0 | 1.18 |
| sgRNA_Enh_Cj#5 | - | 1 | 0 | 0 | 0.03 |
| sgRNA_Enh_Cj#6 | - | 1 | 0 | 0 | 0.05 |
| sgRNA_Enh_Cj#7 | - | 1 | 0 | 0 | 0.09 |
| sgRNA_Enh_Cj#8 | + | 1 | 0 | 0 | 0.28 |
| sgRNA_Enh_Cj#9 | - | 1 | 0 | 0 | 41.40 |
| sgRNA_Enh_Cj#10 | + | 1 | 0 | 0 | 0.45 |
| sgRNA_Enh_Cj#11 | - | 1 | 0 | 0 | 0.55 |
| sgRNA_Enh_Cj#12 | + | 1 | 0 | 0 | 2.83 |
| sgRNA_Enh_Cj#13 | + | 1 | 0 | 0 | 0.03 |

FIG. 2C

| Name | sgRNAs | More than minimum frequency | Insertions | Deletions | Indel ratio(%) |
|---|---|---|---|---|---|
| TATA WT | | 26730 | 28 | 70 | 0.40 |
| TATA-1 | sgRNA_TATA_Sp#15 | 30466 | 3110 | 6357 | 31.10 |
| TATA-2 | sgRNA_TATA_Sp#12 | 9286 | 0 | 6929 | 74.60 |
| | sgRNA_TATA_Sp#14 | 5651 | 118 | 4972 | 90.10 |
| Enh WT | | 27917 | 0 | 11 | 0.00 |
| Enh-3 | sgRNA_Enh_Sp#1 | 32148 | 8744 | 10126 | 58.70 |
| Enh-4 | sgRNA_Enh_Sp#5 | 37486 | 23 | 30928 | 82.60 |
| | sgRNA_Enh_Sp#16 | 37277 | 69 | 35000 | 94.10 |
| Enh-5 | sgRNA_Enh_Sp#1 | 30576 | 2782 | 14544 | 56.70 |
| | sgRNA_Enh_Sp#4 | 30399 | 217 | 11894 | 39.80 |
| CDS-SP1 WT | | 35424 | 0 | 40 | 0.10 |
| CDS-SP1 | sgRNA_CDS_Sp#1 | 32206 | 4613 | 9077 | 42.50 |
| CDS-SP3 WT | | 21997 | 0 | 0 | 0.00 |
| CDS-SP3 | sgRNA_CDS_Sp#3 | 27511 | 3441 | 11877 | 55.70 |

FIG. 3

| sgRNAs | CDS-SP1 | | CDS-SP3 | |
|---|---|---|---|---|
| | Reads | Ratio | Reads | Ratio |
| Total indels | 13690 | 1 | 15312 | 1 |
| 3N±1, 3N±2 | 10063 | 0.74 | 12795 | 0.84 |
| 3N±0 | 3627 | 0.26 | 2517 | 0.16 |

FIG. 4

| Indel | Local Sequence | Frequency (%) |
|---|---|---|
| WT | ACTGAAGCCAGACCAGGCGTCTTTCCAGTTATTCAGGGGCTGGTCCAATGCTGGGATATGTCATGGTGGCCTGAGAGGTTCTCAGCCTC | |
| -1 | ACTGAAGCCAGACCAGGCGTCTTTCCAG-TTATTCAGGGGCTGGTCCAATGCTGGGATATGTCATGGTGGCCTGAGAGGTTCTCAGCCTC | 14.00 |
| -2 | ACTGAAGCCAGACCAGGCGTCTCTTTCCAGTT--TTCAGGGGCTGGTCCAATGCTGGGATATGTCATGGTGGCCTGAGAGGTTCTCAGCCTC | 8.86 |
| +1 | ACTGAAGCCAGACCAGGCGTCTTTCCAGTTTATTCAGGGGCTGGTCCAATGCTGGGATATGTCATGGCGGCCTGAGAGGTTCTCAGCCTC | 3.84 |
| -3 | ACTGAAGCCAGACCAGGCGTCTTTCCAGT---TTCAGGGGCTGGTCCAATGCTGGGATATGTCATGGCGGGCTGAGAGGTTCTCAGCCTC | 3.53 |
| -4 | ACTGAAGCCAGACCAGGCGTCTTTCCAG----TTCAGGGGCTGGTCCAATGCTGGGATATGTCATGGGGGCCTGAGAGGTTCTCAGCCTC | 2.81 |

FIG. 9B

| | Location | Position | Target sequence (5' to 3') | Gene |
|---|---|---|---|---|
| On-target | chr17 | 15265347 | GGACCAGCCCTGAATAAACTGG | hPMP22-TATA |
| Off1 | chr5 | 135488419 | GGACCAGCCaCaGAATAAACCAG | Intergenic |
| Off2 | chr8 | 140735957 | tGACCAGtCCaTGAATAAACCAG | PTK2 (Intron) |
| Off3 | chr12 | 14124312 | GGACCAGaCaCTGAATAAtACCAG | Intergenic |
| Off4 | chr4 | 97775621 | GGACCAGCCaCaGAATAAATAAG | STPG2 (Intron) |
| Off5 | chr5 | 26531145 | GGAtCAGCCCCaGAATAAACCAG | Intergenic |
| Off6 | chr1 | 41780482 | GGACATCCCCaGAATAAACCAG | HIVEP3 (Intron) |
| Off7 | chr1 | 157564675 | GGAtCAGCgtCTGAATAAACCAG | Intergenic |
| Off8 | chr13 | 20254256 | aGACCAGCCCCaGAAcAAACCAG | Intergenic |
| Off9 | chr15 | 100401183 | GtACgAGCCCTGAATAAAtAGG | CERS3 (Exon) |
| Off10 | chr6 | 26006396 | GGACCAaaCaCTGAATAACCAG | Intergenic |
| Off11 | chr20 | 10136908 | GcACCAGCCaCTGAATtAACCAG | SNAP25 (Intron) |
| Off12 | chrX | 7525146 | GtACCAGtCCaCTGAAaAAACCAG | Intergenic |
| Off13 | chr18 | 1972251 | GaACCAGCCCCTGAttAgACCAG | Intergenic |
| Off14 | chr18 | 77536261 | GtACCAGCCaCTGAAaAAACAGG | Intergenic |
| Off15 | chr11 | 30065750 | GtACCAGCCCTGCAaAAACCAG | Intergenic |
| Off16 | chr11 | 30579429 | GcACCAGgCCTGAATAAACCAG | MPP2D2 (Intron) |
| Off17 | chr11 | 35726323 | GGcCCAGCCaCTGAgTAAACTAG | TRIM44 (Intron) |
| Off18 | chr11 | 112468286 | GGAattGCCCTGAATAAACAAG | RP11-65M17.3 (Intron) |

FIG. 9C

| | Location | Position | Target sequence (5' to 3') | Gene |
|---|---|---|---|---|
| On-target | chr17 | 15265347 | GGACCAGCCCCTGAATAAAC*TGG* | hPMP22-TATA |
| Off1 | chr5 | 384420810 | GGgaacagCCCTGAATAAAC*CTG* | EGFLAM (Intron) |
| Off2 | chr7 | 28618099 | aGgaCCagCtCTGAATAAAC*TGG* | CREB5 (Intron) |
| Off3 | chr5 | 384420811 | GGAaCAGCCCtgaATAAAC*CAGG* | EGFLAM (Intron) |
| Off4 | chr10 | 93462291 | GagttcAGCCCTGAATAACA*GG* | Intergenic |
| Off5 | chr3 | 78627344 | GGgaCcagCCCCAGAATAAa*GGG* | Intergenic |
| Off6 | chr2 | 131586033 | aagCCAaCCCCTGAATAAAC*AGG* | Intergenic |
| Off7 | chr18 | 56254369 | cacaCAGCCCCTcAATAAAC*TGG* | ALPK2 (Intron) |
| Off8 | chr22 | 274477459 | GaggCAGCCCCTGtATAAAC*TGG* | Intergenic |
| Off9 | chr6 | 915B6787 | GacCagccCCCTGAATAAca*TGG* | Intergenic |

FIG. 10B

| | Location | Position | Target sequence (5' to 3') | Gene |
|---|---|---|---|---|
| On-target | chr17 | 15265347 | GGACCAGCCCCTGAATAAACTGG | hPMP22-TATA |
| Off1 | chr12 | 118558427 | GtACCAGCCCTGAcaAAACAGG | Intergenic |
| Off2 | chr1 | 74579514 | GGAgCAGCCCCgGAATgAACAGG | Zfp142 (Exon) |
| Off3 | chr13 | 50187695 | GGACCAGCCCCTGtATAccCTGG | Intergenic |
| Off4 | chr13 | 50319559 | GGACCAGCCCCTGtATAccCTGG | Intergenic |
| Off5 | chr13 | 50623450 | GGACCAGCCCCTGtATAccCTGG | Intergenic |
| Off6 | chr2 | 29191358 | GGcCCtGCCCTaAATAAACAGG | Intergenic |
| Off7 | chr9 | 102823783 | GGAtCAGCCCCaGAATAAAcCTGG | Intergenic |
| Off8 | chrX | 101405421 | GGACtAGCCCCTGAgTAcACTGG | Zmym3 (Exon) |

SEQUENCE LISTING

```
<160> NUMBER OF SEQ ID NOS: 252

<210> SEQ ID NO 1
<211> LENGTH: 20
<212> TYPE: DNA
<213> ORGANISM: Homo sapiens

<400> SEQUENCE: 1
cgatgatact cagcaacagg                                                    20

<210> SEQ ID NO 2
<211> LENGTH: 20
<212> TYPE: DNA
<213> ORGANISM: Homo sapiens

<400> SEQUENCE: 2
ggacgatgat actcagcaac                                                    20

<210> SEQ ID NO 3
<211> LENGTH: 20
<212> TYPE: DNA
```

```
<213> ORGANISM: Homo sapiens

<400> SEQUENCE: 3
atggacacgc aactgatctc                                               20

<210> SEQ ID NO 4
<211> LENGTH: 20
<212> TYPE: DNA
<213> ORGANISM: Homo sapiens

<400> SEQUENCE: 4
gatgatcgac aggatcatgg                                               20

<210> SEQ ID NO 5
<211> LENGTH: 20
<212> TYPE: DNA
<213> ORGANISM: Homo sapiens

<400> SEQUENCE: 5
gaagatgatc gacaggatca                                               20

<210> SEQ ID NO 6
<211> LENGTH: 20
<212> TYPE: DNA
<213> ORGANISM: Homo sapiens

<400> SEQUENCE: 6
aactcttcac cctcaccaag                                               20

<210> SEQ ID NO 7
<211> LENGTH: 20
<212> TYPE: DNA
<213> ORGANISM: Homo sapiens

<400> SEQUENCE: 7
aaaacctgcc ccccttggtg                                               20

<210> SEQ ID NO 8
<211> LENGTH: 20
<212> TYPE: DNA
<213> ORGANISM: Homo sapiens

<400> SEQUENCE: 8
ggaatcttcc aaattcttgc                                               20

<210> SEQ ID NO 9
<211> LENGTH: 22
<212> TYPE: DNA
<213> ORGANISM: Homo sapiens

<400> SEQUENCE: 9
gatcgtggag acgaacagca gc                                            22

<210> SEQ ID NO 10
<211> LENGTH: 22
<212> TYPE: DNA
<213> ORGANISM: Homo sapiens

<400> SEQUENCE: 10
gctgacgatc gtggagacga ac                                            22

<210> SEQ ID NO 11
<211> LENGTH: 22
```

-continued

```
<212> TYPE: DNA
<213> ORGANISM: Homo sapiens

<400> SEQUENCE: 11
cgcaactgat ctctggcaga ac                                              22

<210> SEQ ID NO 12
<211> LENGTH: 22
<212> TYPE: DNA
<213> ORGANISM: Homo sapiens

<400> SEQUENCE: 12
gtgcgtgatg agtgctgcgg cc                                              22

<210> SEQ ID NO 13
<211> LENGTH: 22
<212> TYPE: DNA
<213> ORGANISM: Homo sapiens

<400> SEQUENCE: 13
gtgtagatgg ccgcagcact ca                                              22

<210> SEQ ID NO 14
<211> LENGTH: 20
<212> TYPE: DNA
<213> ORGANISM: Homo sapiens

<400> SEQUENCE: 14
ggaccagccc ctgaataaac                                                 20

<210> SEQ ID NO 15
<211> LENGTH: 20
<212> TYPE: DNA
<213> ORGANISM: Homo sapiens

<400> SEQUENCE: 15
ggcgtctttc cagtttattc                                                 20

<210> SEQ ID NO 16
<211> LENGTH: 20
<212> TYPE: DNA
<213> ORGANISM: Homo sapiens

<400> SEQUENCE: 16
gcgtctttcc agtttattca                                                 20

<210> SEQ ID NO 17
<211> LENGTH: 20
<212> TYPE: DNA
<213> ORGANISM: Homo sapiens

<400> SEQUENCE: 17
cgtctttcca gtttattcag                                                 20

<210> SEQ ID NO 18
<211> LENGTH: 20
<212> TYPE: DNA
<213> ORGANISM: Homo sapiens

<400> SEQUENCE: 18 ttcagggct ggtccaatgc                                                  20

<210> SEQ ID NO 19
```

```
<211> LENGTH: 20
<212> TYPE: DNA
<213> ORGANISM: Homo sapiens

<400> SEQUENCE: 19
tcaggggctg gtccaatgct                                              20

<210> SEQ ID NO 20
<211> LENGTH: 20
<212> TYPE: DNA
<213> ORGANISM: Homo sapiens

<400> SEQUENCE: 20
accatgacat atcccagcat                                              20

<210> SEQ ID NO 21
<211> LENGTH: 20
<212> TYPE: DNA
<213> ORGANISM: Homo sapiens

<400> SEQUENCE: 21
tttccagttt attcaggggc                                              20

<210> SEQ ID NO 22
<211> LENGTH: 20
<212> TYPE: DNA
<213> ORGANISM: Homo sapiens

<400> SEQUENCE: 22
cagttacagg gagcaccacc                                              20

<210> SEQ ID NO 23
<211> LENGTH: 20
<212> TYPE: DNA
<213> ORGANISM: Homo sapiens

<400> SEQUENCE: 23
ctggtctggc ttcagttaca                                              20

<210> SEQ ID NO 24
<211> LENGTH: 20
<212> TYPE: DNA
<213> ORGANISM: Homo sapiens

<400> SEQUENCE: 24
cctggtctgg cttcagttac                                              20

<210> SEQ ID NO 25
<211> LENGTH: 20
<212> TYPE: DNA
<213> ORGANISM: Homo sapiens

<400> SEQUENCE: 25
aactggaaag acgcctggtc                                              20

<210> SEQ ID NO 26
<211> LENGTH: 20
<212> TYPE: DNA
<213> ORGANISM: Homo sapiens

<400> SEQUENCE: 26
gaataaactg gaaagacgcc                                              20
```

```
<210> SEQ ID NO 27
<211> LENGTH: 20
<212> TYPE: DNA
<213> ORGANISM: Homo sapiens

<400> SEQUENCE: 27
tccaatgctg ggatatgtca                                             20

<210> SEQ ID NO 28
<211> LENGTH: 20
<212> TYPE: DNA
<213> ORGANISM: Homo sapiens

<400> SEQUENCE: 28
aatgctggga tatgtcatgg                                             20

<210> SEQ ID NO 29
<211> LENGTH: 20
<212> TYPE: DNA
<213> ORGANISM: Homo sapiens

<400> SEQUENCE: 29
atagaggctg agaacctctc                                             20

<210> SEQ ID NO 30
<211> LENGTH: 22
<212> TYPE: DNA
<213> ORGANISM: Homo sapiens

<400> SEQUENCE: 30
gccctctgaa tctccagtca at                                          22

<210> SEQ ID NO 31
<211> LENGTH: 22
<212> TYPE: DNA
<213> ORGANISM: Homo sapiens

<400> SEQUENCE: 31
aatctccagt caattccaac ac                                          22

<210> SEQ ID NO 32
<211> LENGTH: 22
<212> TYPE: DNA
<213> ORGANISM: Homo sapiens

<400> SEQUENCE: 32
aattaggcaa ttcttgtaaa gc                                          22

<210> SEQ ID NO 33
<211> LENGTH: 22
<212> TYPE: DNA
<213> ORGANISM: Homo sapiens

<400> SEQUENCE: 33
ttaggcaatt cttgtaaagc at                                          22

<210> SEQ ID NO 34
<211> LENGTH: 22
<212> TYPE: DNA
<213> ORGANISM: Homo sapiens

<400> SEQUENCE: 34
aaagcatagg cacacatcac cc                                          22
```

```
<210> SEQ ID NO 35
<211> LENGTH: 22
<212> TYPE: DNA
<213> ORGANISM: Homo sapiens

<400> SEQUENCE: 35
gcctggtctg gcttcagtta ca                                              22

<210> SEQ ID NO 36
<211> LENGTH: 22
<212> TYPE: DNA
<213> ORGANISM: Homo sapiens

<400> SEQUENCE: 36
gtgtccaact ttgtttgctt tc                                              22

<210> SEQ ID NO 37
<211> LENGTH: 22
<212> TYPE: DNA
<213> ORGANISM: Homo sapiens

<400> SEQUENCE: 37
gtattctgga aagcaaacaa ag                                              22

<210> SEQ ID NO 38
<211> LENGTH: 22
<212> TYPE: DNA
<213> ORGANISM: Homo sapiens

<400> SEQUENCE: 38
cagtcttggc atcacaggct tc                                              22

<210> SEQ ID NO 39
<211> LENGTH: 22
<212> TYPE: DNA
<213> ORGANISM: Homo sapiens

<400> SEQUENCE: 39
ggacctcttg gctattacac ag                                              22

<210> SEQ ID NO 40
<211> LENGTH: 22
<212> TYPE: DNA
<213> ORGANISM: Homo sapiens

<400> SEQUENCE: 40
ggagccagtg ggacctcttg gc                                              22

<210> SEQ ID NO 41
<211> LENGTH: 20
<212> TYPE: DNA
<213> ORGANISM: Homo sapiens

<400> SEQUENCE: 41
ttgggcatgt ttgagctggt                                                 20

<210> SEQ ID NO 42
<211> LENGTH: 20
<212> TYPE: DNA
<213> ORGANISM: Homo sapiens

<400> SEQUENCE: 42
tttgggcatg tttgagctgg                                                 20
```

<210> SEQ ID NO 43
<211> LENGTH: 20
<212> TYPE: DNA
<213> ORGANISM: Homo sapiens

<400> SEQUENCE: 43
gagctggtgg gcgaagcata                                               20

<210> SEQ ID NO 44
<211> LENGTH: 20
<212> TYPE: DNA
<213> ORGANISM: Homo sapiens

<400> SEQUENCE: 44
agctggtggg cgaagcatat                                               20

<210> SEQ ID NO 45
<211> LENGTH: 20
<212> TYPE: DNA
<213> ORGANISM: Homo sapiens

<400> SEQUENCE: 45
tgggcgaagc atatgggcaa                                               20

<210> SEQ ID NO 46
<211> LENGTH: 20
<212> TYPE: DNA
<213> ORGANISM: Homo sapiens

<400> SEQUENCE: 46
ggcctccatc ctaaacaatg                                               20

<210> SEQ ID NO 47
<211> LENGTH: 20
<212> TYPE: DNA
<213> ORGANISM: Homo sapiens

<400> SEQUENCE: 47
gggttgggag gtttgggcgt                                               20

<210> SEQ ID NO 48
<211> LENGTH: 20
<212> TYPE: DNA
<213> ORGANISM: Homo sapiens

<400> SEQUENCE: 48
aggtttgggc gtgggagtcc                                               20

<210> SEQ ID NO 49
<211> LENGTH: 19
<212> TYPE: DNA
<213> ORGANISM: Homo sapiens

<400> SEQUENCE: 49
ttcagagact cagctattt                                                19

<210> SEQ ID NO 50
<211> LENGTH: 19
<212> TYPE: DNA
<213> ORGANISM: Homo sapiens

<400> SEQUENCE: 50

```
ggccacattg tttaggatg                                              19

<210> SEQ ID NO 51
<211> LENGTH: 19
<212> TYPE: DNA
<213> ORGANISM: Homo sapiens

<400> SEQUENCE: 51
ggctttgggc atgtttgag                                              19

<210> SEQ ID NO 52
<211> LENGTH: 19
<212> TYPE: DNA
<213> ORGANISM: Homo sapiens

<400> SEQUENCE: 52
aacatgccca aagcccagc                                              19

<210> SEQ ID NO 53
<211> LENGTH: 19
<212> TYPE: DNA
<213> ORGANISM: Homo sapiens

<400> SEQUENCE: 53
acatgcccaa agcccagcg                                              19

<210> SEQ ID NO 54
<211> LENGTH: 23
<212> TYPE: DNA
<213> ORGANISM: Homo sapiens

<400> SEQUENCE: 54
ttaaatcaca gaggcaaaga gtt                                         23

<210> SEQ ID NO 55
<211> LENGTH: 22
<212> TYPE: DNA
<213> ORGANISM: Homo sapiens

<400> SEQUENCE: 55
ttgcatagtg ctagactgtt tt                                          22

<210> SEQ ID NO 56
<211> LENGTH: 22
<212> TYPE: DNA
<213> ORGANISM: Homo sapiens

<400> SEQUENCE: 56
gggtcatgtg ttttgaaaac ag                                          22

<210> SEQ ID NO 57
<211> LENGTH: 22
<212> TYPE: DNA
<213> ORGANISM: Homo sapiens

<400> SEQUENCE: 57
cccaaacctc ccaacccaca ac                                          22

<210> SEQ ID NO 58
<211> LENGTH: 22
<212> TYPE: DNA
<213> ORGANISM: Homo sapiens

<400> SEQUENCE: 58
```

```
actcagctat ttctggaatg ac                                              22

<210> SEQ ID NO 59
<211> LENGTH: 22
<212> TYPE: DNA
<213> ORGANISM: Homo sapiens

<400> SEQUENCE: 59
tcatcgcctt tgtgagctcc at                                              22

<210> SEQ ID NO 60
<211> LENGTH: 22
<212> TYPE: DNA
<213> ORGANISM: Homo sapiens

<400> SEQUENCE: 60
cagacacagg ctttgctcta gc                                              22

<210> SEQ ID NO 61
<211> LENGTH: 22
<212> TYPE: DNA
<213> ORGANISM: Homo sapiens

<400> SEQUENCE: 61
caaagcctgt gtctggccac ta                                              22

<210> SEQ ID NO 62
<211> LENGTH: 22
<212> TYPE: DNA
<213> ORGANISM: Homo sapiens

<400> SEQUENCE: 62
agcagtttgt gcccactagt gg                                              22

<210> SEQ ID NO 63
<211> LENGTH: 22
<212> TYPE: DNA
<213> ORGANISM: Homo sapiens

<400> SEQUENCE: 63
atgtcaaggt attccagcta ac                                              22

<210> SEQ ID NO 64
<211> LENGTH: 22
<212> TYPE: DNA
<213> ORGANISM: Homo sapiens

<400> SEQUENCE: 64
gaataactgt atcaaagtta gc                                              22

<210> SEQ ID NO 65
<211> LENGTH: 22
<212> TYPE: DNA
<213> ORGANISM: Homo sapiens

<400> SEQUENCE: 65
ttcctaatta agaggctttg tg                                              22

<210> SEQ ID NO 66
<211> LENGTH: 22
<212> TYPE: DNA
<213> ORGANISM: Homo sapiens
```

```
<400> SEQUENCE: 66
gagctagttt gtcagggtct ag                                              22

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
cacagggcag tcagagaccc                                                 20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
gcaaacaaag ttggacactg                                                 20

<210> SEQ ID NO 69
<211> LENGTH: 24
<212> TYPE: DNA
<213> ORGANISM: Artificial Sequence
<220> FEATURE:
<223> OTHER INFORMATION: primer

<400> SEQUENCE: 69
agactcccgc ccatcttcta gaaa                                            24

<210> SEQ ID NO 70
<211> LENGTH: 24
<212> TYPE: DNA
<213> ORGANISM: Artificial Sequence
<220> FEATURE:
<223> OTHER INFORMATION: primer

<400> SEQUENCE: 70
aagtcgctct gagttgttat cagt                                            24

<210> SEQ ID NO 71
<211> LENGTH: 19
<212> TYPE: DNA
<213> ORGANISM: Artificial Sequence
<220> FEATURE:
<223> OTHER INFORMATION: primer

<400> SEQUENCE: 71
cagtgaaacg caccagacg                                                  19

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
aatctgccta acaggaggtg                                                 20

<210> SEQ ID NO 73
<211> LENGTH: 24
```

```
<212> TYPE: DNA
<213> ORGANISM: Artificial Sequence
<220> FEATURE:
<223> OTHER INFORMATION: primer

<400> SEQUENCE: 73
gagggaatgg ggaccaaagg catt                                          24

<210> SEQ ID NO 74
<211> LENGTH: 24
<212> TYPE: DNA
<213> ORGANISM: Artificial Sequence
<220> FEATURE:
<223> OTHER INFORMATION: primer

<400> SEQUENCE: 74
tcatgtgggg tgatgttcag gaag                                          24

<210> SEQ ID NO 75
<211> LENGTH: 23
<212> TYPE: DNA
<213> ORGANISM: Artificial Sequence
<220> FEATURE:
<223> OTHER INFORMATION: primer

<400> SEQUENCE: 75
agagcagctg acctgaggtc caa                                           23

<210> SEQ ID NO 76
<211> LENGTH: 24
<212> TYPE: DNA
<213> ORGANISM: Artificial Sequence
<220> FEATURE:
<223> OTHER INFORMATION: primer

<400> SEQUENCE: 76
cccaagggta gagtgcaagt aaac                                          24

<210> SEQ ID NO 77
<211> LENGTH: 24
<212> TYPE: DNA
<213> ORGANISM: Artificial Sequence
<220> FEATURE:
<223> OTHER INFORMATION: primer

<400> SEQUENCE: 77
gcatcctagc tcatttggtc tgct                                          24

<210> SEQ ID NO 78
<211> LENGTH: 24
<212> TYPE: DNA
<213> ORGANISM: Artificial Sequence
<220> FEATURE:
<223> OTHER INFORMATION: primer

<400> SEQUENCE: 78
gagaggattc ctcatgaatg ggat                                          24

<210> SEQ ID NO 79
<211> LENGTH: 24
<212> TYPE: DNA
<213> ORGANISM: Artificial Sequence
<220> FEATURE:
<223> OTHER INFORMATION: primer

<400> SEQUENCE: 79
```
accaaacact acacttggtt actg                                              24

<210> SEQ ID NO 80
<211> LENGTH: 24
<212> TYPE: DNA
<213> ORGANISM: Artificial Sequence
<220> FEATURE:
<223> OTHER INFORMATION: primer

<400> SEQUENCE: 80
ctcccactag caattttaaa gtct                                              24

<210> SEQ ID NO 81
<211> LENGTH: 24
<212> TYPE: DNA
<213> ORGANISM: Artificial Sequence
<220> FEATURE:
<223> OTHER INFORMATION: primer

<400> SEQUENCE: 81
gaatgttcag cacaggtttc cttg                                              24

<210> SEQ ID NO 82
<211> LENGTH: 24
<212> TYPE: DNA
<213> ORGANISM: Artificial Sequence
<220> FEATURE:
<223> OTHER INFORMATION: primer

<400> SEQUENCE: 82
ggtcaaaagg agctccatat ttga                                              24

<210> SEQ ID NO 83
<211> LENGTH: 24
<212> TYPE: DNA
<213> ORGANISM: Artificial Sequence
<220> FEATURE:
<223> OTHER INFORMATION: primer

<400> SEQUENCE: 83
caggacaccc atggccaaat ccag                                              24

<210> SEQ ID NO 84
<211> LENGTH: 24
<212> TYPE: DNA
<213> ORGANISM: Artificial Sequence
<220> FEATURE:
<223> OTHER INFORMATION: primer

<400> SEQUENCE: 84
cagagcctcc tgcagggatg tcaa                                              24

<210> SEQ ID NO 85
<211> LENGTH: 24
<212> TYPE: DNA
<213> ORGANISM: Artificial Sequence
<220> FEATURE:
<223> OTHER INFORMATION: primer

<400> SEQUENCE: 85
gcctgccaag gtgactctca tcta                                              24

<210> SEQ ID NO 86
<211> LENGTH: 24
<212> TYPE: DNA
<213> ORGANISM: Artificial Sequence

```
<220> FEATURE:
<223> OTHER INFORMATION: primer

<400> SEQUENCE: 86
tgcccaggct gatcttgaac tcct                                              24

<210> SEQ ID NO 87
<211> LENGTH: 24
<212> TYPE: DNA
<213> ORGANISM: Artificial Sequence
<220> FEATURE:
<223> OTHER INFORMATION: primer

<400> SEQUENCE: 87
cccagagtta agaggttctt tcct                                              24

<210> SEQ ID NO 88
<211> LENGTH: 24
<212> TYPE: DNA
<213> ORGANISM: Artificial Sequence
<220> FEATURE:
<223> OTHER INFORMATION: primer

<400> SEQUENCE: 88
gaagctactc cagtgcaact agct                                              24

<210> SEQ ID NO 89
<211> LENGTH: 23
<212> TYPE: DNA
<213> ORGANISM: Artificial Sequence
<220> FEATURE:
<223> OTHER INFORMATION: primer

<400> SEQUENCE: 89
acgcagtctg ttctgtgcag tgt                                               23

<210> SEQ ID NO 90
<211> LENGTH: 24
<212> TYPE: DNA
<213> ORGANISM: Artificial Sequence
<220> FEATURE:
<223> OTHER INFORMATION: primer

<400> SEQUENCE: 90
aggccttccc aaggaagacc ctga                                              24

<210> SEQ ID NO 91
<211> LENGTH: 24
<212> TYPE: DNA
<213> ORGANISM: Artificial Sequence
<220> FEATURE:
<223> OTHER INFORMATION: primer

<400> SEQUENCE: 91
gctgatcact ggccaaatcc agct                                              24

<210> SEQ ID NO 92
<211> LENGTH: 24
<212> TYPE: DNA
<213> ORGANISM: Artificial Sequence
<220> FEATURE:
<223> OTHER INFORMATION: primer

<400> SEQUENCE: 92
gggaaacaat gggatcaagc tgca                                              24
```

```
<210> SEQ ID NO 93
<211> LENGTH: 24
<212> TYPE: DNA
<213> ORGANISM: Artificial Sequence
<220> FEATURE:
<223> OTHER INFORMATION: primer

<400> SEQUENCE: 93 gccccttttgt aagttgagga gcat                                          24

<210> SEQ ID NO 94
<211> LENGTH: 24
<212> TYPE: DNA
<213> ORGANISM: Artificial Sequence
<220> FEATURE:
<223> OTHER INFORMATION: primer

<400> SEQUENCE: 94
ccctctacct ctctcaatgg gctt                                           24

<210> SEQ ID NO 95
<211> LENGTH: 24
<212> TYPE: DNA
<213> ORGANISM: Artificial Sequence
<220> FEATURE:
<223> OTHER INFORMATION: primer

<400> SEQUENCE: 95
cagacaagca aatgctgaga gatt                                           24

<210> SEQ ID NO 96
<211> LENGTH: 24
<212> TYPE: DNA
<213> ORGANISM: Artificial Sequence
<220> FEATURE:
<223> OTHER INFORMATION: primer

<400> SEQUENCE: 96
cctgtcatta tgatgttcgc tagt                                           24

<210> SEQ ID NO 97
<211> LENGTH: 24
<212> TYPE: DNA
<213> ORGANISM: Artificial Sequence
<220> FEATURE:
<223> OTHER INFORMATION: primer

<400> SEQUENCE: 97
ccagagttgg cctcctacag agat                                           24

<210> SEQ ID NO 98
<211> LENGTH: 24
<212> TYPE: DNA
<213> ORGANISM: Artificial Sequence
<220> FEATURE:
<223> OTHER INFORMATION: primer

<400> SEQUENCE: 98
gtggatgccc cactactgtt catt                                           24

<210> SEQ ID NO 99
<211> LENGTH: 24
<212> TYPE: DNA
<213> ORGANISM: Artificial Sequence
<220> FEATURE:
<223> OTHER INFORMATION: primer
```

```
<400> SEQUENCE: 99
tacccaattt gccagtctgt gtct                                          24

<210> SEQ ID NO 100
<211> LENGTH: 23
<212> TYPE: DNA
<213> ORGANISM: Artificial Sequence
<220> FEATURE:
<223> OTHER INFORMATION: primer

<400> SEQUENCE: 100
accaccaggc ctgccctaca aga                                           23

<210> SEQ ID NO 101
<211> LENGTH: 24
<212> TYPE: DNA
<213> ORGANISM: Artificial Sequence
<220> FEATURE:
<223> OTHER INFORMATION: primer

<400> SEQUENCE: 101
tgtgaatttg atcctggcat tatg                                          24

<210> SEQ ID NO 102
<211> LENGTH: 24
<212> TYPE: DNA
<213> ORGANISM: Artificial Sequence
<220> FEATURE:
<223> OTHER INFORMATION: primer

<400> SEQUENCE: 102
tacagacaag cagatgctga gaga                                          24

<210> SEQ ID NO 103
<211> LENGTH: 24
<212> TYPE: DNA
<213> ORGANISM: Artificial Sequence
<220> FEATURE:
<223> OTHER INFORMATION: primer

<400> SEQUENCE: 103
cagtcaacag agctctaacc tcct                                          24

<210> SEQ ID NO 104
<211> LENGTH: 23
<212> TYPE: DNA
<213> ORGANISM: Artificial Sequence
<220> FEATURE:
<223> OTHER INFORMATION: primer

<400> SEQUENCE: 104
agcacctggt tgcacatcaa ctt                                           23

<210> SEQ ID NO 105
<211> LENGTH: 24
<212> TYPE: DNA
<213> ORGANISM: Artificial Sequence
<220> FEATURE:
<223> OTHER INFORMATION: primer

<400> SEQUENCE: 105
catgtggtcc ctgaacgtga atga                                          24

<210> SEQ ID NO 106
```

```
<211> LENGTH: 23
<212> TYPE: DNA
<213> ORGANISM: Artificial Sequence
<220> FEATURE:
<223> OTHER INFORMATION: primer

<400> SEQUENCE: 106
gtctgtcgct tgccctcttc tct                                          23

<210> SEQ ID NO 107
<211> LENGTH: 24
<212> TYPE: DNA
<213> ORGANISM: Artificial Sequence
<220> FEATURE:
<223> OTHER INFORMATION: primer

<400> SEQUENCE: 107
atgcagggcc tctagaccat ttca                                         24

<210> SEQ ID NO 108
<211> LENGTH: 23
<212> TYPE: DNA
<213> ORGANISM: Artificial Sequence
<220> FEATURE:
<223> OTHER INFORMATION: primer

<400> SEQUENCE: 108
ctcagccctt tgtgcactca cct                                          23

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
tgcacatcgc aaacatttcg                                              20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
tgggtatcgc actgtgtcag                                              20

<210> SEQ ID NO 111
<211> LENGTH: 20
<212> TYPE: DNA
<213> ORGANISM: Artificial Sequence
<220> FEATURE:
<223> OTHER INFORMATION: primer

<400> SEQUENCE: 111
aggttcacat ggcttgtggt                                              20

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
```
atatctgaaa tgcccgcagg                                                    20

<210> SEQ ID NO 113
<211> LENGTH: 20
<212> TYPE: DNA
<213> ORGANISM: Artificial Sequence
<220> FEATURE:
<223> OTHER INFORMATION: primer

<400> SEQUENCE: 113
tgcacatcgc aaacatttcg                                                    20

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
tgggtatcgc actgtgtcag                                                    20

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
tctttaaagg ccttatctcc                                                    20

<210> SEQ ID NO 116
<211> LENGTH: 20
<212> TYPE: DNA
<213> ORGANISM: Artificial Sequence
<220> FEATURE:
<223> OTHER INFORMATION: primer

<400> SEQUENCE: 116
ttctgcttga gaattcatcc                                                    20

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
ctcctaatct ttcacttagg                                                    20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
caaagcctgg tataacatag                                                    20

<210> SEQ ID NO 119
<211> LENGTH: 19
<212> TYPE: DNA

```
<213> ORGANISM: Artificial Sequence
<220> FEATURE:
<223> OTHER INFORMATION: primer

<400> SEQUENCE: 119
tcacttcgag catctgtgg                                               19

<210> SEQ ID NO 120
<211> LENGTH: 19
<212> TYPE: DNA
<213> ORGANISM: Artificial Sequence
<220> FEATURE:
<223> OTHER INFORMATION: primer

<400> SEQUENCE: 120
ccaaatgaca ggctgagct                                               19

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
agcaggaagt gaaggctaag                                              20

<210> SEQ ID NO 122
<211> LENGTH: 20
<212> TYPE: DNA
<213> ORGANISM: Artificial Sequence
<220> FEATURE:
<223> OTHER INFORMATION: primer

<400> SEQUENCE: 122
atgtaacgtg gcaactctgg                                              20

<210> SEQ ID NO 123
<211> LENGTH: 20
<212> TYPE: DNA
<213> ORGANISM: Artificial Sequence
<220> FEATURE:
<223> OTHER INFORMATION: primer

<400> SEQUENCE: 123
gtgttgctct cgtcaattag                                              20

<210> SEQ ID NO 124
<211> LENGTH: 20
<212> TYPE: DNA
<213> ORGANISM: Artificial Sequence
<220> FEATURE:
<223> OTHER INFORMATION: primer

<400> SEQUENCE: 124
aggtgttgta catggagaag                                              20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
tgtgagccac catacccagc                                              20
```

```
<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
cctgcagtcc tttgcggatc                                                 20

<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127
tcgctgccag tataacatgc                                                 20

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
aactccagtc tctagactcg                                                 20

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
aatagtttga cgttggagcc                                                 20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
actcccaaca tgttctcctg                                                 20

<210> SEQ ID NO 131
<211> LENGTH: 19
<212> TYPE: DNA
<213> ORGANISM: Artificial Sequence
<220> FEATURE:
<223> OTHER INFORMATION: primer

<400> SEQUENCE: 131
atcatcgctc acagagtcc                                                  19

<210> SEQ ID NO 132
<211> LENGTH: 20
<212> TYPE: DNA
<213> ORGANISM: Artificial Sequence
<220> FEATURE:
```

<223> OTHER INFORMATION: primer

<400> SEQUENCE: 132
acgactgcag gatcttaatg                    20

<210> SEQ ID NO 133
<211> LENGTH: 20
<212> TYPE: DNA
<213> ORGANISM: Artificial Sequence
<220> FEATURE:
<223> OTHER INFORMATION: primer

<400> SEQUENCE: 133
tggatggagg ttgggaatcc                    20

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
ttgaggcagc agcactctcc                    20

<210> SEQ ID NO 135
<211> LENGTH: 19
<212> TYPE: DNA
<213> ORGANISM: Artificial Sequence
<220> FEATURE:
<223> OTHER INFORMATION: primer

<400> SEQUENCE: 135
agtctatcct agcagctcc                    19

<210> SEQ ID NO 136
<211> LENGTH: 20
<212> TYPE: DNA
<213> ORGANISM: Artificial Sequence
<220> FEATURE:
<223> OTHER INFORMATION: primer

<400> SEQUENCE: 136
actgagacca gataatgcag                    20

<210> SEQ ID NO 137
<211> LENGTH: 19
<212> TYPE: DNA
<213> ORGANISM: Artificial Sequence
<220> FEATURE:
<223> OTHER INFORMATION: primer

<400> SEQUENCE: 137
aagagatgcg agttgttcc                    19

<210> SEQ ID NO 138
<211> LENGTH: 19
<212> TYPE: DNA
<213> ORGANISM: Artificial Sequence
<220> FEATURE:
<223> OTHER INFORMATION: primer

<400> SEQUENCE: 138
cctcttctac tctgagtgg                    19

```
<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
acctggttta tcacaagcta                                               20

<210> SEQ ID NO 140
<211> LENGTH: 20
<212> TYPE: DNA
<213> ORGANISM: Artificial Sequence
<220> FEATURE:
<223> OTHER INFORMATION: primer

<400> SEQUENCE: 140
aacgtgaaca gaaggatttc                                               20

<210> SEQ ID NO 141
<211> LENGTH: 20
<212> TYPE: DNA
<213> ORGANISM: Artificial Sequence
<220> FEATURE:
<223> OTHER INFORMATION: primer

<400> SEQUENCE: 141
atcactccat cagagtcagg                                               20

<210> SEQ ID NO 142
<211> LENGTH: 20
<212> TYPE: DNA
<213> ORGANISM: Artificial Sequence
<220> FEATURE:
<223> OTHER INFORMATION: primer

<400> SEQUENCE: 142
tggctccttc tattctctcc                                               20

<210> SEQ ID NO 143
<211> LENGTH: 23
<212> TYPE: DNA
<213> ORGANISM: Homo sapiens

<400> SEQUENCE: 143
tatggaattc ccaagccccc tgg                                           23

<210> SEQ ID NO 144
<211> LENGTH: 23
<212> TYPE: DNA
<213> ORGANISM: Homo sapiens

<400> SEQUENCE: 144
ggaattccat atgagtcatc tgg                                           23

<210> SEQ ID NO 145
<211> LENGTH: 23
<212> TYPE: DNA
<213> ORGANISM: Homo sapiens

<400> SEQUENCE: 145
cacagcctac actttgatta tgg                                           23

<210> SEQ ID NO 146
```

```
<211> LENGTH: 23
<212> TYPE: DNA
<213> ORGANISM: Homo sapiens

<400> SEQUENCE: 146
tcaggagcat taagcatata ggg                                              23

<210> SEQ ID NO 147
<211> LENGTH: 23
<212> TYPE: DNA
<213> ORGANISM: Homo sapiens

<400> SEQUENCE: 147
gaccacggtc catgaattcc tgg                                              23

<210> SEQ ID NO 148
<211> LENGTH: 23
<212> TYPE: DNA
<213> ORGANISM: Homo sapiens

<400> SEQUENCE: 148
agtatttgca gctgaacaaa agg                                              23

<210> SEQ ID NO 149
<211> LENGTH: 12
<212> TYPE: RNA
<213> ORGANISM: Artificial Sequence
<220> FEATURE:
<223> OTHER INFORMATION: first complementary domain

<400> SEQUENCE: 149
guuuuagagc ua                                                          12

<210> SEQ ID NO 150
<211> LENGTH: 23
<212> TYPE: DNA
<213> ORGANISM: Homo sapiens

<400> SEQUENCE: 150
atggagtaca gagagacata agg                                              23

<210> SEQ ID NO 151
<211> LENGTH: 23
<212> TYPE: DNA
<213> ORGANISM: Homo sapiens

<400> SEQUENCE: 151
aaagaatcaa tgcacagcca tgg                                              23

<210> SEQ ID NO 152
<211> LENGTH: 25
<212> TYPE: RNA
<213> ORGANISM: Artificial Sequence
<220> FEATURE:
<223> OTHER INFORMATION: first complementary domain

<400> SEQUENCE: 152
guuuuagucc cuuuuuaaau uucuu                                            25

<210> SEQ ID NO 153
<211> LENGTH: 22
<212> TYPE: RNA
<213> ORGANISM: Artificial Sequence
<220> FEATURE:
<223> OTHER INFORMATION: firtst complementary domain
```

```
<400> SEQUENCE: 153
guuuuagagc uguguuguuu cg                                      22

<210> SEQ ID NO 154
<211> LENGTH: 9
<212> TYPE: RNA
<213> ORGANISM: Artificial Sequence
<220> FEATURE:
<223> OTHER INFORMATION: first complementary domain

<400> SEQUENCE: 154 uuuguagau                                                      9

<210> SEQ ID NO 155
<211> LENGTH: 14
<212> TYPE: RNA
<213> ORGANISM: Artificial Sequence
<220> FEATURE:
<223> OTHER INFORMATION: second complementary domain

<400> SEQUENCE: 155
uagcaaguua aaau                                               14

<210> SEQ ID NO 156
<211> LENGTH: 24
<212> TYPE: RNA
<213> ORGANISM: Artificial Sequence
<220> FEATURE:
<223> OTHER INFORMATION: second complementary domain

<400> SEQUENCE: 156
cgaaacaaca cagcgaguua aaau                                    24

<210> SEQ ID NO 157
<211> LENGTH: 25
<212> TYPE: RNA
<213> ORGANISM: Artificial Sequence
<220> FEATURE:
<223> OTHER INFORMATION: second complementary domain

<400> SEQUENCE: 157
aagaaauuua aaagggacu aaaau                                    25

<210> SEQ ID NO 158
<211> LENGTH: 12
<212> TYPE: RNA
<213> ORGANISM: Artificial Sequence
<220> FEATURE:
<223> OTHER INFORMATION: proximal domain

<400> SEQUENCE: 158
aaggcuaguc cg                                                 12

<210> SEQ ID NO 159
<211> LENGTH: 11
<212> TYPE: RNA
<213> ORGANISM: Artificial Sequence
<220> FEATURE:
<223> OTHER INFORMATION: proximal domain

<400> SEQUENCE: 159
aaagaguuug c                                                  11

<210> SEQ ID NO 160
```

```
<211> LENGTH: 11
<212> TYPE: RNA
<213> ORGANISM: Artificial Sequence
<220> FEATURE:
<223> OTHER INFORMATION: second complementary domain

<400> SEQUENCE: 160
aaauuucuac u                                                               11

<210> SEQ ID NO 161
<211> LENGTH: 34
<212> TYPE: RNA
<213> ORGANISM: Artificial Sequence
<220> FEATURE:
<223> OTHER INFORMATION: tail domain

<400> SEQUENCE: 161
uuaucaacuu gaaaaagugg caccgagucg gugc                                      34

<210> SEQ ID NO 162
<211> LENGTH: 38
<212> TYPE: RNA
<213> ORGANISM: Artificial Sequence
<220> FEATURE:
<223> OTHER INFORMATION: tail domain

<400> SEQUENCE: 162
gggacucugc gggguuacaa uccccuaaaa ccgcuuuu                                  38

<210> SEQ ID NO 163
<211> LENGTH: 38
<212> TYPE: RNA
<213> ORGANISM: Artificial Sequence
<220> FEATURE:
<223> OTHER INFORMATION: tail domain

<400> SEQUENCE: 163
uacucaacuu gaaaaggugg caccgauucg guguuuuu                                  38

<210> SEQ ID NO 164
<211> LENGTH: 76
<212> TYPE: RNA
<213> ORGANISM: Artificial Sequence
<220> FEATURE:
<223> OTHER INFORMATION: sgRNA backbone

<400> SEQUENCE: 164
guuuuagagc uagaaauagc aaguuaaaau aaggcuaguc cguuaucaac uugaaaaagu          60
ggcaccgagu cggugc                                                          76

<210> SEQ ID NO 165
<211> LENGTH: 11
<212> TYPE: RNA
<213> ORGANISM: Artificial Sequence
<220> FEATURE:
<223> OTHER INFORMATION: proximal domain

<400> SEQUENCE: 165
aaagaguuug c                                                               11

<210> SEQ ID NO 166
<211> LENGTH: 13
<212> TYPE: RNA
<213> ORGANISM: Artificial Sequence
<220> FEATURE:
<223> OTHER INFORMATION: proximal domain
```

```
<400> SEQUENCE: 166
aaggcuuagu ccg                                                            13

<210> SEQ ID NO 167
<211> LENGTH: 77
<212> TYPE: RNA
<213> ORGANISM: Artificial Sequence
<220> FEATURE:
<223> OTHER INFORMATION: sgRNA backbone

<400> SEQUENCE: 167
guuuuagucc cugaaaaggg acuaaaauaa agaguuugcg ggacucugcg ggguuacaau         60
ccccuaaaac cgcuuuu                                                        77

<210> SEQ ID NO 168
<211> LENGTH: 76
<212> TYPE: RNA
<213> ORGANISM: Artificial Sequence
<220> FEATURE:
<223> OTHER INFORMATION: sgRNA backbone

<400> SEQUENCE: 168
guuuuagagc uagaaauagc aaguuaaaau aaggcuaguc cguuaucaac uugaaaaagu         60
ggcaccgagu cggugc                                                         76

<210> SEQ ID NO 169
<211> LENGTH: 16
<212> TYPE: PRT
<213> ORGANISM: Artificial Sequence
<220> FEATURE:
<223> OTHER INFORMATION: nuclear localization sequence

<400> SEQUENCE: 169

Lys Arg Pro Ala Ala Thr Lys Lys Ala Gly Gln Ala Lys Lys Lys Lys
1               5                   10                  15

<210> SEQ ID NO 170
<211> LENGTH: 11
<212> TYPE: PRT
<213> ORGANISM: Artificial Sequence
<220> FEATURE:
<223> OTHER INFORMATION: nuclear localization sequence

<400> SEQUENCE: 170

Arg Gln Arg Arg Asn Glu Leu Lys Arg Ser Pro
1               5                   10

<210> SEQ ID NO 171
<211> LENGTH: 38
<212> TYPE: PRT
<213> ORGANISM: Artificial Sequence
<220> FEATURE:
<223> OTHER INFORMATION: nuclear localization sequence

<400> SEQUENCE: 171

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
        35
```

<210> SEQ ID NO 172
<211> LENGTH: 42
<212> TYPE: PRT
<213> ORGANISM: Artificial Sequence
<220> FEATURE:
<223> OTHER INFORMATION: nuclear localization sequence

<400> SEQUENCE: 172

Arg Met Arg Ile Glx Phe Lys Asn Lys Gly Lys Asp Thr Ala Glu Leu
1               5                   10                  15

Arg Arg Arg Arg Val Glu Val Ser Glu Leu Arg Lys Ala Lys Lys
            20                  25                  30

Asp Glu Gln Ile Leu Lys Arg Arg Asn Val
        35                  40

<210> SEQ ID NO 173
<211> LENGTH: 12
<212> TYPE: PRT
<213> ORGANISM: Artificial Sequence
<220> FEATURE:
<223> OTHER INFORMATION: nuclear localization sequence

<400> SEQUENCE: 173

Ser Ala Leu Ile Lys Lys Lys Lys Lys Met Ala Pro
1               5                   10

<210> SEQ ID NO 174
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 174

Arg Lys Leu Lys Lys Lys Ile Lys Lys Leu
1               5                   10

<210> SEQ ID NO 175
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 175

Arg Glu Lys Lys Lys Phe Leu Lys Arg Arg
1               5                   10

<210> SEQ ID NO 176
<211> LENGTH: 20
<212> TYPE: PRT
<213> ORGANISM: Artificial Sequence
<220> FEATURE:
<223> OTHER INFORMATION: nuclear localization sequence

<400> SEQUENCE: 176

Lys Arg Lys Gly Asp Glu Val Asp Gly Val Asp Glu Val Ala Lys Lys
1               5                   10                  15

Lys Ser Lys Lys
            20

<210> SEQ ID NO 177
<211> LENGTH: 17
<212> TYPE: PRT
<213> ORGANISM: Artificial Sequence
<220> FEATURE:

-continued

```
<223> OTHER INFORMATION: nuclear localization sequence

<400> SEQUENCE: 177

Arg Lys Cys Leu Gln Ala Gly Met Asn Leu Glu Ala Arg Lys Thr Lys
1               5                   10                  15

Lys

<210> SEQ ID NO 178
<211> LENGTH: 13
<212> TYPE: RNA
<213> ORGANISM: Artificial Sequence
<220> FEATURE:
<223> OTHER INFORMATION: first complementary domain
<220> FEATURE:
<221> NAME/KEY: misc_feature
<222> LOCATION: (13)..(13)
<223> OTHER INFORMATION: n may be A, T, U, or G and may be 5 to 15 bases

<400> SEQUENCE: 178
guuuuagagc uan                                                          13

<210> SEQ ID NO 179
<211> LENGTH: 26
<212> TYPE: RNA
<213> ORGANISM: Artificial Sequence
<220> FEATURE:
<223> OTHER INFORMATION: first complementary domain
<220> FEATURE:
<221> NAME/KEY: misc_feature
<222> LOCATION: (26)..(26)
<223> OTHER INFORMATION: n may be A, T, U, or G and may be 5 to 15 bases

<400> SEQUENCE: 179
guuuuagucc cuuuuuaaau uucuun                                            26

<210> SEQ ID NO 180
<211> LENGTH: 10
<212> TYPE: RNA
<213> ORGANISM: Artificial Sequence
<220> FEATURE:
<223> OTHER INFORMATION: first complementary domain
<220> FEATURE:
<221> NAME/KEY: misc_feature
<222> LOCATION: (1)..(1)
<223> OTHER INFORMATION: n may be A, T, U, or G and may be 1 to 5 bases

<400> SEQUENCE: 180 nuuuguagau                                                              10

<210> SEQ ID NO 181
<211> LENGTH: 16
<212> TYPE: RNA
<213> ORGANISM: Artificial Sequence
<220> FEATURE:
<223> OTHER INFORMATION: second complimentary domain
<220> FEATURE:
<221> NAME/KEY: misc_feature
<222> LOCATION: (1)..(1)
<223> OTHER INFORMATION: n may be A, T, U, or G and may be 1 to 15 bases
<220> FEATURE:
<221> NAME/KEY: misc_feature
<222> LOCATION: (16)..(16)
<223> OTHER INFORMATION: n may be A, T, U, or G and may be 1 to 15 bases

<400> SEQUENCE: 181
nuagcaaguu aaaaun                                                       16

<210> SEQ ID NO 182
```

```
<211> LENGTH: 27
<212> TYPE: RNA
<213> ORGANISM: Artificial Sequence
<220> FEATURE:
<223> OTHER INFORMATION: second complementary domain
<220> FEATURE:
<221> NAME/KEY: misc_feature
<222> LOCATION: (1)..(1)
<223> OTHER INFORMATION: n may be A, T, U, or G and may be 1 to 15 bases
<220> FEATURE:
<221> NAME/KEY: misc_feature
<222> LOCATION: (27)..(27)
<223> OTHER INFORMATION: n may be A, T, U, or G and may be 1 to 15 bases

<400> SEQUENCE: 182
naagaaauuu aaaaagggac uaaaaun                                              27

<210> SEQ ID NO 183
<211> LENGTH: 13
<212> TYPE: RNA
<213> ORGANISM: Artificial Sequence
<220> FEATURE:
<223> OTHER INFORMATION: second complementary domain
<220> FEATURE:
<221> NAME/KEY: misc_feature
<222> LOCATION: (1)..(1)
<223> OTHER INFORMATION: n may be A, T, U, or G and may be 1 to 10 bases
<220> FEATURE:
<221> NAME/KEY: misc_feature
<222> LOCATION: (13)..(13)
<223> OTHER INFORMATION: n may be A, T, U, or G and may be 1 to 10 bases

<400> SEQUENCE: 183
naaauuucua cun                                                             13

<210> SEQ ID NO 184
<211> LENGTH: 12
<212> TYPE: RNA
<213> ORGANISM: Artificial Sequence
<220> FEATURE:
<223> OTHER INFORMATION: proximal domain
<220> FEATURE:
<221> NAME/KEY: misc_feature
<222> LOCATION: (12)..(12)
<223> OTHER INFORMATION: n may be A, T, U, or G and may be 1 to 15 bases

<400> SEQUENCE: 184
aaagaguuug cn                                                              12

<210> SEQ ID NO 185
<211> LENGTH: 35
<212> TYPE: RNA
<213> ORGANISM: Artificial Sequence
<220> FEATURE:
<223> OTHER INFORMATION: tail domain
<220> FEATURE:
<221> NAME/KEY: misc_feature
<222> LOCATION: (35)..(35)
<223> OTHER INFORMATION: n may be A, T, U, or G and may be 1 to 15 bases

<400> SEQUENCE: 185
uuaucaacuu gaaaaagugg caccgagucg gugcn                                     35

<210> SEQ ID NO 186
<211> LENGTH: 39
<212> TYPE: RNA
<213> ORGANISM: Artificial Sequence
<220> FEATURE:
<223> OTHER INFORMATION: tail domain
<220> FEATURE:
<221> NAME/KEY: misc_feature
```

```
<222> LOCATION: (39)..(39)
<223> OTHER INFORMATION: n may be A, T, U, or G and may be 1 to 15 bases

<400> SEQUENCE: 186
gggacucugc gggguuacaa uccccuaaaa ccgcuuuun                              39

<210> SEQ ID NO 187
<211> LENGTH: 6
<212> TYPE: RNA
<213> ORGANISM: Artificial Sequence
<220> FEATURE:
<223> OTHER INFORMATION: tail domain

<400> SEQUENCE: 187 uuuuuu                                                                  6

<210> SEQ ID NO 188
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 188

Pro Lys Lys Lys Arg Lys Val
1               5

<210> SEQ ID NO 189
<211> LENGTH: 9
<212> TYPE: PRT
<213> ORGANISM: Artificial Sequence
<220> FEATURE:
<223> OTHER INFORMATION: nuclear localization sequence

<400> SEQUENCE: 189

Pro Ala Ala Lys Arg Val Lys Leu Asp
1               5

<210> SEQ ID NO 190
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 190

Val Ser Arg Lys Arg Pro Arg Pro
1               5

<210> SEQ ID NO 191
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 191

Pro Pro Lys Lys Ala Arg Glu Asp
1               5

<210> SEQ ID NO 192
<211> LENGTH: 7
<212> TYPE: DNA
<213> ORGANISM: Artificial Sequence
<220> FEATURE:
<223> OTHER INFORMATION: PAM sequence
<220> FEATURE:
```

```
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
<220> FEATURE:
<221> NAME/KEY: misc_feature
<222> LOCATION: (7)..(7)
<223> OTHER INFORMATION: n may be A or T

<400> SEQUENCE: 192 nnagaan                                                                 7

<210> SEQ ID NO 193
<211> LENGTH: 8
<212> TYPE: DNA
<213> ORGANISM: Artificial Sequence
<220> FEATURE:
<223> OTHER INFORMATION: PAM sequence
<220> FEATURE:
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
<220> FEATURE:
<221> NAME/KEY: misc_feature
<222> LOCATION: (3)..(3)
<223> OTHER INFORMATION: n may be A, T, G, C, or U
<220> FEATURE:
<221> NAME/KEY: misc_feature
<222> LOCATION: (4)..(4)
<223> OTHER INFORMATION: n may be A, T, G, C, or U

<400> SEQUENCE: 193 nnnngatt                                                                8

<210> SEQ ID NO 194
<211> LENGTH: 8
<212> TYPE: DNA
<213> ORGANISM: Artificial Sequence
<220> FEATURE:
<223> OTHER INFORMATION: PAM sequence
<220> FEATURE:
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
<220> FEATURE:
<221> NAME/KEY: misc_feature
<222> LOCATION: (3)..(3)
<223> OTHER INFORMATION: n may be A, T, G, C, or U
<220> FEATURE:
<221> NAME/KEY: misc_feature
<222> LOCATION: (4)..(4)
<223> OTHER INFORMATION: n may be G or C
<220> FEATURE:
<221> NAME/KEY: misc_feature
<222> LOCATION: (5)..(5)
<223> OTHER INFORMATION: n may be A or G
<220> FEATURE:
<221> NAME/KEY: misc_feature
<222> LOCATION: (6)..(6)
<223> OTHER INFORMATION: n may be C or T

<400> SEQUENCE: 194 nnnnnnac                                                                8
```

```
<210> SEQ ID NO 195
<211> LENGTH: 7
<212> TYPE: DNA
<213> ORGANISM: Artificial Sequence
<220> FEATURE:
<223> OTHER INFORMATION: PAM sequence
<220> FEATURE:
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
<220> FEATURE:
<221> NAME/KEY: misc_feature
<222> LOCATION: (3)..(3)
<223> OTHER INFORMATION: n may be A, T, G, C, or U

<400> SEQUENCE: 195 nnngctt                                                              7

<210> SEQ ID NO 196
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 196

Pro Gln Pro Lys Lys Lys Pro Leu
1               5

<210> SEQ ID NO 197
<211> LENGTH: 5
<212> TYPE: PRT
<213> ORGANISM: Artificial Sequence
<220> FEATURE:
<223> OTHER INFORMATION: nuclear localization sequence

<400> SEQUENCE: 197

Asp Arg Leu Arg Arg
1               5

<210> SEQ ID NO 198
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 198

Pro Lys Gln Lys Lys Arg Lys
1               5

<210> SEQ ID NO 199
<211> LENGTH: 6
<212> TYPE: DNA
<213> ORGANISM: Artificial Sequence
<220> FEATURE:
<223> OTHER INFORMATION: PAM domain
<220> FEATURE:
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
```

```
<220> FEATURE:
<221> NAME/KEY: misc_feature
<222> LOCATION: (4)..(4)
<223> OTHER INFORMATION: n may be A or G
<220> FEATURE:
<221> NAME/KEY: misc_feature
<222> LOCATION: (5)..(5)
<223> OTHER INFORMATION: n may be A or G

<400> SEQUENCE: 199 nngnnt                                                                   6

<210> SEQ ID NO 200
<211> LENGTH: 6
<212> TYPE: DNA
<213> ORGANISM: Artificial Sequence
<220> FEATURE:
<223> OTHER INFORMATION: PAM sequence
<220> FEATURE:
<221> NAME/KEY: misc_feature
<222> LOCATION: (1)..(1)
<223> OTHER INFORMATION: n may be A, T, G, C, or U
<220> FEATURE:
<221> NAME/KEY: misc_feature
<222> LOCATION: (2)..(2)
<223> OTHER INFORMATION: n may be A, T, G, C, or U
<220> FEATURE:
<221> NAME/KEY: misc_feature
<222> LOCATION: (4)..(4)
<223> OTHER INFORMATION: n may be A or G
<220> FEATURE:
<221> NAME/KEY: misc_feature
<222> LOCATION: (5)..(5)
<223> OTHER INFORMATION: n may be A or G
<220> FEATURE:
<221> NAME/KEY: misc_feature
<222> LOCATION: (6)..(6)
<223> OTHER INFORMATION: n may be A, G, or C

<400> SEQUENCE: 200 nngnnn                                                                   6

<210> SEQ ID NO 201
<211> LENGTH: 13
<212> TYPE: RNA
<213> ORGANISM: Artificial Sequence
<220> FEATURE:
<223> OTHER INFORMATION: proximal domain
<220> FEATURE:
<221> NAME/KEY: misc_feature
<222> LOCATION: (13)..(13)
<223> OTHER INFORMATION: n may be A, T, U, or G and may be 1 to 15 bases

<400> SEQUENCE: 201
aaggcuaguc cgn                                                          13

<210> SEQ ID NO 202
<211> LENGTH: 90
<212> TYPE: DNA
<213> ORGANISM: Human

<400> SEQUENCE: 202
ggcctccatc ctaaacaatg tggcctttgc ccatatgctt cgcccaccag ctcaaacatg        60
cccaaaagcc caaagcccag cgtgggtctt                                        90

<210> SEQ ID NO 203
<211> LENGTH: 23
<212> TYPE: DNA
<213> ORGANISM: Artificial Sequence
<220> FEATURE:
```

<223> OTHER INFORMATION: Enh-Sp5 sgRNA

<400> SEQUENCE: 203
cctttgccca tatgcttcgc cca                                         23

<210> SEQ ID NO 204
<211> LENGTH: 23
<212> TYPE: DNA
<213> ORGANISM: Artificial Sequence
<220> FEATURE:
<223> OTHER INFORMATION: Enh-Sp16 sgRNA

<400> SEQUENCE: 204
acatgcccaa agcccagcgt ggg                                         23

<210> SEQ ID NO 205
<211> LENGTH: 39
<212> TYPE: DNA
<213> ORGANISM: Human

<400> SEQUENCE: 205
ggcctccatc ctaaacaatg tggcctttgc gtgggtctt                        39

<210> SEQ ID NO 206
<211> LENGTH: 89
<212> TYPE: DNA
<213> ORGANISM: Human

<400> SEQUENCE: 206
ggtgctccct gtaactgaag ccagaccagg cgtctttcca gtttattcag gggctggtcc    60
aatgctggga tatgtcatgg tggcctgag                                   89

<210> SEQ ID NO 207
<211> LENGTH: 23
<212> TYPE: DNA
<213> ORGANISM: Artificial sequence
<220> FEATURE:
<223> OTHER INFORMATION: TATA-Sp12 sgRNA

<400> SEQUENCE: 207
ccagaccagg cgtctttcca gtt                                         23

<210> SEQ ID NO 208
<211> LENGTH: 23
<212> TYPE: DNA
<213> ORGANISM: Artificial Sequence
<220> FEATURE:
<223> OTHER INFORMATION: TATA-Sp14 sgRNA

<400> SEQUENCE: 208
tccaatgctg ggatatgtca tgg                                         23

<210> SEQ ID NO 209
<211> LENGTH: 40
<212> TYPE: DNA
<213> ORGANISM: human

<400> SEQUENCE: 209
ggtgctcctg taactgaagc cagactcatg gtggcctgag                       40

<210> SEQ ID NO 210
<211> LENGTH: 90
<212> TYPE: DNA
<213> ORGANISM: Human

<400> SEQUENCE: 210
actgaagcca gaccaggcgt ctttccagtt tattcagggg ctggtccaat gctgggatat    60
gtcatggtgg cctgagaggt tctcagcctc    90

<210> SEQ ID NO 211
<211> LENGTH: 88
<212> TYPE: DNA
<213> ORGANISM: Artificial Sequence
<220> FEATURE:
<223> OTHER INFORMATION: PMP22-TATA indel -1

<400> SEQUENCE: 211
actgaagcca gaccaggcgt ctttccagtt attcagggc tggtccaatg ctgggatatg    60
tcatggcggc ctgagaggtt ctcgcctc    88

<210> SEQ ID NO 212
<211> LENGTH: 87
<212> TYPE: DNA
<213> ORGANISM: Artificial Sequence
<220> FEATURE:
<223> OTHER INFORMATION: PMP22-TATA Indel -2

<400> SEQUENCE: 212
actgaagcca gaccaggcgt ctttccagtt ttcaggggct ggtccaatgc tggatatgtc    60
atggyggcct gagaggttct cagcctc    87

<210> SEQ ID NO 213
<211> LENGTH: 91
<212> TYPE: DNA
<213> ORGANISM: Artificial Sequence
<220> FEATURE:
<223> OTHER INFORMATION: PMP22-TATA Indel +1

<400> SEQUENCE: 213
actgaagcca gaccaggcgt ctttccagtt ttattcaggg gctggtccaa tgctgggata    60
tgtcatggcg gcctgagagg ttctcagcct c    91

<210> SEQ ID NO 214
<211> LENGTH: 87
<212> TYPE: DNA
<213> ORGANISM: Artificial Sequence
<220> FEATURE:
<223> OTHER INFORMATION: P<P22-TATA Indel -3

<400> SEQUENCE: 214
actgaagcca gaccaggcgt ctttccagtt tcagggctg gtccaatgct gggatatgtc    60
atggcggcct gagaggttct cagcctc    87

<210> SEQ ID NO 215
<211> LENGTH: 86
<212> TYPE: DNA
<213> ORGANISM: Artificial Sequence
<220> FEATURE:
<223> OTHER INFORMATION: PMP22-TATA Indel -4

<400> SEQUENCE: 215
actgaagcca gaccaggcgt ctttccagtt caggggctgg tccaatgctg ggatatgtca    60
tggcggcctg agaggttctc agcctc    86

<210> SEQ ID NO 216

-continued

```
<211> LENGTH: 23
<212> TYPE: DNA
<213> ORGANISM: Human

<400> SEQUENCE: 216
ggaccagccc ctgaataaac tgg                                              23

<210> SEQ ID NO 217
<211> LENGTH: 23
<212> TYPE: DNA
<213> ORGANISM: Human

<400> SEQUENCE: 217
ggaccagcca cagaataaac aag                                              23

<210> SEQ ID NO 218
<211> LENGTH: 23
<212> TYPE: DNA
<213> ORGANISM: Human

<400> SEQUENCE: 218
tgaccagtcc atgaataaac cag                                              23

<210> SEQ ID NO 219
<211> LENGTH: 22
<212> TYPE: DNA
<213> ORGANISM: human

<400> SEQUENCE: 219
ggaccagaca ctgaatatac ag                                               22

<210> SEQ ID NO 220
<211> LENGTH: 22
<212> TYPE: DNA
<213> ORGANISM: Human

<400> SEQUENCE: 220
ggaccagcca cagaataaat gg                                               22

<210> SEQ ID NO 221
<211> LENGTH: 23
<212> TYPE: DNA
<213> ORGANISM: Human

<400> SEQUENCE: 221
ggatcagccc cagaataaat tag                                              23

<210> SEQ ID NO 222
<211> LENGTH: 23
<212> TYPE: DNA
<213> ORGANISM: Human

<400> SEQUENCE: 222
ggagcatccc cagaataaac cag                                              23

<210> SEQ ID NO 223
<211> LENGTH: 23
<212> TYPE: DNA
<213> ORGANISM: Human

<400> SEQUENCE: 223
ggatcagcgt ctgaataaac aag                                              23
```

```
<210> SEQ ID NO 224
<211> LENGTH: 23
<212> TYPE: DNA
<213> ORGANISM: Human

<400> SEQUENCE: 224
agaccagccc cagaacaaac aag                                              23

<210> SEQ ID NO 225
<211> LENGTH: 23
<212> TYPE: DNA
<213> ORGANISM: Human

<400> SEQUENCE: 225
gtacgagccc ctgaataaat agg                                              23

<210> SEQ ID NO 226
<211> LENGTH: 23
<212> TYPE: DNA
<213> ORGANISM: Human

<400> SEQUENCE: 226
ggaccaaaca ctgaataaac cag                                              23

<210> SEQ ID NO 227
<211> LENGTH: 23
<212> TYPE: DNA
<213> ORGANISM: Human

<400> SEQUENCE: 227
gcaccagcca ctgaattaac aag                                              23

<210> SEQ ID NO 228
<211> LENGTH: 23
<212> TYPE: DNA
<213> ORGANISM: Human

<400> SEQUENCE: 228
gtaccagcca ctgaaaaaac agg                                              23

<210> SEQ ID NO 229
<211> LENGTH: 23
<212> TYPE: DNA
<213> ORGANISM: Human

<400> SEQUENCE: 229
gaaccagccc ctgattagac cag                                              23

<210> SEQ ID NO 230
<211> LENGTH: 23
<212> TYPE: DNA
<213> ORGANISM: Human

<400> SEQUENCE: 230
gtaccagcca ctgaaaaaac agg                                              23

<210> SEQ ID NO 231
<211> LENGTH: 23
<212> TYPE: DNA
<213> ORGANISM: Human

<400> SEQUENCE: 231
gtaccagccc ctgcaaaaac agg                                              23
```

```
<210> SEQ ID NO 232
<211> LENGTH: 23
<212> TYPE: DNA
<213> ORGANISM: Human

<400> SEQUENCE: 232
gcaccaggcc ttgaataaac aag                                              23

<210> SEQ ID NO 233
<211> LENGTH: 23
<212> TYPE: DNA
<213> ORGANISM: Human

<400> SEQUENCE: 233
ggcccagcca ctgagtaaac tag                                              23

<210> SEQ ID NO 234
<211> LENGTH: 23
<212> TYPE: DNA
<213> ORGANISM: Human

<400> SEQUENCE: 234
ggaattgccc ctgaataaac aag                                              23

<210> SEQ ID NO 235
<211> LENGTH: 23
<212> TYPE: DNA
<213> ORGANISM: Human

<400> SEQUENCE: 235
gggaacagcc ctgaataaac ctg                                              23

<210> SEQ ID NO 236
<211> LENGTH: 23
<212> TYPE: DNA
<213> ORGANISM: Human

<400> SEQUENCE: 236
aggaccagct ctgaataacc agg                                              23

<210> SEQ ID NO 237
<211> LENGTH: 23
<212> TYPE: DNA
<213> ORGANISM: Human

<400> SEQUENCE: 237
ggaacagccc tgaataaacc tgg                                              23

<210> SEQ ID NO 238
<211> LENGTH: 23
<212> TYPE: DNA
<213> ORGANISM: Human

<400> SEQUENCE: 238
gagttcagcc cctgaataac agg                                              23

<210> SEQ ID NO 239
<211> LENGTH: 22
<212> TYPE: DNA
<213> ORGANISM: Human

<400> SEQUENCE: 239
gggaccagcc ccagaataaa gg                                               22
```

```
<210> SEQ ID NO 240
<211> LENGTH: 23
<212> TYPE: DNA
<213> ORGANISM: Human

<400> SEQUENCE: 240
aagccaaccc ctgaataaac agg                                              23

<210> SEQ ID NO 241
<211> LENGTH: 23
<212> TYPE: DNA
<213> ORGANISM: Human

<400> SEQUENCE: 241
cacacagccc ctcaataaac tgg                                              23

<210> SEQ ID NO 242
<211> LENGTH: 23
<212> TYPE: DNA
<213> ORGANISM: Human

<400> SEQUENCE: 242
gaggcagccc ctgtataaac tgg                                              23

<210> SEQ ID NO 243
<211> LENGTH: 23
<212> TYPE: DNA
<213> ORGANISM: Human

<400> SEQUENCE: 243
gaccagcccc ctgaataaca tgg                                              23

<210> SEQ ID NO 244
<211> LENGTH: 23
<212> TYPE: DNA
<213> ORGANISM: Human

<400> SEQUENCE: 244
gtaccagccc ctgacaaaac agg                                              23

<210> SEQ ID NO 245
<211> LENGTH: 23
<212> TYPE: DNA
<213> ORGANISM: Human

<400> SEQUENCE: 245
ggagcagccc cggaatgaac agg                                              23

<210> SEQ ID NO 246
<211> LENGTH: 23
<212> TYPE: DNA
<213> ORGANISM: Human

<400> SEQUENCE: 246
ggaccagccc ctgtataccc tgg                                              23

<210> SEQ ID NO 247
<211> LENGTH: 23
<212> TYPE: DNA
<213> ORGANISM: Human

<400> SEQUENCE: 247
```

```
ggaccagccc ctgtataccc tgg                                              23

<210> SEQ ID NO 248
<211> LENGTH: 23
<212> TYPE: DNA
<213> ORGANISM: Human

<400> SEQUENCE: 248
ggccctgccc ctaaataaac agg                                              23

<210> SEQ ID NO 249
<211> LENGTH: 23
<212> TYPE: DNA
<213> ORGANISM: Human

<400> SEQUENCE: 249
ggaccagccc ctgtataccc tgg                                              23

<210> SEQ ID NO 250
<211> LENGTH: 23
<212> TYPE: DNA
<213> ORGANISM: Human

<400> SEQUENCE: 250
ggatcagccc cagaataacc tgg                                              23

<210> SEQ ID NO 251
<211> LENGTH: 23
<212> TYPE: DNA
<213> ORGANISM: Human

<400> SEQUENCE: 251
ggactagccc ctgagtacac tgg                                              23

<210> SEQ ID NO 252
<211> LENGTH: 121
<212> TYPE: DNA
<213> ORGANISM: Human

<400> SEQUENCE: 252
cctggtggtg ctccctgtaa ctgaagccag accaggcgtc tttccagttt attcaggggc      60
ttggtccaat gctgggatat gtcatggtgg cctgagaggt tctcagcctc tattatttaa     120
a                                                                    121
```

ARTIFICIALLY ENGINEERED SC FUNCTION CONTROL SYSTEM

FIELD

The present invention relates to an artificially manipulated SC function-controlling factor for SC function control and/or the treatment or alleviation of a disease due to an SC function disorder, and to a use thereof. More specifically, the present invention relates to a system capable of performing artificial SC function control and/or treating or alleviating a disease due to an SC function disorder, the system comprising: an artificially manipulated SC function-controlling factor for SC function control and/or the treatment or alleviation of a disease due to an SC function disorder; and/or a composition for treating or alleviating a disease due to an SC function disorder.

BACKGROUND

Schwann cells (hereinafter, also abbreviated as SCs) or neurolemmocytes are the principal glia cells of the peripheral nervous system. Glia cells function to support neurons and in the peripheral nervous system, include satellite cells, olfactory ensheathing cells, enteric glia cells, glia cells that reside at sensory nerve endings, such as the Pacinian corpuscle, and the like.

In myelinated axons, Schwann cells form the myelin sheath. The sheath is not continuous, and individual Schwann cells wrap around about 100 μm of an axon. The gaps between adjacent Schwann cells are called nodes of Ranvier. The vertebrate nervous system is insulated with the myelin sheath to maintain the membrane capacitance of the axon. The action potential jumps from node to node of the nodes of Ranvier. Through this process, conduction velocity increases up to 10 times, without an increase in axonal diameter, and energy may be saved. Schwann cells may be the analogues of the oligodendrocytes which play the same role in the central nervous system. However, unlike oligodendrocytes, Schwann cells form the myelin sheath in only one axon.

Charcot-Marie-Tooth (CMT) disease, which is a hereditary disease, is a disease in which the muscles of the limbs gradually shrink due to the abnormalities of Schwann cells forming the myelin sheath in the peripheral nervous system. Among types thereof, Charcot-Marie-Tooth type 1A (CMT1A) is one of the genetic diseases most frequently occurring in the peripheral nervous system, and there is such a big difference in genetic information between human and animal models for finding out the genetic causes of CMT1A and a solution to CMT1A with information obtained from animal models that there are problems in matching. CMT1A accounts for more than half of all CMT cases and about 70% of CMT1 cases, and the incidence of CMT is $\frac{1}{2,500}$. CMT1A exhibits pathological characteristics such as muscle weakness and loss, decreased reflexes, acroparesthesia, dysmelia, a reduction in nerve conduction viscosity (NCV), hypertrophic segmental demyelination, and remyelination which appears like onion bulbs.

Currently, there is no fundamental therapeutic agent or therapeutic method for diseases caused by the dysfunction of Schwann cells, such as CMT1A. There is only a method for partially reducing the aggravation of symptoms using physical therapy, orthopedic aids, and orthopedic surgery. Therefore, there is a great need for developing a fundamental therapeutic method for a disease caused by the dysfunction of Schwann cells.

SUMMARY

Technical Problem

To solve the problem, the present invention relates to an artificially manipulated SC function-controlling system, having an improved SC function-controlling effect. More specifically, the present invention relates to an artificially manipulated SC function-controlling factor and an SC function-controlling system (also referred to as an SC function-controlling modification system), which artificially controls an SC function and/or modifies the expression of the SC function-controlling factor.

The present invention provides a genetically manipulated or modified SC function-controlling factor for a specific purpose.

The present invention is intended to provide an artificially manipulated SC function-controlling system as an embodiment.

The present invention is intended to provide an artificially manipulated SC function-controlling factor modification system as an embodiment.

The present invention is intended to provide an artificially manipulated SC function-controlling factor and an expression product thereof as an embodiment.

The present invention is intended to provide a composition for manipulating a gene for the manipulation of an SC function-controlling factor and a method using the same as an embodiment.

The present invention is intended to provide a method for controlling an SC function as an embodiment.

The present invention is intended to provide a therapeutic or pharmaceutical composition for treating an SC dysfunction associated disease and various uses thereof as an embodiment.

The present invention is intended to provide SC function-controlling factors of artificially manipulated PMP22 and/or an expression product thereof as an embodiment.

The present invention is intended to provide a composition for gene manipulation for the artificial manipulation of SC function-controlling factors of PMP22 as an embodiment.

The present invention is intended to provide a therapeutic use of SC function-controlling factors of artificially manipulated PMP22 and/or the composition for gene manipulation for the artificial manipulation as an embodiment.

The present invention is intended to provide an additional use of SC function-controlling factors of artificially manipulated PMP22 and/or the composition for gene manipulation for the artificial manipulation as an embodiment.

Technical Solution

To solve the problem, the present invention relates to a system capable of artificially controlling an SC function, the system comprising: an artificially manipulated SC function-controlling factor for SC function control and/or the treatment or alleviation of an SC dysfunction associated disease and/or a composition capable of artificially manipulating the SC function-controlling factor.

The present invention provides an artificially manipulated SC function-controlling factor for a specific purpose.

The "SC function-controlling factor" refers to all elements directly participating in or indirectly affecting SC function control. In this case, the element may be DNA, RNA, a gene, a peptide, a polypeptide, or a protein. In addition, the SC function-controlling factor includes all elements directly participating in or indirectly affecting a function control of Schwann cells as well as glial cells and/or fibroblasts.

In embodiments, the element includes all various materials involved in unnatural, that is, artificially manipulated SC function control. For example, the element may be a genetically manipulated or modified gene or protein expressed in Schwann cells.

The SC function-controlling factor may suppress or inhibit the growth of Schwann cells, glial cells, and/or fibroblasts, or promote or increase the growth of Schwann cells.

The SC function-controlling factor may interrupt or arrest the progression of the cell cycle of Schwann cells, glial cells, and/or fibroblasts, or promote the progression of the cell cycle of Schwann cells.

The SC function-controlling factor may promote or suppress the differentiation of Schwann cells, glial cells, and/or fibroblasts.

The SC function-controlling factor may promote or suppress the death of Schwann cells, glial cells, and/or fibroblasts.

The SC function-controlling factor may help or interfere with the survival of peripheral nerve cells.

The SC function-controlling factor may help or interfere with the maintenance and signaling of peripheral nerve cells.

The SC function-controlling factor may control the myelin sheath formation of nerve cell axons.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

The SC function-controlling factor may be used for the alleviation and treatment of a disease due to dysfunctional or defective Schwann cells.

In an embodiment of the present invention, the SC function-controlling factor may be, for example, an artificially manipulated PMP22 gene.

In an embodiment of the present invention, the SC function-controlling factor may include one or more artificially manipulated genes. For example, the PMP22 gene may be artificially manipulated.

Therefore, an embodiment of the present invention provides a PMP22 gene which has a modification in a nucleic acid sequence as an artificially manipulated SC function-controlling factor.

The modification in a nucleic acid sequence may be non-limitedly, artificially manipulated by a guide nucleic acid-editor protein complex.

The term "guide nucleic acid-editor protein complex" refers to a complex formed through the interaction between a guide nucleic acid and an editor protein, and the nucleic acid-protein complex includes the guide nucleic acid and the editor protein.

The guide nucleic acid-editor protein complex may serve to modify a subject. The subject may be a target nucleic acid, a gene, a chromosome or a protein.

For example, the gene may be a SC function-controlling factor, artificially manipulated by a guide nucleic acid-editor protein complex,
wherein the SC function-controlling factor artificially manipulated includes one or more modifications of nucleic acids which is
at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the SC function-controlling factor or in a continuous 1 bp to 50 bp the base sequence region adjacent to the 5' end and/or 3' end thereof, or
a chemical modification of one or more nucleotides in a nucleic acid sequence constituting the SC function-controlling factor factor.

The modification of nucleic acids may occur in a promoter region of the gene.

The modification of nucleic acids may occur in an exon region of the gene.

The modification of nucleic acids may occur in an intron region of the gene.

The modification of nucleic acids may occur in an enhancer region of the gene.

The PAM sequence may be, for example, one or more of the following sequences (described in the 5' to 3' direction):
NGG (N is A, T, C or G);
NNNNRYAC (each of N is independently A, T, C or G, R is A or G, and Y is C or T); NNAGAAW (each of N is independently A, T, C or G, and W is A or T);
NNNNGATT (each of N is independently A, T, C or G);
NNGRR (T) (each of N is independently A, T, C or G, R is A or G); and
TTN (N is A, T, C or G).

The editor protein may be derived from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina,* Burkholderiales bacterium, *Polaromonas naphthalenivorans, Polaromonas* sp., Crocosphaera watsonii, Cyanothece sp., *Microcystis aeruginosa,* Synechococcus sp., *Acetohalobium arabaticum, Ammonifex degensii,* Caldicelulosiruptor becscii, Candidatus Desulforudis, *Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum,* Anabaena variabilis, Nodularia spumigena, Nostoc sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or Acaryochloris marina.

In one exemplary embodiment, the editor protein may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein. As an example, the editor protein may be a

*Streptococcus pyogenes*-derived Cas9 protein or a *Campylobacter jejuni*-derived Cas9 protein.

In Addition, in Another Embodiment,

The present invention provides a guide nucleic acid targeting a portion of a region comprising chromosome 17, U.S. Pat. Nos. 15,267,977 to 15,273,977 (regulatory region); chromosome 17, U.S. Pat. Nos. 15,229,777 to 15,265,326 (coding region); or chromosome 17, U.S. Pat. Nos. 15,268,191 to 15,437,045, chromosome 17, U.S. Pat. Nos. 15,239,833 to 15,258,667, or chromosome 17, U.S. Pat. Nos. 15,342,770 to 15,435,639 (non-coding region) in a nucleic acid sequence of a PMP22 gene.

In an exemplary embodiment, the present invention provides a guide nucleic acid, which is capable of forming a complementary bond with respect to target sequences of SEQ ID NOs: 1 to 66, for example, SEQ ID NOs: 1 to 8, 14 to 29 or 41 to 53 in the nucleic acid sequences of a PMP22 gene, respectively.

The guide nucleic acid may form a complementary bond with a part of nucleic acid sequences of a PMP22 gene. It may include 0 to 5, 0 to 4, 0 to 3, or 0 to 2 mismatches. As an exemplary example, the guide nucleic acid may be nucleotides forming a complementary bond with one or more of the target sequences of SEQ ID NOs: 1 to 66, for example, SEQ ID NOs: 1 to 8, 14 to 29 or 41 to 53, respectively.

For example, the present invention may provide one or more guide nucleic acids selected from the group as described below:

A guide nucleic acid capable of forming a complementary bond with respect to the target sequences of SEQ ID NOs: 1, 3, 25, 27, 28, 41, 44, 45 and 53 in the nucleic acid sequence of the PMP22 gene, respectively;

The guide nucleic acid may be non-limitedly 18 to 25 bp, 18 to 24 bp, 18 to 23 bp, 19 to 23 bp, or 20 to 23 bp nucleotides. It may create 0 to 5, 0 to 4, 0 to 3, or 0 to 2 mismatches.

In addition, the present invention provides a composition for gene manipulation, which may be employed in artificial manipulation of a SC function-controlling factor for a specific purpose.

In another embodiment, the composition for gene manipulation may include a guide nucleic acid-editor protein complex or a nucleic acid sequence encoding the same.

As an exemplary embodiment, the composition for gene manipulation may include:

(a) a guide nucleic acid targeting a portion of a region comprising chromosome 17, U.S. Pat. Nos. 15,267,977 to 15,273,977 (regulatory region); chromosome 17, U.S. Pat. Nos. 15,229,777 to 15,265,326 (coding region); or chromosome 17, U.S. Pat. Nos. 15,268,191 to 15,437,045, chromosome 17, U.S. Pat. Nos. 15,239,833 to 15,258,667, or chromosome 17, U.S. Pat. Nos. 15,342,770 to 15,435,639 (non-coding region) in a nucleic acid sequence of a PMP22 gene, or a nucleic acid sequence encoding the same; and (b) an editor protein forming a complex with the guide nucleic acid to cleave or modify a targeting site in a nucleic acid sequence of a PMP22 gene, or a nucleic acid sequence encoding the same.

In an exemplary embodiment, the composition for gene manipulation may include:

(a) a guide nucleic acid which is capable of forming a complementary bond with respect to the target sequences of SEQ ID NOs: 1 to 66, for example, SEQ ID NOs: 1 to 8, 14 to 29 or 41 to 53 in the nucleic acid sequences of a PMP22 gene, respectively, or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same.

In one exemplary embodiment, the guide nucleic acid may be a nucleic acid sequence which forms a complementary bond with respect to one or more of the target sequences of SEQ ID NOs: 1, 3, 25, 27, 28, 41, 44, 45 and 53 in the nucleic acid sequence of the PMP22 gene, respectively.

In one exemplary embodiment, the composition for gene manipulation may be a viral vector system.

The viral vector may include one or more selected from the group consisting of a retrovirus, a lentivirus, an adenovirus, an adeno-associated virus (AAV), a vaccinia virus, a poxvirus and a herpes simplex virus.

In still another exemplary embodiment, the present invention may provide a method for artificially manipulating cells, which includes:

(a) a guide nucleic acid targeting a portion of a region comprising chromosome 17, U.S. Pat. Nos. 15,267,977 to 15,273,977 (regulatory region); chromosome 17, U.S. Pat. Nos. 15,229,777 to 15,265,326 (coding region); or chromosome 17, U.S. Pat. Nos. 15,268,191 to 15,437,045, chromosome 17, U.S. Pat. Nos. 15,239,833 to 15,258,667, or chromosome 17, U.S. Pat. Nos. 15,342,770 to 15,435,639 (non-coding region) in a nucleic acid sequence of a PMP22 gene, or a nucleic acid sequence encoding the same; and (b) an editor protein forming a complex with the guide nucleic acid to cleave or modify a targeting site in a nucleic acid sequence of a PMP22 gene, or a nucleic acid sequence encoding the same.

In an exemplary embodiment, the present invention provides a method for artificially manipulating cells, which includes: introducing (a) a guide nucleic acid which is capable of forming a complementary bond with respect to the target sequences of SEQ ID NOS: 1 to 66, for example, SEQ ID NOs: 1 to 8. 14 to 29 or 41 to 53 in the nucleic acid sequences of a PMP22 gene, respectively, or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same to cells.

The guide nucleic acid and the editor protein may be present in one or more vectors in the form of a nucleic acid sequence, or may be present in a complex formed by coupling the guide nucleic acid with the editor protein.

The introduction may be performed in vivo or ex vivo.

The introduction may be performed by one or more methods selected from electroporation, liposomes, plasmids, viral vectors, nanoparticles and a protein translocation domain (PTD) fusion protein method.

The viral vector may be one or more selected from the group consisting of a retrovirus, a lentivirus, an adenovirus, an adeno-associated virus (AAV), a vaccinia virus, a poxvirus and a herpes simplex virus.

In another exemplary embodiment, the present invention provides a pharmaceutical composition for treating a SC dysfunction associated disease and/or SC function-controlling factor-associated disease.

The pharmaceutical composition may include a composition for gene manipulation which may be employed in artificial manipulation of a SC function-controlling factor.

The formulation of the composition for gene manipulation is the same as described above.

An embodiment provides a method for providing information on a sequence of a target position capable of being artificially manipulated in a subject through sequencing of a PMP22 gene.

Further, an embodiment provides a method for constructing a library by using information provided by the method.

An embodiment provides a kit for gene manipulation, comprising the following:
(a) a guide nucleic acid targeting a portion of a region comprising chromosome 17, U.S. Pat. Nos. 15,267,977 to 15,273,977 (regulatory region); chromosome 17, U.S. Pat. Nos. 15,229,777 to 15,265,326 (coding region); or chromosome 17, U.S. Pat. Nos. 15,268,191 to 15,437,045, chromosome 17, U.S. Pat. Nos. 15,239,833 to 15,258,667, or chromosome 17, U.S. Pat. Nos. 15,342,770 to 15,435,639 (non-coding region) in a nucleic acid sequence of a PMP22 gene, or a nucleic acid sequence encoding the same; and
(b) an editor protein forming a complex with the guide nucleic acid to cleave or modify a targeting site in a nucleic acid sequence of a PMP22 gene, or a nucleic acid sequence encoding the same.

In an exemplary embodiment, the present invention provides a kit for gene manipulation, which includes the following components:
(a) a guide nucleic acid capable of forming a complementary bond with respect to the target sequences of SEQ ID NOs: 1 to 66, for example, SEQ ID NOs: 1 to 8, 14 to 29 or 41 to 53 in the nucleic acid sequences of a PMP22 gene, respectively, or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same.

The gene of interest may be artificially manipulated using such a kit.

In one exemplary embodiment, the present invention may provide a composition for treating a SC dysfunction disorder, which includes:
a guide nucleic acid capable of forming a complementary bond with one or more target sequences in the nucleic acid sequences of the PMP22 gene, respectively, or a nucleic acid sequence encoding the same; and
an editor protein or a nucleic acid sequence encoding the same.

The target sequence may be a portion of a region comprising chromosome 17, U.S. Pat. Nos. 15,267,977 to 15,273,977 (regulatory region); chromosome 17, U.S. Pat. Nos. 15,229,777 to 15,265,326 (coding region); or chromosome 17, U.S. Pat. Nos. 15,268,191 to 15,437,045, chromosome 17, U.S. Pat. Nos. 15,239,833 to 15,258,667, or chromosome 17, U.S. Pat. Nos. 15,342,770 to 15,435,639 (non-coding region) in a nucleic acid sequence of a PMP22 gene The target sequences may be one or more sequences of SEQ ID NOs: 1 to 66, for example, SEQ ID NOs: 1 to 8, 14 to 29 or 41 to 53.

In one exemplary embodiment, a *Campylobacter jejuni*, a *Streptococcus pyogenes*-derived Cas9 protein may be employed as the editor protein.

In an example, the SC dysfunction disorder may be an SC function-controlling factor associated disease.

In an example, the SC function-controlling factor associated disease is Charcot-Marie-Tooth disease type 1A (CMT1A), Dejerine-Sottas disease (DSS), Congenital Hypomyelination Neuropathy (CHN), or Roussy-Levy syndrome (RLS).

In one exemplary embodiment, the present invention provides all aspects of uses of an artificially manipulated SC function-controlling factor or a composition for gene manipulation which is employed in artificial manipulation of the SC function-controlling factor for treating a disease in a target.

Targets for treatment may be mammals including primates such as humans, monkeys, etc., rodents such as mice, rats, etc., and the like.

Advantageous Effects

An artificially manipulated SC function-controlling factor and an SC function-controlling system whose functions are artificially modified by the same may be used for an effective therapeutic use of an SC dysfunction disorder, for example, an SC function-controlling factor associated disease such as Charcot-Marie-Tooth disease type 1A (CMT1A), Dejerine-Sottas disease (DSS), Congenital Hypomyelination Neuropathy (CHN), or Roussy-Levy syndrome (RLS). Through various in vivo mechanisms that SC function-controlling factors are involved in, the efficacy of an SC function-controlling system may be improved.

For example, the PMP22 gene may be used.

BRIEF DESCRIPTION OF THE DRAWINGS

FIG. 1 is a set of results illustrating an indel frequency due to SpCas9-sgRNA-mediated gene manipulation, and illustrates an indel frequency of each of (a) CDS, (b) TATA-box, and (c) Enhancer, into which a target site of sgRNA is divided.

FIG. 2 is a set of results illustrating an indel frequency due to CjCas9-sgRNA-mediated gene manipulation, and illustrates an indel frequency of each of (a) CDS, (b) TATA-box, and (c) Enhancer, into which a target site of sgRNA is divided.

FIG. 3 illustrates gene manipulation effects by SpCas9-sgRNA targeting controlling factors (regulatory elements) of a human PMP22 gene in Schwann-like cells.

FIG. 4 illustrates Frameshift mutation ratios induced by the SpCas9-sgRNAs targeting CDS of human PMP22

DETAILED DESCRIPTION

Figure 5:
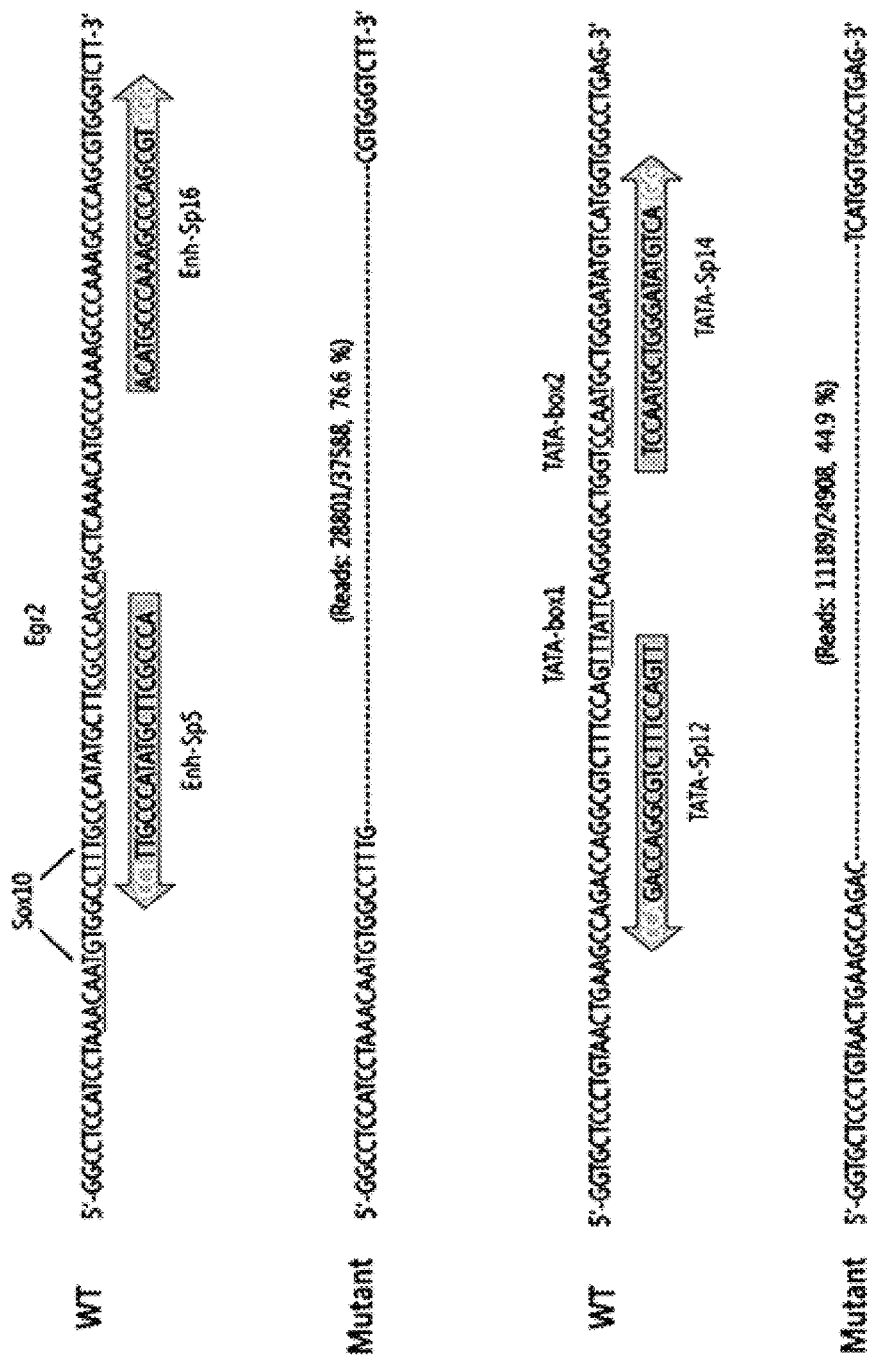
FIG. 5 illustrates Deletions of critical sites for regulatory elements of human PMP22 by the treatments of the dual sgRNAs. The wildtype sequences represent SEQ ID NOs: 202 and 206. The mutant sequences represent SEQ ID NOs: 205 and 209. Enh-Sp5 and Enh-Sp16 dual sgRNAs represent SEQ ID NOs: 203 and 204, respectively. TATA-Sp12 and TATA-Sp14 dual sgRNAs represent SEQ ID NOs: 207 and 208 respectively.

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limitive.

An aspect of the present invention relates to an artificially manipulated SC function-controlling system having an effect of alleviating or recovering from Schwann cell dysfunction.

Specifically, an aspect of the present invention relates to a configuration of various aspects capable of alleviating or treating an SC function-controlling factor expression disorder or Schwann cell dysfunction associated disease by artificially manipulating an SC function-controlling factor to regulate the expression of the SC function-controlling factor or recover from an abnormal function of Schwann cells. An aspect of the present invention includes an artificially expressed SC-function-controlling factor and/or an SC function-controlling factor whose functions are modified, a preparation method thereof, a composition comprising the same, a therapeutic use thereof, and the like.

Another aspect of the present invention relates to an additional system for controlling a third in vivo mechanism, concomitant with various functions of an artificially expressed SC function-controlling factor and/or an SC function-controlling factor whose functions are modified.

Specifically, another aspect of the present invention may control the corresponding mechanism by targeting not only a myelination function in which an artificially manipulated SC function-controlling factor is involved, but also a third in vivo function. Another aspect of the present invention includes an artificially expressed SC function-controlling factor and/or an SC function-controlling factor whose functions are modified, a preparation method thereof, a composition comprising the same, a therapeutic use thereof capable of alleviating or treating a disease associated with a third function, and the like.

[Sc Function]

An embodiment of the present invention relates to an improvement and modification of an SC function-controlling system.

The "SC function control" refers to an overall function control of an SC function factor, for example, Schwann cells, glial cells, and/or fibroblasts, which are affected by the function of a PMP22 gene, and herein, the function includes an entire development and growth process of the growth, differentiation, and death of Schwann cells, glial cells, and/or fibroblasts, and also includes all functions such as the survival and maintenance of peripheral nerve cells of Schwann cells and the myelin sheath formation (myelination) on the axon. Further, the SC function control includes an overall function of Schwann cells, glial cells, and/or fibroblasts, for example, the control of the entire development and growth process ranging from cellular growth and differentiation to the death of cells.

The SC function control includes the control of all mechanisms that suppress or inhibit the growth of Schwann cells, glial cells, and/or fibroblasts, or promote or increase the growth of Schwann cells, glial cells, and/or fibroblasts.

The SC function control includes the control of all mechanisms that interrupt or arrest the progression of the cell cycle of Schwann cells, glial cells, and/or fibroblasts, or promote the progression of the cell cycle of Schwann cells, glial cells, and/or fibroblasts.

The SC function control includes the control of all mechanisms that promote or suppress the differentiation of Schwann cells, glial cells, and/or fibroblasts.

The SC function control includes the control of all mechanisms, such as the control of a mechanism that promotes or suppresses the death of Schwann cells, glial cells, and/or fibroblasts, for example, apoptosis.

In addition, the SC function control includes the control all mechanisms that help or interfere with the survival of peripheral nerve cells.

The SC function control includes all mechanisms that help or interfere with the maintenance and signaling of peripheral nerve cells.

The SC function control includes the control of all mechanisms that are involved in the myelin sheath formation of the axon of nerve cells.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

Furthermore, the SC function control includes the control of all mechanisms that suppress or inhibit the growth of fibroblasts or glial cells, or promote or increase the growth of fibroblasts or glial cells.

The SC function control includes the control of all mechanisms that are involved in the activity of fibroblasts or glial cells.

In an embodiment, the SC function control may be involved in the treatment or alleviation of a disease caused by duplication of PMP22.

For example, the SC function-controlling factor may be involved in the treatment or alleviation of a disease caused by, for example, a modification in expression (including mutation) of PMP22.

In an embodiment, the SC function control may control the myelin sheath formation.

For example, since the SC function-controlling factor, for example, the overexpression of PMP22 has a characteristic of causing a neuropathy by destabilizing the myelin sheath which leads to interference with the maintenance and formation of the myelin sheath, the SC function control through the control of the expression of the SC function-controlling factor may control the myelin sheath formation.

In another embodiment, the SC function control may control the differentiation of Schwann cells.

For example, since the SC function-controlling factor, for example, PMP22 has a characteristic of increasing expression during the differentiation of Schwann cells, the SC function control through the control of the expression of the SC function-controlling factor may control the differentiation of Schwann cells.

In an embodiment, the SC function control may control the signaling of nerve cells.

For example, since the SC function-controlling factor, for example, the overexpression of PMP22 has a characteristic of decreasing the signaling of nerve cells, that is, the conduction velocity, by destabilizing the myelin sheath which leads to interference with the maintenance and formation of the myelin sheath, the SC function control through the control of the expression of the SC function-controlling factor may control the myelin sheath formation.

SC Function-Controlling Factor

An embodiment of the present invention is an artificially manipulated or modified SC function-controlling factor.

The "SC function-controlling factor" refers to all elements directly participating in or indirectly affecting the SC function control. In this case, the element may be DNA, RNA, a gene, a peptide, a polypeptide, or a protein.

In embodiments, the element includes all various materials involved in unnatural, that is, artificially manipulated SC function control. For example, the element may be a genetically manipulated or modified gene or protein expressed in Schwann cells.

The term "artificially manipulated" refers to an artificially modified state rather than a state that occurs in the natural state and is present as it is.

The term "genetically manipulated" refers to a case where a manipulation of subjecting a biologically or non-biologically derived material mentioned in the present invention to artificially genetic modification is performed, and may be, for example, a gene and/or a gene product (a polypeptide, a protein, and the like), in which the genome is artificially modified for a specific purpose.

As a preferred example, the present invention provides a genetically manipulated or modified SC function-controlling factor for a specific purpose.

Hereinafter, a gene or protein having a listed function may have not only one type of SC function-controlling associated function, but also a plurality of functions. Further, the present invention may provide two or more SC function-controlling associated functions and factors, if necessary.

The SC function-controlling factor may suppress or inhibit the growth of Schwann cells, or promote or increase the growth of Schwann cells.

The SC function-controlling factor may interrupt or arrest the progression of the cell cycle of Schwann cells, or promote the progression of the cell cycle of Schwann cells.

The SC function-controlling factor may promote or suppress the differentiation of Schwann cells.

The SC function-controlling factor may promote or suppress the death of Schwann cells.

The SC function-controlling factor may help or interfere with the survival of peripheral nerve cells.

The SC function-controlling factor may help or interfere with the maintenance and signaling of peripheral nerve cells.

The SC function-controlling factor may control the myelin sheath formation of nerve cell axons.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

The SC function-controlling factor may be used for the alleviation and treatment of a disease due to dysfunctional or defective Schwann cells.

Further, the SC function-controlling factor may control all mechanisms that suppress or inhibit the growth of fibroblasts or glial cells, or promote or increase the growth of fibroblasts or glial cells.

The SC function-controlling factor may control all mechanisms that are involved in the activity of fibroblasts or glial cells.

In embodiments, the SC function-controlling factor may be PMP22.

In any embodiment, the SC function-controlling factor may be PMP22.

A peripheral myelin protein 22 (PMP22) gene refers to a gene (full-length DNA, cDNA, or mRNA) encoding the PMP22 protein also referred to as GAS3 or GAS-3. In an example, the PMP22 gene may be one or more selected from the group consisting of the following, but is not limited thereto: a gene encoding human PMP22 (for example, NCBI Accession No. NP_000295.1, NP_001268384.1, NP_001268385.1, NP_001317072.1, NP_696996.1, NP_696997.1, and the like), for example, a PMP22 gene represented by NCBI Accession No. NM_000304.3, NM_001281455.1, NM_001281456.1, NM_001330143.1, NM_153321.2, NM_153322.2, and the like.

The peripheral myelin protein 22 (PMP22) is a 22 kDa of transmembrane glycoprotein of myelin, and the PMP22 is expressed in Schwann cells forming the myelin of the peripheral nerve system, and plays an important role in the formation and maintenance of compact myelin. The PMP22 gene is mapped to human chromosome 17p11.2-p12, and encodes production of the PMP22 glycoprotein. The modification of PMP22 gene expression is associated with hereditary demyelinating peripheral nerve neuropathy, and causes the abnormal synthesis and function of myelin sheaths. The increased expression of PMP22 due to the duplication of PMP22 is the most likely mechanism that causes a disease.

The point mutation or frameshift mutation of PMP22 causes hereditary neuropathy with liability to pressure palsy (HNPP), and the missense mutation causes various types of CMT called Dejerine.Sottas syndrome (DSS) and congenital hypomyelinating neuropathy (CHN). Further, the Roussy-Levy syndrome (RLS) is caused by duplication of PMP22, and is generally considered as a phenotype variant of CMT1A.

The SC function-controlling factor may be derived from a mammal including a primate such as a human and a monkey, a rodent such as a rat and a mouse, and the like.

Gene information may be obtained from a publicly-known database such as the GenBank of the National Center for Biotechnology Information (NCBI).

As an embodiment of the present invention, the SC function-controlling factor, for example, PMP22 may be an artificially manipulated SC function-controlling factor.

In any embodiment, the artificially manipulated SC function-controlling factor may be genetically manipulated.

The gene manipulation or modification may be obtained by artificially causing insertions, deletions, substitutions, or inversion mutations in a partial or entire region of the genomic sequence of a wild type gene. In addition, the gene manipulation or modification may also be obtained by fusing two or more manipulated or modified genes.

For example, the gene is inactivated by the gene manipulation or modification, such that a protein encoded by the gene may not be expressed in the form of a protein having an inherent function.

For example, the gene may be further activated by the gene manipulation or modification, such that a protein encoded by the gene is to be expressed in the form of a protein having an improved function, compared to the inherent function. As an example, when a function of a protein encoded by a specific gene is A, a function of a protein expressed by a manipulated gene may be totally different from A, or may have an additional function (A+B) including A.

For example, a fusion of two or more proteins may be expressed using two or more genes having different or complementary functions due to the gene manipulation or modification.

For example, two or more proteins may be expressed separately or independently in cells by using two or more genes having different or complementary functions due to the gene manipulation or modification.

The manipulated SC function-controlling factor may suppress or inhibit the growth of Schwann cells, or promote or increase the growth of Schwann cells.

The manipulated SC function-controlling factor may interrupt or arrest the progression of the cell cycle of Schwann cells, or promote the progression of the cell cycle of Schwann cells.

The manipulated SC function-controlling factor may promote or suppress the differentiation of Schwann cells.

The manipulated SC function-controlling factor may promote or suppress the death of Schwann cells.

The manipulated SC function-controlling factor may help or interfere with the survival of peripheral nerve cells.

The manipulated SC function-controlling factor may help or interfere with the maintenance and signaling of peripheral nerve cells.

The manipulated SC function-controlling factor may control the myelin sheath formation of nerve cell axons.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

The manipulated SC function-controlling factor may be used for the alleviation and treatment of a disease due to dysfunctional or defective Schwann cells.

Further, the manipulated SC function-controlling factor may control all mechanisms that suppress or inhibit the growth of fibroblasts or glial cells, or promote or increase the growth of fibroblasts or glial cells.

The manipulated SC function-controlling factor may control all mechanisms that are involved in the activity of fibroblasts or glial cells.

The manipulation includes all structural or functional modifications of the SC function-controlling factor.

The structural modification of the SC function-controlling factor includes all modifications that are not the same as the wild type present in a natural state.

For example, when the SC function-controlling factor is a DNA or RNA gene, the structural modification may be a structural modification in which one or more nucleotides are lost.

The structural modification may be a structural modification in which one or more nucleotides are inserted.

In this case, the inserted nucleotide includes all nucleotides introduced from a subject including the SC function-controlling factor or outside of the subject.

The structural modification may be a structural modification in which one or more nucleotides are substituted.

The structural modification may include a chemical modification of one or more nucleotides.

In this case, the chemical modification includes all of additions, removals, or substitutions of functional groups.

As another example, when the SC function-controlling factor is a peptide, a polypeptide, or a protein, the structural modification may be a structural modification in which one or more amino acids are lost.

The structural modification may be a structural modification in which one or more amino acids are inserted.

In this case, the inserted amino acid includes all amino acids introduced from a subject including the SC function-controlling factor or outside of the subject.

The structural modification may be a structural modification in which one or more amino acids are substituted.

The structural modification may include a chemical modification of one or more amino acids.

In this case, the chemical modification includes all of additions, removals, or substitutions of functional groups.

The structural modification may be a structural modification in which a part or all of another peptide, polypeptide, or protein is attached.

In this case, the other peptide, polypeptide, or protein may be an SC function-controlling factor, or may be a peptide, a polypeptide, or a protein, which performs another function.

The functional modification of the SC function-controlling factor includes all modifications having an improved function or a deteriorated function, compared to the wild type present in a natural state, or having a third different function.

For example, when the SC function-controlling factor is a peptide, a polypeptide, or a protein, the functional modification may be a mutation of the SC function-controlling factor.

In this case, the mutation may be a mutation in which the function of the SC function-controlling factor is improved or inhibited.

The functional modification may be a functional modification in which the function of the SC function-controlling factor is added.

In this case, the added function may be the same function or different functions. Further, the SC function-controlling factor to which the function is added may be fused with other peptides, polypeptides, or proteins.

The functional modification may be an increase in function due to an increase in expression of the SC function-controlling factor.

The functional modification may be a decrease in function due to a decrease in expression of the SC function-controlling factor.

The functional modification may be a recovery of the function due to a decrease in expression of the SC function-controlling factor.

As an embodiment, the SC function-controlling factor may be induced by one or more of the following:
  all or partial deletions of the SC function-controlling factor, that is, a gene to be manipulated (hereinafter, referred to as a target gene), for example, deletion of a 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotide of the target gene,
  substitution of a 1 bp or longer nucleotide, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotide of the target gene with a nucleotide different from a wild type, and
  insertion of a 1 bp or more nucleotide, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotide (each independently selected from A, T, C and G) into any position of the target gene.

A modified part of the target gene ('target region') may be a continuous base sequence site of 1 bp or more, 3 bp or more, 5 bp or more, 7 bp or more, 10 bp or more, 12 bp or more, 15 bp or more, 17 bp or more, or 20 bp or more, for example, 1 bp to 30 bp, 3 bp to 30 bp, 5 bp to 30 bp, 7 bp to 30 bp, 10 bp to 30 bp, 12 bp to 30 bp, 15 bp to 30 bp, 17 bp to 30 bp, 20 bp to 30 bp, 1 bp to 27 bp, 3 bp to 27 bp, 5 bp to 27 bp, 7 bp to 27 bp, 10 bp to 27 bp, 12 bp to 27 bp, 15 bp to 27 bp, 17 bp to 27 bp, 20 bp to 27 bp, 1 bp to 25 bp, 3 bp to 25 bp, 5 bp to 25 bp, 7 bp to 25 bp, 10 bp to 25 bp, 12 bp to 25 bp, 15 bp to 25 bp, 17 bp to 25 bp, 20 bp to 25 bp, 1 bp to 23 bp, 3 bp to 23 bp, 5 bp to 23 bp, 7 bp to 23 bp, 10 bp to 23 bp, 12 bp to 23 bp, 15 bp to 23 bp, 17 bp to 23 bp, 20 bp to 23 bp, 1 bp to 20 bp, 3 bp to 20 bp, 5 bp to 20 bp, 7 bp to 20 bp, 10 bp to 20 bp, 12 bp to 20 bp, 15 bp to 20 bp, 17 bp to 20 bp, 21 bp to 25 bp, 18 bp to 22 bp, or 21 bp to 23 bp of the gene.

Meanwhile, a different embodiment of the present invention relates to an additional system for controlling a third in vivo mechanism, concomitant with various functions of the above-described SC function-controlling factors whose functions are artificially modified.

As an embodiment, PMP22 may be involved in control of the third in vivo mechanism.

Since many studies have confirmed that the expression of PMP22 is increased in a tumor cell, which means that the expression of PMP22 affects the proliferation-associated mechanism of tumor cells in various cancer diseases, artificially manipulated PMP22 may suppress or inhibit the proliferation of cells of various tumors (for example, breast cancer, gastric cancer, pancreatic cancer, and the like), for example, by inhibition of the expression of PMP22 or manipulation to inactivate PMP22. In addition, it is possible to suppress or inhibit the progression or metastasis of various cancer diseases or to provide an effect of alleviating or treating cancer diseases, by artificially manipulated PMP22.

As described above, artificially manipulated exemplary factors of the present invention may control the SC function, and may control the corresponding mechanism by targeting a third in vivo function. Embodiments of the present invention includes an SC function-controlling factor whose functions are artificially modified, a preparation method thereof, a composition comprising the same, a therapeutic use thereof capable of alleviating or treating a disease associated with a third function, and the like.

[SC Function-Controlling System]

An embodiment of the present invention is an SC function-controlling system which controls an SC function by artificially manipulating an SC function-controlling factor.

The "SC function-controlling system" of the present invention is a term including all phenomena affecting the promotion, increase, inhibition, suppression and/or normal function recovery of SC functions by expression change and/or function change of an artificially manipulated SC function-controlling factor, and includes all materials, compositions, methods, and uses, which are directly or indirectly involved in the SC function-controlling system.

The respective elements constituting the SC function-controlling system are also collectively referred to as "SC function-controlling elements".

Further, the SC function-controlling system includes an SC function-controlling modification system whose expressions are modified and/or functions are modified by artificially manipulating an SC function-controlling factor.

The "SC function-controlling factor modification system" collectively refers to the transcription of an SC function-controlling factor present in the genome of a subject or introduced from the outside, modification of the expression of an overall SC function-controlling factor expressed from transcribed genetic information (for example, mRNA) as a protein, that is, a process such as a decrease in expression, an increase in expression, and an maintenance of expression, and a product thereof.

In addition, the "SC function-controlling factor modification system" also includes an overall process of interfering with the expression and/or function of a normal SC function-controlling factor by the mutation of the SC function-controlling factor, or expressing a normal SC function-controlling factor such as the expression of a mutation of the normal SC function-controlling factor, an abnormal SC function-controlling factor, and an artificially modified SC function-controlling factor, and a product thereof.

As an embodiment, the system of the present invention includes an SC function-controlling factor, that is a PMP22 modification system, as an SC function-controlling element, and in this case, the SC function-controlling factor, that is, PMP22 includes an artificially manipulated SC function-controlling factor.

The "PMP22 modification system" collectively refers to the transcription of a PMP22 gene present in the genome of a subject or introduced from the outside, modification of the expression of an overall PMP22 expressed from transcribed genetic information (for example, mRNA) as a protein, that is, a process such as a decrease in expression, an increase in expression, and an maintenance of expression, and a product thereof.

In addition, the "PMP22 modification system" also includes an overall process of interfering with the expression and/or function of normal PMP22 by the mutation of the PMP22, or expressing normal PMP22 such as the expression of a mutation of the PMP22, abnormal PMP22, and artificially modified PMP22, and a product thereof.

In a PMP22 modification system, by artificially manipulated PMP22, in any embodiment, the expression of PMP22 may be increased or promoted.

In any embodiment, the expression of PMP22 may be inhibited or suppressed.

For example, when a PMP22 gene is duplicated and overexpressed, the expression may be suppressed or decreased to a normal expression level by artificially manipulated PMP22.

In any embodiment, the function of PMP22 may be enhanced or promoted.

In any embodiment, the function of PMP22 may be degraded or suppressed.

Further, in a PMP22 modification system, by artificially manipulated PMP22, in any embodiment, the growth of Schwann cells may be suppressed or inhibited, or the growth of Schwann cells may be promoted or increased.

In any embodiment, the progression of the cell cycle of Schwann cells may be interrupted or arrested, or the progression of the cell cycle of Schwann cells may be promoted.

In any embodiment, the differentiation of Schwann cells may be promoted or suppressed.

In any embodiment, the death of Schwann cells may be promoted or suppressed.

In any embodiment, the survival of peripheral nerve cells may be helped or interfered with.

In any embodiment, the maintenance and signaling of peripheral nerve cells may be helped or interfered with.

In any embodiment, the myelin sheath formation of nerve cell axons may be controlled.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

In any embodiment, it is possible to be used for the alleviation and treatment of a disease due to dysfunctional or defective Schwann cells.

In an embodiment, it is possible to control all mechanisms that suppress or inhibit the growth of fibroblasts or glial cells, or promote or increase the growth of fibroblasts or glial cells.

In any embodiment, it is possible to control all mechanisms that are involved in the activity of fibroblasts or glial cells.

In any embodiment, the corresponding mechanism may be controlled by targeting a third in vivo function in which PMP22 is involved.

In embodiments, the SC function-controlling system of the present invention includes a composition for manipulating an SC function-controlling factor as an SC function-controlling element.

In embodiments, the SC function-controlling factor modification system of the present invention includes a composition for manipulating an SC function-controlling factor.

The composition for manipulation may be a composition capable of artificially manipulating an SC function-controlling factor, preferably, a composition for gene manipulation.

Hereinafter, the composition for gene manipulation will be described.

Composition for Manipulating SC Function-Controlling Factor

The manipulation or modification of a material which is involved in the SC function-controlling factor and the SC function-controlling system (including the SC function-controlling factor modification system) of the present invention may be achieved preferably by gene manipulation.

In an aspect, a composition and a method which manipulate a gene may be provided by targeting a part or all of a regulatory region, a non-coding region, or a coding region of an SC function-controlling factor.

For the composition and the method, in embodiments, one or more of SC function-controlling genes which are involved in the formation of a target SC function-controlling system (including an SC function-controlling factor modification system) may be manipulated or modified for the formation of the target SC function-controlling system. The manipulation or modification may be achieved through the modification of a nucleic acid constituting a gene. As manipulation results, all forms of knockdown, knockout, and knock in are included.

In embodiments, a part or all of a regulatory region, a non-coding region, or a coding region may be used as a target.

In any embodiment, a regulatory region among nucleic acids constituting the SC function-controlling gene may be used as a manipulation target.

For example, a partial or entire sequence such as a proximal promoter, an enhancer, a TATA box, and a regulatory element of an initiator may be used as a target. As a specific example, a partial or entire sequence of Promoter, TATA Box, CAAT Box, Initiation Site, Termination Site, Donor Splice Site, Acceptor Splice Site, Poly A Site, Enhancer, 3' Untranslated Region (UTR), 5' UTR, Attenuator, and GC Box may be used as a target.

In any embodiment, an enhancer site (for example, EGR2-, SOX10- or TEAD1-binding site) or a distal enhancer site (distal enhancer region) may be targeted among the nucleic acid sequences constituting the SC function-controlling gene.

In any embodiment, a coding region among nucleic acids constituting the SC function-controlling gene may be used as a manipulation target.

For example, an intron or exon sequence may be used as a target. In addition, a coding sequence, for example, a coding region, an initial coding region may be targeted for the change of expression and knockout.

In embodiments, the modification of nucleic acids may be substitutions, deletions, and/or insertions of 1 bp or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In embodiments, for the knockout of one or more SC function-controlling genes, elimination of expression of one or more of the genes, or knockouts of one, two, or three alleles, the above-described region may be targeted such that one or more SC function-controlling genes contain a deletion or mutation.

In exemplary embodiments, the knockdown of a gene may be used to decrease the expression of undesired alleles or transcriptomes.

In embodiments, the knockdown of a gene may be used to change an SC function-controlling gene affecting the functions of Schwann cells by targeting a part or all of a regulatory region, a non-coding region, or a coding region.

In embodiments, the activity of an SC function-controlling gene may be controlled, for example, activated or inactivated by a change of nucleic acids of the gene. Further, the functions of Schwann cells may be activated or inactivated by the change of nucleic acids of the gene.

In embodiments, the modification of nucleic acids of the gene may catalyze cleavage of a single strand or double strands, that is, breaks of nucleic acid strands at a specific site in the targeted gene by a guide nucleic acid-editor protein complex, resulting in inactivation of the targeted gene.

In embodiments, the nucleic acid strand breaks may be repaired through a mechanism such as homologous recombination or non-homologous end joining (NHEJ).

In this case, when the NHEJ mechanism takes place, a change in a DNA sequence may be induced at the cleavage site, resulting in inactivation of the gene. The repair by NHEJ may cause substitutions, insertions or deletions of a short gene fragment, and may be used in the induction of the corresponding gene knockouts or knockdown. Further, the functions of Schwann cells and/or an action mechanism thereof may be affected by the induction of the knockouts or knockdown of the SC function-controlling gene.

In another aspect, the present invention provides a composition for manipulating an SC function-controlling factor.

The composition for manipulation may be a composition capable of artificially manipulating an SC function-controlling factor, preferably, a composition for gene manipulation.

The composition may be employed for gene manipulation for one or more of SC function-controlling genes which are involved in the formation of a target SC function-controlling system (including an SC function-controlling factor modification system) for the formation of the target SC function-controlling system.

The gene manipulation may be performed in consideration of a gene expression controlling process.

In exemplary embodiments, the gene manipulation may be performed by selecting a suitable manipulation means for each step of transcription-, RNA processing-, RNA transporting-, RNA degradation-, translation-, and protein modification-controlling steps.

In embodiments, small RNA (sRNA) disrupts mRNA or reduces stability thereof using RNA interference (RNAi) or RNA silencing, and in some cases, breaks up mRNA to interfere with the delivery of protein synthesis information, resulting in control of the expression of genetic information.

The gene manipulation may be performed by modification of nucleic acids constituting an SC function-controlling factor. As manipulation results, all forms of knockdown, knockout, and knock in are included.

In any embodiment, the modification of nucleic acids may be substitutions, deletions, and/or insertions of 1 bp or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In any embodiment, for the knockout of one or more SC function-controlling factors, elimination of expression of one or more of the factors, or knockouts of one, two, or three alleles, the gene may be manipulated such that one or more SC function-controlling factors contain a deletion or mutation.

In any embodiment, knockdown of the SC function-controlling factor may be used to decrease the expression of undesired alleles or transcriptomes.

In any embodiment, the modification of nucleic acids may be the insertion of one or more nucleic acid fragments or genes. In this case, the nucleic acid fragment may be a nucleic acid sequence consisting of one or more nucleotides, and a length of the nucleic acid fragment may be 1 to 40 bp, 1 to 50 bp, 1 to 60 bp, 1 to 70 bp, 1 to 80 bp, 1 to 90 bp, 1 to 100 bp, 1 to 500 bp, or 1 to 1,000 bp. In this case, the inserted gene may be one of the SC function-controlling factors, or a gene having a different function.

In embodiments, the modification of nucleic acids may employ a wild type or variant enzyme which is capable of catalyzing hydrolysis (cleavage) of bonds between nucleic acids in a DNA or RNA molecule, preferably, a DNA molecule. The modification of nucleic acids may employ a guide nucleic acid-editor protein complex.

For example, the gene may be manipulated using one or more nucleases selected from the group consisting of a meganuclease, a zinc finger nuclease, CRISPR/Cas9 (Cas9 protein), CRISPR-Cpf1 (Cpf1 protein), and a TALE-nuclease, thereby controlling the expression of genetic information.

In any embodiment, the gene manipulation may be mediated by nonhomologous end joining (NHEJ) or homology-directed repair (HDR) using a guide nucleic acid-editor protein complex, for example, a CRISPR/Cas system, but is not limited thereto.

In this case, when the NHEJ mechanism takes place, a change in a DNA sequence may be induced at the cleavage site, resulting in inactivation of the gene or inhibition of expression thereof. Repair by NHEJ may cause substitutions, insertions or deletions of a short gene fragment, and may be used in the induction of the corresponding gene knockout or knockdown.

In another aspect, the present invention may provide the gene manipulation site.

In embodiments, when the gene is changed by a NHEJ-mediated change, the gene manipulation site refers to a site in the gene, causing the decrease or elimination of expression of an SC function-controlling gene product.

For example,
the site may be in an initial coding region.
The site may be in a promoter sequence.
The site may be in an enhancer sequence.
The site may be in a specific intron sequence.
The site may be in a specific exon sequence.

As an embodiment, the composition for manipulating an SC function-controlling factor may target a PMP22 gene which affects the functions of Schwann cells as a manipulation subject.

Examples of target sites, that is, target sequences for sites at which gene manipulation occurs or which are recognized for gene manipulation are summarized in Table 1, Table 2, Table 3, Table 4, Table 5, Table 6, and Table 7.

The target sequence may target one or more genes.

The target sequence may simultaneously target two or more genes. In this case, the two or more genes may be homologous genes or heterologous genes.

The gene may contain one or more target sequences.

The gene may be simultaneously targeted at two or more target sequences.

The gene may be changed in the position and number of gene manipulations depending on the number of target sequences.

The gene manipulation may be designed in various ways depending on the number and positions of the target sequences.

The gene manipulation may simultaneously occur in two or more target sequences. In this case, the two or more target sequences may be present in the homologous gene or heterologous gene.

The gene manipulation may be simultaneously performed with respect to the two or more genes. In this case, the two or more genes may be homologous genes or heterologous genes.

Hereinafter, examples of target sequences which may be used in an embodiment of the present invention are shown in the following tables:

Table 1. Target sequence for SpCas9 with respect to a coding sequence of PMP22 gene Table 2. Target sequence for CjCas9 with respect to a coding sequence of PMP22 gene Table 3. Target sequence for SpCas9 with respect to a promoter sequence of PMP22 gene Table 4. Target sequence for CjCas9 with respect to a promoter sequence of PMP22 gene Table 5. Target sequence for SpCas9 with respect to an enhancer sequence of PMP22 gene Table 6. Target sequence for CjCas9 with respect to an enhancer sequence of PMP22 gene Table 7. Target sequence for SpCas9 with respect to distal enhancer regions B and C of PMP22 gene

TABLE 1

| Gene | No. | Exon | Target sequence (5' to 3') | sgRNAs |
|---|---|---|---|---|
| PMP22 | 1 | 2 | CGATGATACTCAGCAACAGG (SEQ ID NO: 1) | sgRNA_CDS_Sp#1 |
| PMP22 | 2 | 2 | GGACGATGATACTCAGCAAC (SEQ ID NO: 2) | sgRNA_CDS_Sp#2 |
| PMP22 | 3 | 3 | ATGGACACGCAACTGATCTC (SEQ ID NO: 3) | sgRNA_CDS_Sp#3 |
| PMP22 | 4 | 4 | GATGATCGACAGGATCATGG (SEQ ID NO: 4) | sgRNA_CDS_Sp#4 |
| PMP22 | 5 | 4 | GAAGATGATCGACAGGATCA (SEQ ID NO: 5) | sgRNA_CDS_Sp#5 |
| PMP22 | 6 | 4 | AACTCTTCACCCTCACCAAG (SEQ ID NO: 6) | sgRNA_CDS_Sp#6 |
| PMP22 | 7 | 4 | AAAACCTGCCCCCCTTGGTG (SEQ ID NO: 7) | sgRNA_CDS_Sp#7 |
| PMP22 | 8 | 4 | GGAATCTTCCAAATTCTTGC (SEQ ID NO: 8) | sgRNA_CDS_Sp#8 |

TABLE 2

| Gene | No. | Exon | Target sequence (5' to 3') | sgRNAs |
|---|---|---|---|---|
| PMP22 | 1 | 2 | GATCGTGGAGACGAACAGCAGC (SEQ ID NO: 9) | sgRNA_CDS_Cj#1 |
| PMP22 | 2 | 2 | GCTGACGATCGTGGAGACGAAC (SEQ ID NO: 10) | sgRNA_CDS_Cj#2 |
| PMP22 | 3 | 3 | CGCAACTGATCTCTGGCAGAAC (SEQ ID NO: 11) | sgRNA_CDS_Cj#3 |
| PMP22 | 4 | 4 | GTGCGTGATGAGTGCTGCGGCC (SEQ ID NO: 12) | sgRNA_CDS_Cj#4 |
| PMP22 | 5 | 4 | GTGTAGATGGCCGCAGCACTCA (SEQ ID NO: 13) | sgRNA_CDS_Cj#5 |

TABLE 3

| Gene | No. | Target sequence (5' to 3') | sgRNAs |
|---|---|---|---|
| PMP22 | 1 | GGACCAGCCCCTGAATAAAC (SEQ ID NO: 14) | sgRNA_TATA_Sp#1 |
| PMP22 | 2 | GGCGTCTTTCCAGTTTATTC (SEQ ID NO: 15) | sgRNA_TATA_Sp#2 |
| PMP22 | 3 | GCGTCTTTCCAGTTTATTCA (SEQ ID NO: 16) | sgRNA_TATA_Sp#3 |
| PMP22 | 4 | CGTCTTTCCAGTTTATTCAG (SEQ ID NO: 17) | sgRNA_TATA_Sp#4 |
| PMP22 | 5 | TTCAGGGGCTGGTCCAATGC (SEQ ID NO: 18) | sgRNA_TATA_Sp#5 |
| PMP22 | 6 | TCAGGGGCTGGTCCAATGCT (SEQ ID NO: 19) | sgRNA_TATA_Sp#6 |
| PMP22 | 7 | ACCATGACATATCCCAGCAT (SEQ ID NO: 20) | sgRNA_TATA_Sp#7 |
| PMP22 | 8 | TTTCCAGTTTATTCAGGGGC (SEQ ID NO: 21) | sgRNA_TATA_Sp#8 |
| PMP22 | 9 | CAGTTACAGGGAGCACCACC (SEQ ID NO: 22) | sgRNA_TATA_Sp#9 |
| PMP22 | 10 | CTGGTCTGGCTTCAGTTACA (SEQ ID NO: 23) | sgRNA_TATA_Sp#10 |
| PMP22 | 11 | CCTGGTCTGGCTTCAGTTAC (SEQ ID NO: 24) | sgRNA_TATA_Sp#11 |
| PMP22 | 12 | AACTGGAAAGACGCCTGGTC (SEQ ID NO: 25) | sgRNA_TATA_Sp#12 |
| PMP22 | 13 | GAATAAACTGGAAAGACGCC (SEQ ID NO: 26) | sgRNA_TATA_Sp#13 |
| PMP22 | 14 | TCCAATGCTGGGATATGTCA (SEQ ID NO: 27) | sgRNA_TATA_Sp#14 |
| PMP22 | 15 | AATGCTGGGATATGTCATGG (SEQ ID NO: 28) | sgRNA_TATA_Sp#15 |
| PMP22 | 16 | ATAGAGGCTGAGAACCTCTC (SEQ ID NO: 29) | sgRNA_TATA_Sp#16 |

TABLE 4

| Gene | No. | Target sequence (5' to 3') | sgRNAs |
|---|---|---|---|
| PMP22 | 1 | GCCCTCTGAATCTCCAGTCAAT (SEQ ID NO: 30) | sgRNA_TATA_Cj#1 |
| PMP22 | 2 | AATCTCCAGTCAATTCCAACAC (SEQ ID NO: 31) | sgRNA_TATA_Cj#2 |
| PMP22 | 3 | AATTAGGCAATTCTTGTAAAGC (SEQ ID NO: 32) | sgRNA_TATA_Cj#3 |
| PMP22 | 4 | TTAGGCAATTCTTGTAAAGCAT (SEQ ID NO: 33) | sgRNA_TATA_Cj#4 |
| PMP22 | 5 | AAAGCATAGGCACACATCACCC (SEQ ID NO: 34) | sgRNA_TATA_Cj#5 |
| PMP22 | 6 | GCCTGGTCTGGCTTCAGTTACA (SEQ ID NO: 35) | sgRNA_TATA_Cj#6 |
| PMP22 | 7 | GTGTCCAACTTTGTTTGCTTTC (SEQ ID NO: 36) | sgRNA_TATA_Cj#7 |
| PMP22 | 8 | GTATTCTGGAAAGCAAACAAAG (SEQ ID NO: 37) | sgRNA_TATA_Cj#8 |

TABLE 4-continued

| Gene | No. | Target sequence (5' to 3') | sgRNAs |
|---|---|---|---|
| PMP22 | 9 | CAGTCTTGGCATCACAGGCTTC (SEQ ID NO: 38) | sgRNA_TATA_Cj#9 |
| PMP22 | 10 | GGACCTCTTGGCTATTACACAG (SEQ ID NO: 39) | sgRNA_TATA_Cj#10 |
| PMP22 | 11 | GGAGCCAGTGGGACCTCTTGGC (SEQ ID NO: 40) | sgRNA_TATA_Cj#11 |

TABLE 5

| Gene | No. | Target sequence (5' to 3') | sgRNAs |
|---|---|---|---|
| PMP22 | 1 | TTGGGCATGTTTGAGCTGGT (SEQ ID NO: 41) | sgRNA_Enh_Sp#1 |
| PMP22 | 2 | TTTGGGCATGTTTGAGCTGG (SEQ ID NO: 42) | sgRNA_Enh_Sp#2 |
| PMP22 | 3 | GAGCTGGTGGGCGAAGCATA (SEQ ID NO: 43) | sgRNA_Enh_Sp#3 |
| PMP22 | 4 | AGCTGGTGGGCGAAGCATAT (SEQ ID NO: 44) | sgRNA_Enh_Sp#4 |
| PMP22 | 5 | TGGGCGAAGCATATGGGCAA (SEQ ID NO: 45) | sgRNA_Enh_Sp#5 |
| PMP22 | 6 | GGCCTCCATCCTAAACAATG (SEQ ID NO: 46) | sgRNA_Enh_Sp#6 |
| PMP22 | 7 | GGGTTGGGAGGTTTGGGCGT (SEQ ID NO: 47) | sgRNA_Enh_Sp#10 |
| PMP22 | 8 | AGGTTTGGGCGTGGGAGTCC (SEQ ID NO: 48) | sgRNA_Enh_Sp#11 |
| PMP22 | 9 | TTCAGAGACTCAGCTATTT (SEQ ID NO: 49) | sgRNA_Enh_Sp#12 |
| PMP22 | 10 | GGCCACATTGTTTAGGATG (SEQ ID NO: 50) | sgRNA_Enh_Sp#13 |
| PMP22 | 11 | GGCTTTGGGCATGTTTGAG (SEQ ID NO: 51) | sgRNA_Enh_Sp#14 |
| PMP22 | 12 | AACATGCCCAAAGCCCAGC (SEQ ID NO: 52) | sgRNA_Enh_Sp#15 |
| PMP22 | 13 | ACATGCCCAAAGCCCAGCG (SEQ ID NO: 53) | sgRNA_Enh_Sp#16 |

TABLE 6

| Gene | No. | Target sequence (5' to 3') | sgRNAs |
|---|---|---|---|
| PMP22 | 1 | TTAAATCACAGAGGCAAAGAGTT (SEQ ID NO: 54) | sgRNA_Enh_Cj#1 |
| PMP22 | 2 | TTGCATAGTGCTAGACTGTTTT (SEQ ID NO: 55) | sgRNA_Enh_Cj#2 |
| PMP22 | 3 | GGGTCATGTGTTTTGAAAACAG (SEQ ID NO: 56) | sgRNA_Enh_Cj#3 |
| PMP22 | 4 | CCCAAACCTCCCAACCCACAAC (SEQ ID NO: 57) | sgRNA_Enh_Cj#4 |
| PMP22 | 5 | ACTCAGCTATTTCTGGAATGAC (SEQ ID NO: 58) | sgRNA_Enh_Cj#5 |

TABLE 6-continued

| Gene | No. | Target sequence(5' to 3') | sgRNAs |
|---|---|---|---|
| PMP22 | 6 | TCATCGCCTTTGTGAGCTCCAT (SEQ ID NO: 59) | sgRNA_Enh_Cj#6 |
| PMP22 | 7 | CAGACACAGGCTTTGCTCTAGC (SEQ ID NO: 60) | sgRNA_Enh_Cj#7 |
| PMP22 | 8 | CAAAGCCTGTGTCTGGCCACTA (SEQ ID NO: 61) | sgRNA_Enh_Cj#8 |
| PMP22 | 9 | AGCAGTTTGTGCCCACTAGTGG (SEQ ID NO: 62) | sgRNA_Enh_Cj#9 |
| PMP22 | 10 | ATGTCAAGGTATTCCAGCTAAC (SEQ ID NO: 63) | sgRNA_Enh_Cj#10 |
| PMP22 | 11 | GAATAACTGTATCAAAGTTAGC (SEQ ID NO: 64) | sgRNA_Enh_Cj#11 |
| PMP22 | 12 | TTCCTAATTAAGAGGCTTTGTG (SEQ ID NO: 65) | sgRNA_Enh_Cj#12 |
| PMP22 | 13 | GAGCTAGTTTGTCAGGGTCTAG (SEQ ID NO: 66) | sgRNA_Enh_Cj#13 |

TABLE 7

| Gene | No. | Target sequence (5' to 3') with PAM | sgRNAs |
|---|---|---|---|
| PMP22 | 1 | TATGGAATTCCCAAGCCCCCTGG (SEQ ID NO: 143) | sgRNA_DEnhB_Sp#1 |
| PMP22 | 2 | GGAATTCCATATGAGTCATCTGG (SEQ ID NO: 144) | sgRNA_DEnhB_Sp#2 |
| PMP22 | 3 | CACAGCCTACACTTTGATTATGG (SEQ ID NO: 145) | sgRNA_DEnhB_Sp#3 |
| PMP22 | 4 | TCAGGAGCATTAAGCATATAGGG (SEQ ID NO: 146) | sgRNA_DEnhB_Sp#4 |
| PMP22 | 5 | GACCACGGTCCATGAATTCCTGG (SEQ ID NO: 147) | sgRNA_DEnhC_Sp#1 |
| PMP22 | 6 | AGTATTTGCAGCTGAACAAAAGG (SEQ ID NO: 148) | sgRNA_DEnhC_Sp#2 |
| PMP22 | 7 | ATGGAGTACAGAGAGACATAAGG (SEQ ID NO: 149) | sgRNA_DEnhC_Sp#3 |
| PMP22 | 8 | AAAGAATCAATGCACAGCCATGG (SEQ ID NO: 150) | sgRNA_DEnhC_Sp#4 |

Composition for Manipulation-Gene Scissors System

The SC function-controlling system (including The SC function-controlling modification system) of the present invention may include a guide nucleic acid-editor protein complex as a composition for manipulating a SC function-controlling factor, that is, a PMP22 gene.

Guide Nucleic Acid-Editor Protein Complex

The term "guide nucleic acid-editor protein complex" refers to a complex formed through the interaction between a guide nucleic acid and an editor protein, and the nucleic acid-protein complex includes a guide nucleic acid and an editor protein.

The term "guide nucleic acid" refers to a nucleic acid capable of recognizing a target nucleic acid, gene, chromosome or protein.

The guide nucleic acid may be present in the form of DNA, RNA or a DNA/RNA hybrid, and may have a nucleic acid sequence of 5 to 150 bases.

The guide nucleic acid may include one or more domains.

The domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The guide nucleic acid may have one continuous nucleic acid sequence.

For example, the one continuous nucleic acid sequence may be $(N)_m$, where N represents A, T, C or G, or A, U, C or G, and m is an integer of 1 to 150.

The guide nucleic acid may have two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and m and o may be the same as or different from each other.

The term "editor protein" refers to a peptide, polypeptide or protein which is able to directly bind to or interact with, without direct binding to, a nucleic acid.

The editor protein may be an enzyme.

The editor protein may be a fusion protein.

Here, the "fusion protein" refers to a protein that is produced by fusing an enzyme with an additional domain, peptide, polypeptide or protein.

The term "enzyme" refers to a protein that contains a domain capable of cleaving a nucleic acid, gene, chromosome or protein.

The additional domain, peptide, polypeptide or protein may be a functional domain, peptide, polypeptide or protein, which has a function the same as or different from the enzyme.

The fusion protein may include an additional domain, peptide, polypeptide or protein at one or more regions of the amino terminus (N-terminus) of the enzyme or the vicinity thereof; the carboxyl terminus (C-terminus) or the vicinity thereof; the middle part of the enzyme; and a combination thereof.

The fusion protein may include a functional domain, peptide, polypeptide or protein at one or more regions of the N-terminus of the enzyme or the vicinity thereof; the C-terminus or the vicinity thereof; the middle part of the enzyme; and a combination thereof.

The guide nucleic acid-editor protein complex may serve to modify a subject.

The subject may be a target nucleic acid, gene, chromosome or protein.

For example, the guide nucleic acid-editor protein complex may result in final regulation (e.g., inhibition, suppression, reduction, increase or promotion) of the expression of a protein of interest, removal of the protein, or expression of a new protein.

Here, the guide nucleic acid-editor protein complex may act at a DNA, RNA, gene or chromosome level.

The guide nucleic acid-editor protein complex may act in gene transcription and translation stages.

The guide nucleic acid-editor protein complex may act at a protein level.

1. Guide Nucleic Acids

The guide nucleic acid is a nucleic acid that is capable of recognizing a target nucleic acid, gene, chromosome or protein, and forms a guide nucleic acid-protein complex.

Here, the guide nucleic acid is configured to recognize or target a nucleic acid, gene, chromosome or protein targeted by the guide nucleic acid-protein complex.

The guide nucleic acid may be present in the form of DNA, RNA or a DNA/RNA mixture, and have a 5 to 150-nucleic acid sequence.

The guide nucleic acid may be present in a linear or circular shape.

The guide nucleic acid may be one continuous nucleic acid sequence.

For example, the one continuous nucleic acid sequence may be $(N)_m$, where N is A, T, C or G, or A, U, C or G, and m is an integer of 1 to 150.

The guide nucleic acid may be two or more continuous nucleic acid sequences.

For example, the two or more continuous nucleic acid sequences may be $(N)_m$ and $(N)_o$, where N represents A, T, C or G, or A, U, C or G, m and o are an integer of 1 to 150, and may be the same as or different from each other.

The guide nucleic acid may include one or more domains.

Here, the domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The domains will be described below.

i) Guide Domain

The term "guide domain" is a domain having a complementary guide sequence which is able to form a complementary bond with a target sequence on a target gene or nucleic acid, and serves to specifically interact with the target gene or nucleic acid.

The guide sequence is a nucleic acid sequence complementary to the target sequence on a target gene or nucleic acid, which has, for example, at least 50% or more, 55%, 60%, 65%, 70%, 75%, 80%, 85%, 90% or 95% complementarity or complete complementarity.

The guide domain may be a sequence of 5 to 50 bases.

In an example, the guide domain may be a sequence of 5 to 50, 10 to 50, 15 to 50, 20 to 50, 25 to 50, 30 to 50, 35 to 50, 40 to 50 or 45 to 50 bases.

In another example, the guide domain may be a sequence of 1 to 5, 5 to 10, 10 to 15, 15 to 20, 20 to 25, 25 to 30, 30 to 35, 35 to 40, 40 to 45, or 45 to 50 bases.

The guide domain may have a guide sequence.

The guide sequence may be a complementary base sequence which is able to form a complementary bond with the target sequence on the target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

The guide sequence may be a 5 to 50-base sequence.

In an example, the guide domain may be a 5 to 50, 10 to 50, 15 to 50, 20 to 50, 25 to 50, 30 to 50, 35 to 50, 40 to 50, or 45 to 50-base sequence.

In another example, the guide sequence may be a 1 to 5, 5 to 10, 10 to 15, 15 to 20, 20 to 25, 25 to 30, 30 to 35, 35 to 40, 40 to 45, or 45 to 50-base sequence.

In addition, the guide domain may include a guide sequence and an additional base sequence.

The additional base sequence may be utilized to improve or degrade the function of the guide domain.

The additional base sequence may be utilized to improve or degrade the function of the guide sequence.

The additional base sequence may be a 1 to 35-base sequence.

In one example, the additional base sequence may be a 5 to 35, 10 to 35, 15 to 35, 20 to 35, 25 to 35 or 30 to 35-base sequence.

In another example, the additional base sequence may be a 1 to 5, 5 to 10, 10 to 15, 15 to 20, 20 to 25, 25 to 30 or 30 to 35-base sequence.

The additional base sequence may be located at the 5' end of the guide sequence.

The additional base sequence may be located at the 3' end of the guide sequence.

ii) First Complementary Domain

The term "first complementary domain" is a nucleic acid sequence including a nucleic acid sequence complementary to a second complementary domain, and has enough complementarity so as to form a double strand with the second complementary domain.

The first complementary domain may be a 5 to 35-base sequence.

In an example, the first complementary domain may be a 5 to 35, 10 to 35, 15 to 35, 20 to 35, 25 to 35, or 30 to 35-base sequence.

In another example, the first complementary domain may be a 1 to 5, 5 to 10, 10 to 15, 15 to 20, 20 to 25, 25 to 30 or 30 to 35-base sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-base sequence.

In one example, the linker domain may be a 1 to 5, 5 to 10, 10 to 15, 15 to 20, 20 to 25, or 25 to 30-base sequence.

In another example, the linker domain may be a 1 to 30, 5 to 30, 10 to 30, 15 to 30, 20 to 30, or 25 to 30-base sequence.

iv) Second Complementary Domain

The term "second complementary domain" is a nucleic acid sequence including a nucleic acid sequence complementary to the first complementary domain, and has enough complementarity so as to form a double strand with the first complementary domain.

The second complementary domain may have a base sequence complementary to the first complementary domain, and a base sequence having no complementarity to the first complementary domain, for example, a base sequence not forming a double strand with the first complementary domain, and may have a longer base sequence than the first complementary domain.

The second complementary domain may have a 5 to 35-base sequence.

In an example, the second complementary domain may be a 1 to 35, 5 to 35, 10 to 35, 15 to 35, 20 to 35, 25 to 35, or 30 to 35-base sequence.

In another example, the second complementary domain may be a 1 to 5, 5 to 10, 10 to 15, 15 to 20, 20 to 25, 25 to 30, or 30 to 35-base sequence.

v) Proximal Domain

The term "proximal domain" is a nucleic acid sequence located adjacent to the second complementary domain.

The proximal domain may have a complementary base sequence therein, and may be formed in a double strand due to a complementary base sequence.

The proximal domain may be a 1 to 20-base sequence.

In one example, the proximal domain may be a 1 to 20, 5 to 20, 10 to 20 or 15 to 20-base sequence.

In another example, the proximal domain may be a 1 to 5, 5 to 10, 10 to 15 or 15 to 20-base sequence.

vi) Tail Domain

The term "tail domain" is a nucleic acid sequence located at one or more ends of the both ends of the guide nucleic acid.

The tail domain may have a complementary base sequence therein, and may be formed in a double strand due to a complementary base sequence.

The tail domain may be a 1 to 50-base sequence.

In an example, the tail domain may be a 5 to 50, 10 to 50, 15 to 50, 20 to 50, 25 to 50, 30 to 50, 35 to 50, 40 to 50, or 45 to 50-base sequence.

In another example, the tail domain may be a 1 to 5, 5 to 10, 10 to 15, 15 to 20, 20 to 25, 25 to 30, 30 to 35, 35 to 40, 40 to 45, or 45 to 50-base sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3' phosphorothioate (MS) or 2'-O-methyl 3' thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

As a specific example of the guide nucleic acid of the present invention, gRNA will be described below.

gRNA

The term "gRNA" refers to a nucleic acid capable of specifically targeting a gRNA-CRISPR enzyme complex, that is, a CRISPR complex, with respect to a target gene or nucleic acid. In addition, the gRNA is a nucleic acid-specific RNA which may bind to a CRISPR enzyme and guide the CRISPR enzyme to the target gene or nucleic acid.

The gRNA may include multiple domains. Due to each domain, interactions may occur in a three-dimensional structure or active form of a gRNA strand, or between these strands.

The gRNA may be called single-stranded gRNA (single RNA molecule); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain, a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid and a first complementary domain; and a second strand which includes a second complementary domain, a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; a second complementary domain, and a domain having a sequence complementary to the first complementary domain sequence, thereby forming a double-stranded nucleic acid with the first complementary domain in the 5' to 3' direction.

i) Guide Domain

The guide domain includes a complementary guide sequence capable of forming a complementary bond with a target sequence on a target gene or nucleic acid. The guide sequence may be a nucleic acid sequence having complementarity to the target sequence on the target gene or nucleic acid, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

The guide domain may be a 5 to 50-base sequence.

As an exemplary embodiment, the guide domain may be a 16, 17, 18, 19, 20, 21, 22, 23, 24 or 25-base sequence.

As an exemplary embodiment, the guide domain may include a 16, 17, 18, 19, 20, 21, 22, 23, 24 or 25-base sequence.

Here, the guide domain may include a guide sequence.

The guide sequence may be a complementary base sequence capable of forming a complementary bond with a target sequence on a target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of a PMP22 gene, which has, for example, at least 70%, 75%, 80%, 85%, 90% or 95% or more complementarity or complete complementarity.

The guide sequence may be a 5 to 50-base sequence.

In an exemplary embodiment, the guide sequence may be a 16, 17, 18, 19, 20, 21, 22, 23, 24 or 25-base sequence.

In one exemplary embodiment, the guide sequence may include a 16, 17, 18, 19, 20, 21, 22, 23, 24 or 25-base sequence.

In one exemplary embodiment, the guide sequence may be a nucleic acid sequence complementary to a target sequence of the PMP22 gene, which is a 16, 17, 18, 19, 20, 21, 22, 23, 24 or 25-base sequence.

Here, target sequences of the target genes, that is, the PMP22 gene for the guide sequence are listed above in Table 1, Table 2, Table 3, Table 4, Table 5, Table 6 and Table 7, respectively, but the present invention is not limited thereto.

Here, the guide domain may include a guide sequence and an additional base sequence.

The additional base sequence may be a 1 to 35-base sequence.

In one exemplary embodiment, the additional base sequence may be a 1, 2, 3, 4, 5, 6, 7, 8, 9 or 10-base sequence.

For example, the additional base sequence may be a single base sequence, guanine (G), or a sequence of two bases, GG.

The additional base sequence may be located at the 5' end of the guide sequence.

The additional base sequence may be located at the 3' end of the guide sequence.

Selectively, a part or all of the base sequence of the guide domain may include a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

ii) First Complementary Domain

The first complementary domain includes a nucleic acid sequence complementary to a second complementary domain, and has enough complementarity such that it is able to form a double strand with the second complementary domain.

Here, the first complementary domain may be a 5 to 35-base sequence. The first complementary domain may include a 5 to 35-base sequence.

In one exemplary embodiment, the first complementary domain may be a 5, 6, 7, 8, 9, 10, 11, 12, 13, 14, 15, 16, 17, 18, 19, 20, 21, 22, 23, 24, or 25-base sequence.

In another embodiment, the first complementary domain may include a 5, 6, 7, 8, 9, 10, 11, 12, 13, 14, 15, 16, 17, 18, 19, 20, 21, 22, 23, 24, or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Streptococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 149) or a base sequence having partial, that is, at least 50% or more, or complete homology with 5'-GUUUUAGAGCUA-3' (SEQ ID NO: 149). Here, the first complementary domain may further include $(X)_n$, resulting in 5'-GUUUUAGAGCUA $(X)_n$-3' (SEQ ID NO: 178). The X may be selected from the group consisting of bases A, T, U and G, and the n may represent the number of bases, which is an integer of 5 to 15. Here, the $(X)_n$ may be n repeats of the same base, or a mixture of n bases of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3', (SEQ ID NO: 152) or a base sequence having partial, that is, at least 50% or more, or complete homology with 5'-GUUUUAGUCCCUUUUUAAAUUUCUU-3' (SEQ ID NO: 152). Here, the first complementary domain may further include $(X)_n$, resulting in 5'-GUUUUAGUCCCUUUUUAAAUUUCUU $(X)_n$-3' (SEQ ID NO: 179). The X may be selected from the group consisting of bases A, T, U and G, and the n may represent the number of bases, which is an integer of 5 to 15. Here, the $(X)_n$ may represent n repeats of the same base, or a mixture of n bases of A, T, U and G.

In another embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella* bovoculi (237), *Smithella* sp. (SC_KO8D17), *Leptospira inadai*, Lachnospiraceae bacterium (MA2020), *Francisella novicida* (U112), Candidatus Methanoplasma *termitum* or *Eubacterium eligens*, or a first complementary domain derived therefrom.

For example, when the first complementary domain is the first complementary domain of Parcubacteria bacterium or a first complementary domain derived therefrom, the first complementary domain may be 5'-UUUGUAGAU-3' (SEQ ID NO: 154), or a base sequence having partial, that is, at least 50% or more homology with 5'-UUUGUAGAU-3' (SEQ ID NO: 154). Here, the first complementary domain may further include $(X)_n$, resulting in 5'-$(X)_n$UUUGUAGAU-3' (SEQ ID NO: 180). The X may be selected from the group consisting of bases A, T, U and G, and the n may represent the number of bases, which is an integer of 1 to 5. Here, the $(X)_n$ may represent n repeats of the same base, or a mixture of n bases of A, T, U and G.

Selectively, a part or all of the base sequence of the first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iii) Linker Domain

The linker domain is a nucleic acid sequence connecting two or more domains, and connects two or more identical or different domains. The linker domain may be connected with two or more domains, or may connect two or more domains by covalent or non-covalent bonding.

The linker domain may be a nucleic acid sequence connecting a first complementary domain with a second complementary domain to produce single-stranded gRNA.

The linker domain may be connected with the first complementary domain and the second complementary domain by covalent or non-covalent bonding.

The linker domain may connect the first complementary domain with the second complementary domain by covalent or non-covalent bonding The linker domain may be a 1 to 30-base sequence. The linker domain may include a 1 to 30-base sequence.

In an exemplary embodiment, the linker domain may be a 1 to 5, 5 to 10, 10 to 15, 15 to 20, 20 to 25 or 25 to 30-base sequence.

In an exemplary embodiment, the linker domain may include a 1 to 5, 5 to 10, 10 to 15, 15 to 20, 20 to 25, or 25 to 30-base sequence.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding. The linker domain may be used to produce single-stranded gRNA by being connected with crRNA and tracrRNA of double-stranded gRNA or connecting the crRNA with the tracrRNA by covalent or non-covalent bonding.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iv) Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be a 5 to 35-base sequence. The first complementary domain may include a 5 to 35-base sequence.

In an exemplary embodiment, the second complementary domain may be a 5, 6, 7, 8, 9, 10, 11, 12, 13, 14, 15, 16, 17, 18, 19, 20, 21, 22, 23, 24 or 25-base sequence.

In an exemplary embodiment, the second complementary domain may include a 5, 6, 7, 8, 9, 10, 11, 12, 13, 14, 15, 16, 17, 18, 19, 20, 21, 22, 23, 24 or 25-base sequence.

In addition, the second complementary domain may have homology with a natural second complementary domain, or may be derived from the natural second complementary domain. In addition, the second complementary domain may have a difference in base sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Streptococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 155), or a base sequence having partial, that is, at least 50% or more homology with 5'-UAGCAAGUUAAAAU-3' (SEQ ID NO: 155) (a base sequence forming a double strand with the first complementary domain is underlined). Here, the second complementary domain may further include $(X)_n$ and/or $(X)_m$, resulting in 5'-$(X)_n$UAGCAAGUUAAAAU $(X)_m$-3' (SEQ ID NO: 181). The X may be selected from the group consisting of bases A, T, U and G, and each of the n and m may represent the number of bases, in which the n may be an integer of 1 to 15, and the m may be an integer of 1 to 6. Here, the $(X)_n$ may represent n repeats of the same base, or a mixture of n bases of A, T, U and G. In addition, $(X)_m$ may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 157), or a base sequence having partial, that is, at least 50% or more homology with 5'-AAGAAAUUUAAAAAGGGACUAAAAU-3' (SEQ ID NO: 157) (a base sequence forming a double strand with the first complementary domain is underlined). Here, the second complementary domain may further include $(X)_n$ and/or $(X)_m$, resulting in 5'-$(X)_n$AAGAAAUUUAAAAAGGGACUAAAAU $(X)_m$-3' (SEQ ID NO: 182). The X may be selected from the group consisting of bases A, T, U and G, and each of the n and m may represent the number of bases, in which the n may be an integer of 1 to 15, and the m may be an integer of 1 to 6. Here, $(X)_n$ may represent n repeats of the same base, or a mixture of n bases of A, T, U and G. In addition, $(X)_m$ may represent m repeats of the same base, or a mixture of m bases of A, T, U and G.

In another embodiment, the second complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), Candidatus Methanoplasma termitum or *Eubacterium eligens*, or a second complementary domain derived therefrom.

For example, when the second complementary domain is a second complementary domain of Parcubacteria bacterium or a second complementary domain derived therefrom, the second complementary domain may be 5'-AAAUUUCUACU-3' (SEQ ID NO: 160), or a base sequence having partial, that is, at least 50% or more homology with 5'-AAAUUUCUACU-3' (SEQ ID NO: 160) (a base sequence forming a double strand with the first complementary domain is underlined). Here, the second complementary domain may further include $(X)_n$ and/or $(X)_m$, resulting in 5'-$(X)_n$AAAUUUCUACU $(X)_m$-3' (SEQ ID NO: 183). The X may be selected from the group consisting of bases A, T, U and G, and each of the n and m may represent the number of bases, in which the n may be an integer of 1 to 10, and the m may be an integer of 1 to 6. Here, the $(X)_n$ may represent n repeats of the same base, or a mixture of n bases of A, T, U and G. In addition, the $(X)_m$ may represent m repeats of the same base, or a mixture of m bases of A, T, U and G.

Selectively, a part or all of the base sequence of the second complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

v) Proximal Domain

The proximal domain is a sequence of 1 to 20 bases located adjacent to the second complementary domain, and a domain located at the 3' end direction of the second complementary domain. Here, the proximal domain may be used to form a double strand between complementary base sequences therein.

In one exemplary embodiment, the proximal domain may be a 5, 6, 7, 8, 9, 10, 11, 12, 13, 14 or 15-base sequence.

In another embodiment, the proximal domain may include a 5, 6, 7, 8, 9, 10, 11, 12, 13, 14 or 15-base sequence.

In addition, the proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes*, *Campylobacter jejuni*, *Streptococcus thermophilus*, *Streptococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGCUAGUCCG-3' (SEQ ID NO: 158), or a base sequence having partial, that is, at least 50% or more homology with 5'-AAGGCUAGUCCG-3' (SEQ ID NO: 158). Here, the proximal domain may further include $(X)_n$, resulting in 5'-AAGGCUAGUCCG $(X)_n$-3' (SEQ ID NO: 201). The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 159), or a base sequence having at least 50% or more homology with 5'-AAAGAGUUUGC-3' (SEQ ID NO: 159). Here, the proximal domain may further include $(X)_n$, resulting in 5'-AAAGAGUUUGC $(X)_n$-3' (SEQ ID NO: 184). The X may be selected from the group consisting of bases A, T, U and G, and the n may represent the number of bases, which is an integer of 1 to 40. Here, the $(X)_n$ may represent n repeats of the same base, or a mixture of n bases of A, T, U and G.

Selectively, a part or all of the base sequence of the proximal domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

vi) Tail Domain

The tail domain is a domain which is able to be selectively added to the 3' end of single-stranded gRNA or double-stranded gRNA. The tail domain may be a 1 to 50-base sequence, or include a 1 to 50-base sequence. Here, the tail domain may be used to form a double strand between complementary base sequences therein.

In an exemplary embodiment, the tail domain may be a 1 to 5, 5 to 10, 10 to 15, 15 to 20, 20 to 25, 25 to 30, 30 to 35, 35 to 40, 40 to 45, or 45 to 50-base sequence.

In an exemplary embodiment, the tail domain may include a 1 to 5, 5 to 10, 10 to 15, 15 to 20, 20 to 25, 25 to 30, 30 to 35, 35 to 40, 40 to 45, or 45 to 50-base sequence.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Streptococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 161), or a base sequence having partial, that is, at least 50% or more homology with 5'-UUAUCAAC-UUGAAAAAGUGGCACCGAGUCGGUGC-3' (SEQ ID NO: 161). Here, the tail domain may further include $(X)_n$, resulting in 5'-UUAUCAAC-UUGAAAAAGUGGCACCGAGUCGGUGC $(X)_n$-3' (SEQ ID NO: 185). The X may be selected from the group consisting of bases A, T, U and G, and the n may represent the number of bases, which is an integer of 1 to 15. Here, the $(X)_n$ may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 162), or a base sequence having partial, that is, at least 50% or more homology with 5'-GGGACUCUGCGGGGUUA-CAAUCCCCUAAAACCGCUUUU-3' (SEQ ID NO: 162). Here, the tail domain may further include $(X)_n$, resulting in 5'-GGGACUCUGCGGGGUUACAAUCCCC-UAAAACCGCUUUU $(X)_n$-3' (SEQ ID NO: 186). The X may be selected from the group consisting of bases A, T, U and G, and the n may represent the number of bases, which is an integer of 1 to 15. Here, the $(X)_n$ may represent n repeats of the same base, or a mixture of n bases of A, T, U and G.

In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU (SEQ ID NO: 187), when an H1 promoter is used in transcription, the tail domain may be UUUU, and when a pol-III promoter is used, the tail domain may include several uracil bases or alternative bases.

Selectively, a part or all of the base sequence of the tail domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

The gRNA may include a plurality of domains as described above, and therefore, the length of the nucleic acid sequence may be regulated according to a domain contained in the gRNA, and interactions may occur in strands in a three-dimensional structure or active form of gRNA or between these strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of

5'-[guide domain]-[first complementary domain]-3', and

The Second Strand May Consist of

5'-[second complementary domain]-[proximal domain]-3' or

5'-[second complementary domain]-[proximal domain]-[tail domain]-3'.

Here, the first strand may be referred to as crRNA, and the second strand may be referred to as tracrRNA.

First Strand

Guide Domain

In the first strand, the guide domain includes a complementary guide sequence which is able to form a complementary bond with a target sequence on a target gene or nucleic acid. The guide sequence is a nucleic acid sequence complementary to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be a 5 to 50-base sequence, or includes a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence which is able to form a complementary bond with a target sequence on a target gene or nucleic acid, which has, for example, at least 70%, 75%, 80%, 85%, 90% or 95% or more complementarity or complete complementarity.

In an exemplary embodiment, the guide sequence may be a nucleic acid sequence complementary to a target gene, that is, a target sequence of a PMP22 gene, which has, for example, at least 70%, 75%, 80%, 85%, 90% or 95% or more complementarity or complete complementarity.

Here, the guide sequence may be a 5 to 50-base sequence or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the PMP22 gene. The guide sequence may be or include a 5 to 50-base sequence. For example, the guide sequence may be or include a 16, 17, 18, 19, 20, 21, 22, 23, 24 or 25-base sequence.

Here, for the guide sequence, target genes, that is, target sequences of a PMP22 gene are listed above in Table 1, Table 2, Table 3, Table 4, Table 5, Table 6 and Table 7 but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may include one base, guanine (G), or two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain includes a nucleic acid sequence complementary to a second complementary domain of the second strand, and is a domain having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in base sequence according to a species existing in nature, may be derived from the first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Streptococcus pyogenes, Campylobacter jejuni, Streptococcus thermophilus, Streptococcus aureus or Neisseria meningitides, or a first complementary domain derived therefrom.

Selectively, the first complementary domain may include an additional base sequence which does not undergo complementary bonding with the second complementary domain of the second strand.

Here, the additional base sequence may be a sequence of 1 to 15 bases. For example, the additional base sequence may be a sequence of 1 to 5, 5 to 10, or 10 to 15 bases.

Selectively, a part or all of the base sequence of the guide domain and/or first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the first strand may consist of 5'-[guide domain]-[first complementary domain]-3' as described above.

In addition, the first strand may optionally include an additional base sequence.

In One Example, the First Strand May be

5'-($N_{target}$)-($Q$)$_m$-3'; or

5'-($X$)$_a$—($N_{target}$)—($X$)$_b$-($Q$)$_m$-($X$)$_c$-3'.

Here, the $N_{target}$ is a base sequence capable of forming a complementary bond with a target sequence on a target gene or nucleic acid, and a base sequence region which may be changed according to a target sequence on a target gene or nucleic acid.

In one exemplary embodiment, $N_{target}$ may be a base sequence capable of forming a complementary bond with a target gene, that is, a target sequence of a PMP22 gene.

Here, the $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of Streptococcus pyogenes or a Streptococcus pyogenes-derived first complementary domain, the $(Q)_m$ may be 5'-GUUUUAGAGCUA-3' (SEQ ID NO: 149), or a base sequence having at least 50% or more homology with 5'-GUUUUAGAGCUA-3' (SEQ ID NO: 149).

In another example, when the first complementary domain has partial or complete homology with a first complementary domain of Campylobacter jejuni or a Campylobacter jejuni-derived first complementary domain, the $(Q)_m$ may be 5'-GUUUUAGUCCC-UUUUUAAAUUUCUU-3' (SEQ ID NO: 152), or a base sequence having at least 50% or more homology with 5'-GUUUUAGUCCCUUUUUAAAUUUCUU-3' (SEQ ID NO: 152).

In still another example, when the first complementary domain has partial or complete homology with a first complementary domain of Streptococcus thermophilus or a Streptococcus thermophilus-derived first complementary domain, the $(Q)_m$ may be 5'-GUUUUAGAGCUGUGUU-GUUUCG-3' (SEQ ID NO: 153), or a base sequence having at least 50% or more homology with 5'-GUUUUAGAGCU-GUGUUGUUUCG-3' (SEQ ID NO: 153).

In addition, each of the $(X)_a$, $(X)_b$ and $(X)_c$ is selectively an additional base sequence, where the X may be each independently selected from the group consisting of A, U, C and G, and each of the a, b and c may be the number of bases, which is 0 or an integer of 1 to 20.

Second Strand

The second strand may consist of a second complementary domain and a proximal domain, and selectively include a tail domain.

Second Complementary Domain

In the second strand, the second complementary domain includes a nucleic acid sequence complementary to the first complementary domain of the first strand, and has enough complementarity so as to form a double strand with the first complementary domain. The second complementary domain may include a base sequence complementary to the first complementary domain and a base sequence not complementary to the first complementary domain, for example, a base sequence not forming a double strand with the first complementary domain, and may have a longer base sequence than the first complementary domain.

Here, the second complementary domain may be a 5 to 35-base sequence, or include a 5 to 35-base sequence. For example, the second complementary domain may be or include a 5, 6, 7, 8, 9, 10, 11, 12, 13, 14, 15, 16, 17, 18, 19, 20, 21, 22, 23, 24 or 25-base sequence, but the present invention is not limited thereto.

The second complementary domain may have homology with a natural second complementary domain, or may be derived from a natural second complementary domain. In addition, the second complementary domain may have a difference in base sequence thereof according to a species existing in nature, may be derived from a second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of *Streptococcus pyogenes, Campylobacter jejuni, Streptococcus thermophilus, Streptococcus aureus* or *Neisseria meningitides*, or a second complementary domain derived therefrom.

Selectively, the second complementary domain may further include an additional base sequence which does not undergo complementary bonding with the first complementary domain of the first strand.

Here, the additional base sequence may be a 1 to 25-base sequence. For example, the additional base sequence may be a 1 to 5, 5 to 10, 10 to 15, 15 to 20 or 20 to 25-base sequence.

Proximal Domain

In the second strand, the proximal domain is a sequence of 1 to 20 bases, and a domain located at the 3' end direction of the second complementary domain. For example, the proximal domain may be or include a sequence of 5, 6, 7, 8, 9, 10, 11, 12, 13, 14 or 15 bases.

Here, the proximal domain may have a double strand bond between complementary base sequences therein.

In addition, the proximal domain may have homology with a natural proximal domain, or may be derived from a natural proximal domain. In addition, the proximal domain may have a difference in base sequence according to a species existing in nature, may be derived from a proximal domain of a species existing in nature, or may have partial or complete homology with the proximal domain of a species existing in nature.

In one exemplary embodiment, the proximal domain may have partial, that is, at least 50% or more, or complete homology with a proximal domain of *Streptococcus pyogenes, Campylobacter jejuni, Streptococcus thermophilus, Streptococcus aureus* or *Neisseria meningitides*, or a proximal domain derived therefrom.

Tail Domain

Selectively, in the second strand, the tail domain may be a domain selectively added to the 3' end of the second strand, and the tail domain may be or include a 1 to 50-base sequence. For example, the tail domain may be or include a 1 to 5, 5 to 10, 10 to 15, 15 to 20, 20 to 25, 25 to 30, 30 to 35, 35 to 40, 40 to 45 or 45 to 50-base sequence.

Here, the tail domain may have a double strand bond between complementary base sequences therein.

In addition, the tail domain may have homology with a natural tail domain, or may be derived from a natural tail domain. In addition, the tail domain may have a difference in base sequence according to a species existing in nature, may be derived from a tail domain contained in the species existing in nature, or may have partial or complete homology with the tail domain contained in the species existing in nature.

In one exemplary embodiment, the tail domain may have partial, that is, at least 50% or more, or complete homology with a tail domain of *Streptococcus pyogenes, Campylobacter jejuni, Streptococcus thermophilus, Streptococcus aureus* or *Neisseria meningitides*, or a tail domain derived therefrom.

In another embodiment, the tail domain may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU (SEQ ID NO: 187), when an H1 promoter is used in transcription, the tail domain may be UUUU, and when a pol-III promoter is used, the tail domain may include several uracil bases or alternative bases.

Selectively, a part or all of each of the base sequence of the second complementary domain, the proximal domain and/or the tail domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the second strand may consist of 5'-[second complementary domain]-[proximal domain]-3' or 5'-[second complementary domain]-[proximal domain]-[tail domain]-3' as described above.

In addition, the second strand may selectively include an additional base sequence.

In one exemplary embodiment, the second strand may be 5'-$(Z)_h$—$(P)_k$-3'; or 5'-$(X)_d$—$(Z)_n$—$(X)_e$—$(P)_k$—$(X)_f$-3'.

In another embodiment, the second strand may be 5'-$(Z)_h$—$(P)_k$—$(F)_i$-3'; or 5'-$(X)_d$—$(Z)_h$—$(X)_e$—$(P)_k$—$(X)_f$—$(F)_i$-3'.

Here, the $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 155), or a base sequence having at least 50% or more homology with 5'-UAGCAAGUUAAAAU-3' (SEQ ID NO: 155).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 157), or a base sequence having at least 50% or more homology with 5'-AAGAAAUUUAAAAAGGGAC-UAAAAU-3' (SEQ ID NO: 157).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 156), or a base sequence having at least 50% or more homology with 5'-CGAAACAACACAGCGA-GUUAAAAU-3' (SEQ ID NO: 156).

The $(P)_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes or a proximal domain derived therefrom, the $(P)_k$ may be 5'-AAGGCUAGUCCG-3' (SEQ ID NO: 158), or a base sequence having at least 50% or more homology with 5'-AAGGCUAGUCCG-3' (SEQ ID NO: 158).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 159), or a base sequence having at least 50% or more homology with 5'-AAAGAGUUUGC-3' (SEQ ID NO: 159).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 166), or a base sequence having at least 50% or more homology with 5'-AAGGCUUAGUCCG-3' (SEQ ID NO: 166).

The $(F)_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the $(F)_i$ may be 5'-UUAU-CAACUUGAAAAAGUGGCACCGAGUCGGUGC-3' (SEQ ID NO: 161), or a base sequence having at least 50% or more homology with 5'-UUAUCAAC-UUGAAAAAGUGGCACCGAGUCGGUGC-3' (SEQ ID NO: 161).

In another example, when the tail domain has partial or complete homology with a tail domain of *Campylobacter jejuni* or a tail domain derived therefrom, the $(F)_i$ may be 5'-GGGACUCUGCGGGGUUACAAUCCCC-UAAAACCGCUUUU-3' (SEQ ID NO: 162), or a base sequence having at least 50% or more homology with 5'-GGGACUCUGCGGGGUUACAAUCCCC-UAAAACCGCUUUU-3' (SEQ ID NO: 162).

In still another example, when the tail domain has partial or complete homology with a tail domain of *Streptococcus thermophilus* or a tail domain derived therefrom, the $(F)_i$ may be 5'-UACUCAACUUGAAAAG-GUGGCACCGAUUCGGUGUUUUU-3' (SEQ ID NO: 163), or a base sequence having at least 50% or more homology with 5'-UACUCAACUUGAAAAG-GUGGCACCGAUUCGGUGUUUUU-3' (SEQ ID NO: 163).

In addition, the $(F)_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU (SEQ ID NO: 187), when an H1 promoter is used in transcription, the tail domain may be UUUU, and when a pol-III promoter is used, the tail domain may include several uracil bases or alternative bases.

In addition, the $(X)_d$, $(X)_e$ and $(X)_f$ may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into two types.

i) Single-Stranded gRNA

First, there is single-stranded gRNA in which a first strand or a second strand of the double-stranded gRNA is linked by a linker domain, and here, the single-stranded gRNA consists of 5'-[first strand]-[linker domain]-[second strand]-3'.

Specifically, the single-stranded gRNA may consist of
5'-[guide domain]-[first complementary domain]-[linker domain]-[second complementary domain]-[proximal domain]-3' or
5'-[guide domain]-[first complementary domain]-[linker domain]-[second complementary domain]-[proximal domain]-[tail domain]-3'.

Each domain except the linker domain is the same as the description of each domain of the first and second strands of the double-stranded gRNA.

Linker Domain

In the single-stranded gRNA, the linker domain is a domain connecting a first strand and a second strand, and specifically, is a nucleic acid sequence which connects a first complementary domain with a second complementary domain to produce single-stranded gRNA. Here, the linker domain may be connected with the first complementary domain and the second complementary domain or connect the first complementary domain with the second complementary domain by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

The linker domain is suitable to be used in a single-stranded gRNA molecule, and may be connected with the first strand and the second strand of the double-stranded gRNA, or connect the first strand with the second strand by covalent or non-covalent bonding to be used in production of the single-stranded gRNA. The linker domain may be connected with crRNA and tracrRNA of the double-stranded gRNA, or connect crRNA with tracrRNA by covalent or non-covalent bonding to be used in production of the single-stranded gRNA.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the single-stranded gRNA may consist of 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3' as described above.

In addition, the single-stranded gRNA may selectively include an additional base sequence.

In one exemplary embodiment, the single-stranded gRNA may be

5'-$(N_{target})$-$(Q)_m$-$(L)_j$-$(Z)_n$—$(P)_k$-3'; or

5'-$(N_{target})$-$(Q)_m$-$(L)_j$-$(Z)_h$—$(P)_k$—$(F)_i$-3'.

In another embodiment, the single-stranded gRNA may be

5'-$(X)_a$—$(N_{target})$—$(X)_b$-$(Q)_m$-$(X)_c$-$(L)_j$-$(X)_d$—$(Z)_n$—$(X)_e$—$(P)_k$—$(X)_f$-3'; or 5'-$(X)_a$—$(N_{target})$—$(X)_b$-$(Q)_m$-$(X)_c$-$(L)_j$-$(X)_d$—$(Z)_n$—$(X)_e$—$(P)_k$—$(X)_f$—$(F)_i$-3'.

Here, the $N_{target}$ is a base sequence capable of forming a complementary bond with a target sequence on a target gene or nucleic acid, and a base sequence region capable of being changed according to a target sequence on a target gene or nucleic acid.

In one exemplary embodiment, $N_{target}$ is a base sequence capable of forming a complementary bond with a target gene, that is, a target sequence of a PMP22 gene.

The $(Q)_m$ includes a base sequence including the first complementary domain, which is able to form a complementary bond with a second complementary domain. The $(Q)_m$ may be a sequence having partial or complete homology with a first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a first complementary domain derived therefrom, the $(Q)_m$ may be 5'-GUUUUA-GAGCUA-3' (SEQ ID NO: 149), or a base sequence having at least 50% or more homology with 5'-GUUUUA-GAGCUA-3' (SEQ ID NO: 149).

In another example, when the first complementary domain has partial or complete homology with a first complementary domain of *Campylobacter jejuni* or a first complementary domain derived the therefrom, $(Q)_m$ may be 5'-GUUUUAGUCCCUUUUUAAAUUUCUU-3' (SEQ ID NO: 152), or a base sequence having at least 50% or more homology with 5'-GUUUUAGUCCCUUUUUAA-AUUUCUU-3' (SEQ ID NO: 152).

In still another example, when the first complementary domain has partial or complete homology with a first complementary domain of *Streptococcus thermophilus* or a first complementary domain the derived therefrom, $(Q)_m$ may be 5'-GUUUUAGAGCUGUGUUGUUUCG-3' (SEQ ID NO: 153), or a base sequence having at least 50% or more homology with 5'-GUUUUAGAGCUGUGUUGUUUCG-3' (SEQ ID NO: 153).

In addition, the $(L)_j$ is a base sequence including the linker domain, and connecting the first complementary domain with the second complementary domain, thereby producing single-stranded gRNA. Here, the L may be each independently selected from the group consisting of A, U, C and G, and the j may be the number of bases, which is an integer of 1 to 30.

The $(Z)_h$ is a base sequence including the second complementary domain, which is able to have a complementary bond with the first complementary domain. The $(Z)_h$ may be a sequence having partial or complete homology with the second complementary domain of a species existing in nature, and the base sequence of the second complementary domain may be changed according to the species of origin. The Z may be each independently selected from the group consisting of A, U, C and G, and the h is the number of bases, which may be an integer of 5 to 50.

For example, when the second complementary domain has partial or complete homology with a second complementary domain of *Streptococcus pyogenes* or a second complementary domain derived therefrom, the $(Z)_h$ may be 5'-UAGCAAGUUAAAAU-3' (SEQ ID NO: 155), or a base sequence having at least 50% or more homology with 5'-UAGCAAGUUAAAAU-3' (SEQ ID NO: 155).

In another example, when the second complementary domain has partial or complete homology with a second complementary domain of *Campylobacter jejuni* or a second complementary domain derived therefrom, the $(Z)_h$ may be 5'-AAGAAAUUUAAAAAGGGACUAAAAU-3' (SEQ ID NO: 157), or a base sequence having at least 50% or more homology with 5'-AAGAAAUUUAAAAAGGGAC-UAAAAU-3' (SEQ ID NO: 157).

In still another example, when the second complementary domain has partial or complete homology with a second complementary domain of *Streptococcus thermophilus* or a second complementary domain derived therefrom, the $(Z)_h$ may be 5'-CGAAACAACACAGCGAGUUAAAAU-3' (SEQ ID NO: 156), or a base sequence having at least 50% or more homology with 5'-CGAAACAACAC-AGCGAGUUAAAAU-3' (SEQ ID NO: 156).

The $(P)_k$ is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 158), or a base sequence having at least 50% or more homology with 5'-AAGGCUAGUCCG-3' (SEQ ID NO: 158).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 159), or a base sequence having at least 50% or more homology with 5'-AAAGAGUUUGC-3' (SEQ ID NO: 159).

In still another example, when the proximal domain has partial or complete homology with a proximal domain of *Streptococcus thermophilus* or a proximal domain derived therefrom, the $(P)_k$ may be 5'-AAGGCUUAGUCCG-3' (SEQ ID NO: 166), or a base sequence having at least 50% or more homology with 5'-AAGGCUUAGUCCG-3' (SEQ ID NO: 166).

The $(F)_i$ may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the $(F)_i$ may be 5'-UUAU-CAACUUGAAAAAGUGGCACCGAGUCGGUGC-3' (SEQ ID NO: 161), or a base sequence having at least 50% or more homology with 5'-UUAUCAACUUGAAAAA-GUGGCACCGAGUCGGUGC-3' (SEQ ID NO: 161).

In another example, when the tail domain has partial or complete homology with a tail domain of *Campylobacter jejuni* or a tail domain derived therefrom, the (F); may be 5'-GGGACUCUGCGGGGUUACAAUCCCCUAAAAC-CGCUUUU-3' (SEQ ID NO: 162), or a base sequence having at least 50% or more homology with 5'-GGGACU-CUGCGGGGUUACAAUCCCCUAAAACCGCUUUU-3' (SEQ ID NO: 162).

In still another example, when the tail domain has partial or complete homology with a tail domain of *Streptococcus*

*thermophilus* or a tail domain derived therefrom, the (F)$_i$ may be 5'-UACUCAACUUGAAAAGGUGGCACC-GAUUCGGUGUUUUU-3' (SEQ ID NO: 163), or a base sequence having at or least 50% more homology with 5'-UACUCAACUUGAAAAGGUGGCACCGAUUCG-GUGUUUUU-3' (SEQ ID NO: 163).

In addition, the (F)$_i$ may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU (SEQ ID NO: 187), when an H1 promoter is used in transcription, the tail domain may be UUUU, and when a pol-III promoter is used, the tail domain may include several uracil bases or alternative bases.

In addition, the $(X)_a$, $(X)_b$, $(X)_c$, $(X)_d$, $(X)_e$ and $(X)_f$ may be base sequences selectively added, where the X may be each independently selected from the group consisting of A, U, C and G, and each of the a, b, c, d, e and f may be the number of bases, which is 0 or an integer of 1 to 20.

ii) Single-Stranded gRNA

Second, the single-stranded gRNA may be single-stranded gRNA consisting of a guide domain, a first complementary domain and a second complementary domain, and here, the single-stranded gRNA may consist of:

5'-[second complementary domain]-[first complementary domain]-[guide domain]-3'; or 5'-[second complementary domain]-[linker domain]-[first complementary domain]-[guide domain]-3'.

Guide Domain

In the single-stranded gRNA, the guide domain includes a complementary guide sequence capable of forming a complementary bond with a target sequence on a target gene or nucleic acid. The guide sequence may be a nucleic acid sequence having complementarity to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be or include a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence capable of forming a complementary bond with a target sequence on a target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of a PMP22 gene, which has, for example, at least 70%, 75%, 80%, 85%, 90% or 95% or more complementarity or complete complementarity.

Here, the guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the PMP22 gene. The guide sequence may be or include a 5 to 50-base sequence. For example, the guide sequence may be or include a 16, 17, 18, 19, 20, 21, 22, 23, 24 or 25-base sequence.

Here, target sequences of the target genes, that is, the PMP22 gene for the guide sequence are listed above in Table 1, Table 2, Table 3, Table 4, Table 5, Table 6 and Table 7 respectively, but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may be a single base sequence, guanine (G), or a sequence of two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain is a domain including a nucleic acid sequence complementary to the second complementary domain, and having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens, Moraxella bovoculi* (237), *Smithella* sp. (SC_KO8D17), *Leptospira inadai*, Lachnospiraceae bacterium (MA2020), *Francisella novicida* (U112), Candidatus Methanoplasma *termitum* or *Eubacterium eligens*, or a first complementary domain derived therefrom.

Selectively, the first complementary domain may include an additional base sequence which does not undergo complementary bonding with the second complementary domain.

Here, the additional base sequence may be a 1 to 15-base sequence. For example, the additional base sequence may be a 1 to 5, 5 to 10, or 10 to 15-base sequence.

Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be or include a 5 to 35-base sequence. For example, the second complementary domain may be a 5, 6, 7, 8, 9, 10, 11, 12, 13, 14, 15, 16, 17, 18, 19, 20, 21, 22, 23, 24 or 25-base sequence.

The second complementary domain may have homology with a natural second complementary domain, or may be derived from the natural second complementary domain. In addition, the second complementary domain may have a difference in base sequence of the second complementary domain according to a species existing in nature, and may be derived from second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), Candidatus Methanoplasma termitum or *Eubacterium eligens*, or a second complementary domain derived therefrom.

Selectively, the second complementary domain may include an additional base sequence which does not undergo complementary bonding with the first complementary domain.

Here, the additional base sequence may be a 1 to 15-base sequence. For example, the additional base sequence may be a 1 to 5, 5 to 10, or 10 to 15-base sequence.

Linker Domain

Selectively, the linker domain is a nucleic acid sequence connecting a first complementary domain with a second complementary domain to produce single-stranded gRNA. Here, the linker domain may be connected with the first complementary domain and the second complementary domain, or may connect the first and second complementary domains by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

Selectively, a part or all of the base sequence of the guide domain, the first complementary domain, the second complementary domain and the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the single-stranded gRNA may consist of 5'-[second complementary domain]-[first complementary domain]-[guide domain]-3' or 5'-[second complementary domain]-[linker domain]-[first complementary domain]-[guide domain]-3' as described above.

In addition, the single-stranded gRNA may selectively include an additional base sequence.

In one exemplary embodiment, the single-stranded gRNA may be

5'-$(Z)_n$-$(Q)_m$-$(N_{target})$-3'; or

5'-$(X)_a$—$(Z)_h$—$(X)_b$-$(Q)_m$-$(X)_c$—$(N_{target})$-3'.

In another embodiment, the single-stranded gRNA may be

5'-$(Z)_h$-$(L)_j$-$(Q)_m$-$(N_{target})$-3'; or

5'-$(X)_a$—$(Z)_n$-$(L)_j$-$(Q)_m$-$(X)_c$—$(N_{target})$-3'.

Here, the $N_{target}$ is a base sequence capable of forming a complementary bond with a target sequence on a target gene or nucleic acid, and a base sequence region which may be changed according to a target sequence on a target gene or nucleic acid.

In one exemplary embodiment, $N_{target}$ may be a base sequence capable of forming a complementary bond with a target gene, that is, a target sequence of a PMP22 gene.

The $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of Parcubacteria bacterium or a first complementary domain derived therefrom, the $(Q)_m$ may be 5'-UUUGUAGAU-3' (SEQ ID NO: 154), or a base sequence having at least 50% or more homology with 5'-UUUGUAGAU-3' (SEQ ID NO: 154).

The $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of Parcubacteria bacterium or a Parcubacteria bacterium-derived second complementary domain, the $(Z)_h$ may be 5'-AAAUUUCUACU-3' (SEQ ID NO: 160), or a base sequence having at least 50% or more homology with 5'-AAAUUUCUACU-3' (SEQ ID NO: 160).

In addition, the (L) j is a base sequence including the linker domain, which connects the first complementary domain with the second complementary domain. Here, the L may be each independently selected from the group consisting of A, U, C and G, and the j may be the number of bases, which is an integer of 1 to 30.

In addition, each of the $(X)_a$, $(X)_b$ and $(X)_c$ is selectively an additional base sequence, where the X may be each independently selected from the group consisting of A, U, C and G, and the a, b and c may be the number of bases, which is 0 or an integer of 1 to 20.

2. Editor Protein

An editor protein refers to a peptide, polypeptide or protein which is able to directly bind to or interact with, without direct binding to, a nucleic acid.

The nucleic acid may be a nucleic acid contained in a target nucleic acid, gene or chromosome.

The nucleic acid may be a guide nucleic acid.

The editor protein may be an enzyme.

The editor protein may be a fusion protein.

Here, the fusion protein refers to a protein produced by fusing an enzyme with an additional domain, peptide, polypeptide or protein.

The enzyme refers to a protein including a domain which is able to cleave a nucleic acid, gene, chromosome or protein.

The enzyme may be a nuclease, protease or restriction enzyme.

The additional domain, peptide, polypeptide or protein may be a functional domain, peptide, polypeptide or protein, which has a function the same as or different from the enzyme.

The fusion protein may include an additional domain, peptide, polypeptide or protein at one or more of an N-terminus of an enzyme or the proximity thereof; a C-terminus of the enzyme or the proximity thereof; the middle region of an enzyme; and a combination thereof.

The fusion protein may include a functional domain, peptide, polypeptide or protein at one or more of an N-terminus of an enzyme or the proximity thereof; a C-terminus of the enzyme or the proximity thereof; the middle region of an enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV (SEQ ID NO: 188); NLS derived from nucleoplasmin (e.g., nucleoplasmin bipartite NLS with a sequence KRPAATKKAGQAKKKK (SEQ ID NO: 169)); c-myc NLS with an amino acid sequence PAAKRVKLD (SEQ ID NO: 189) or RQRRNELKRSP (SEQ ID NO: 170); hRNPA1 M9 NLS with a sequence NQSSNFGPMKGGNFGGRSSGPYGGGGQYFAKPRNQGGY (SEQ ID NO: 171); an importin-α-derived IBB domain sequence RMRIZFKNKGKDTAELRRRVEVSVELRKAKKDEQILKRRNV (SEQ ID NO: 172); myoma T protein sequences VSRKRPRP (SEQ ID NO: 190) and PPKKARED (SEQ ID NO: 191); human p53 sequence PQPKKKPL (SEQ ID NO: 196); a mouse c-abl IV sequence SALIKKKKKMAP (SEQ ID NO: 173); influenza virus NS1 sequences DRLRR (SEQ ID NO: 197) and PKQKKRK (SEQ ID NO: 198); a hepatitis virus-δ antigen sequence RKLKKKIKKL (SEQ ID NO: 174); a mouse Mx1 protein sequence REKKKFLKRR (SEQ ID NO: 175); a human poly(ADP-ribose) polymerase sequence KRKGDEVDGVDEVAKKKSKK (SEQ ID NO: 176); or steroid hormone receptor (human) glucocorticoid sequence RKCLQAGMNLEARKTKK (SEQ ID NO: 177), but the present invention is not limited thereto.

The editor protein may include a complete active enzyme.

Here, the "complete active enzyme" refers to an enzyme having the same function as a function of a wild-type enzyme, and for example, the wild-type enzyme cleaving the double strand of DNA has complete enzyme activity of entirely cleaving the double strand of DNA.

In addition, the complete active enzyme includes an enzyme having an improved function compared to the function of the wild-type enzyme, and for example, a specific modification or manipulation type of the wild-type enzyme cleaving the double strand of DNA has full enzyme activity which is improved compared to the wild-type enzyme, that is, activity of cleaving the double strand of DNA.

The editor protein may include an incomplete or partially active enzyme.

Here, the "incomplete or partially active enzyme" refers to an enzyme having some of the functions of the wild-type enzyme, and for example, a specific modification or manipulation type of the wild-type enzyme cleaving the double strand of DNA has incomplete or partial enzyme activity of cleaving a part of the double strand, that is, a single strand of DNA.

The editor protein may include an inactive enzyme.

Here, the "inactive enzyme" refers to an enzyme in which the function of a wild-type enzyme is completely inactivated. For example, a specific modification or manipulation type of the wild-type enzyme cleaving the double strand of DNA has inactivity so as not to completely cleave the DNA double strand.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

As one exemplary embodiment of the editor protein of the present invention, a CRISPR enzyme will be described below.

CRISPR Enzyme

The term "CRISPR enzyme" is a main protein component of a CRISPR-Cas system, and forms a complex with gRNA, resulting in the CRISPR-Cas system.

The CRISPR enzyme is a nucleic acid or polypeptide (or a protein) having a sequence encoding the CRISPR enzyme, and representatively, a Type II CRISPR enzyme or Type V CRISPR enzyme is widely used.

The Type II CRISPR enzyme is Cas9, which may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina,* Burkholderiales bacterium, *Polaromonas naphthalenivorans, Polaromonas* sp., Crocosphaera watsonii, Cyanothece sp., *Microcystis aeruginosa, Synechococcus* sp., *Acetohalobium arabaticum, Ammonifex degensii,* Caldicelulosiruptor becscii, Candidatus Desulforudis, *Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* and Acaryochloris marina.

The term "Cas9" is an enzyme which binds to gRNA so as to cleave or modify a target sequence or position on a target gene or nucleic acid, and may consist of an HNH domain capable of cleaving a nucleic acid strand forming a complementary bond with gRNA, an RuvC domain capable of cleaving a nucleic acid strand forming a complementary bond with gRNA, an REC domain recognizing a target and a Pi domain recognizing PAM. Hiroshi Nishimasu et al. (2014) Cell 156:935-949 may be referenced for specific structural characteristics of Cas9.

In addition, the Type V CRISPR enzyme may be Cpf1, which may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium,* Corynebacter, *Carnobacterium, Listeria, Rhodobacter, Paludibacter, Clostridium,* Lachnospiraceae, Clostridiaridium, *Leptotrichia, Francisella, Legionella, Alicyclobacillus, Methanomethyophilus, Porphyromonas, Prevotella,* Bacteroidetes, *Helcococcus, Leptospira, Desulfovibrio, Desulfonatronum,* Opitutaceae, *Tuberibacillus, Bacillus, Brevibacillus, Methylobacterium* or *Acidaminococcus.*

The Cpf1 may consist of an RuvC domain similar and corresponding to the RuvC domain of Cas9, an Nuc domain without the HNH domain of Cas9, an REC domain recognizing a target, a WED domain and a PI domain recognizing PAM. For specific structural characteristics of Cpf1, Takashi Yamano et al. (2016) Cell 165:949-962 may be referenced.

The CRISPR enzyme of the Cas9 or Cpf1 protein may be isolated from a microorganism existing in nature or non-naturally produced by a recombinant or synthetic method.

Type II CRISPR Enzyme

The crystal structure of the type II CRISPR enzyme was determined according to studies on two or more types of natural microbial type II CRISPR enzyme molecules (Jinek et al., Science, 343 (6176): 1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, or the HNH domain is used to include HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII. For example, in the case of SpCas9, the RuvC domain is assembled from each of three divided RuvC domains (RuvC I, RuvCII and RuvCIII) located at the sequences of amino acids 1 to 59, 718 to 769 and 909 to 1098 of SpCas9, respectively.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs. For example, in the case of SpCas9, the HNH domain is located at amino acid sequence 775 to 908 of SpCas9.

The PI domain recognizes a specific base sequence in a target gene or nucleic acid, that is, a protospacer adjacent motif (PAM) or interacts with PAM. For example, in the case of SpCas9, the PI domain is located at the sequence of amino acids 1099 to 1368 of SpCas9.

Here, the PAM may vary according to the origin of the type II CRISPR enzyme. For example, when the CRISPR enzyme is SpCas9, PAM may be 5'-NGG-3', when the CRISPR enzyme is *Streptococcus thermophilus* Cas9 (StCas9), PAM may be 5'-NNAGAAW-3' (W=A or T) (SEQ ID NO: 192), when the CRISPR enzyme is *Neisseria meningitides* Cas9 (NmCas9), PAM may be 5'-NNNN-GATT-3' (SEQ ID NO: 193), and when the CRISPR enzyme is *Campylobacter jejuni* Cas9 (CjCas9), PAM may be 5'-NNNVRYAC-3' (SEQ ID NO: 194) (V=G or C or A, R=A or G, Y=C or T), where the N may be A, T, G or C; or A, U, G or C.

Type V CRISPR Enzyme

Type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence.

The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species.

In one example, the PAM sequence recognized by Cpf1 may be 5'-TTN-3' (N is A, T, C or G).

CRISPR Enzyme Activity

A CRISPR enzyme cleaves a double or single strand of a target gene or nucleic acid, and has nuclease activity causing breakage or deletion of the double or single strand. Generally, the wild-type type II CRISPR enzyme or type V CRISPR enzyme cleaves the double strand of the target gene or nucleic acid.

To manipulate or modify the above-described nuclease activity of the CRISPR enzyme, the CRISPR enzyme may be manipulated or modified, such a manipulated or modified CRISPR enzyme may be modified into an incompletely or partially active or inactive enzyme.

Incompletely or Partially Active Enzyme

A CRISPR enzyme modified to change enzyme activity, thereby exhibiting incomplete or partial activity is called a nickase.

The term "nickase" refers to a CRISPR enzyme manipulated or modified to cleave only one strand of the double strand of the target gene or nucleic acid, and the nickase has nuclease activity of cleaving a single strand, for example, a strand that is not complementary or complementary to gRNA of the target gene or nucleic acid. Therefore, to cleave the double strand, nuclease activity of the two nickases is needed.

For example, the nickase may have nuclease activity by the RuvC domain. That is, the nickase may include nuclease activity of the HNH domain, and to this end, the HNH domain may be manipulated or modified.

In one example, provided that the CRISPR enzyme is the type II CRISPR enzyme, in one exemplary embodiment, when the residue 840 in the amino acid sequence of SpCas9 is mutated from histidine to alanine, the nuclease activity of the HNH domain is inactivated to be used as a nickase. Since the nickase produced thereby has nuclease activity of the RuvC domain, it is able to cleave a non-complementary strand of the target gene or nucleic acid, that is, a strand that does not form a complementary bond with gRNA.

In another exemplary embodiment, when the residue 559 in the amino acid sequence of CjCas9 is mutated from histidine to alanine, the nuclease activity of the HNH domain is inactivated to be used as a nickase. The nickase produced thereby has nuclease activity by the RuvC domain, and thus is able to cleave a non-complementary strand of the target gene or nucleic acid, that is, a strand that does not form a complementary bond with gRNA.

For example, the nickase may have nuclease activity by the HNH domain. That is, the nickase may include the nuclease activity of the RuvC domain, and to this end, the RuvC domain may be manipulated or modified.

In one example, provided that the CRISPR enzyme is the type II CRISPR enzyme, in one exemplary embodiment, when the residue 10 in the amino acid sequence of SpCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

In another exemplary embodiment, when the residue 8 in the amino acid sequence of CjCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

Inactive Enzyme

A CRISPR enzyme which is modified to make enzyme activity completely inactive is called an inactive CRISPR enzyme.

The term "inactive CRISPR enzyme" refers to a CRISPR enzyme which is modified not to completely cleave the double strand of the target gene or nucleic acid, and the inactive CRISPR enzyme has nuclease inactivity due to the mutation in the domain with nuclease activity of the wild-type CRISPR enzyme. The inactive CRISPR enzyme may be one in which the nuclease activities of the RuvC domain and the HNH domain are inactivated.

For example, the inactive CRISPR enzyme may be manipulated or modified in the RuvC domain and the HNH domain so as to inactive nuclease activity.

In one example, provided that the CRISPR enzyme is the type II CRISPR enzyme, in one exemplary embodiment, when the residues 10 and 840 in the amino acid sequence of SpCas9 are mutated from aspartic acid and histidine to alanine, respectively, nuclease activities by the RuvC domain and the HNH domain are inactivated, such that the double strand may not cleave completely the double strand of the target gene or nucleic acid.

In another exemplary embodiment, when the residues 8 and 559 in the amino acid sequence of CjCas9 are mutated from aspartic acid and histidine to alanine, the nuclease activities by the RuvC domain and the HNH domain are inactivated, such that the double strand may not cleave completely the double strand of the target gene or nucleic acid.

Other Activities

The CRISPR enzyme may have endonuclease activity, exonuclease activity or helicase activity, that is, an ability to anneal the helix structure of the double-stranded nucleic acid, in addition to the above-described nuclease activity.

In addition, the CRISPR enzyme may be modified to completely, incompletely, or partially activate the endonuclease activity, exonuclease activity or helicase activity.

Targeting of CRISPR Enzyme

The CRISPR enzyme may interact with gRNA, thereby forming a gRNA-CRISPR enzyme complex, that is, a CRISPR complex, and lead a guide sequence to approach a target sequence including a PAM sequence in cooperation with gRNA. Here, the ability of the CRISPR enzyme to interact with the target gene or nucleic acid is dependent on the PAM sequence.

The PAM sequence is a sequence present in the target gene or nucleic acid, which may be recognized by the PI domain of the CRISPR enzyme. The PAM sequence may vary depending on the origin of the CRISPR enzyme. That is, there are various PAM sequences which are able to be specifically recognized according to species.

In one example, provided that the CRISPR enzyme is the type II CRISPR enzyme,
    in the case of SpCas9, the PAM sequence may be 5'-NGG-3', 5'-NAG-3' and/or 5'-NGA-3', in the case of StCas9, the PAM sequence may be 5'-NGGNG-3' and/or 5'-NNAGAAW-3' (W=A or T), in the case of NmCas9, the PAM sequence may be 5'-NNNNGATT-3' (SEQ ID NO: 193) and/or 5'-NNNGCTT-3' (SEQ ID NO: 195), in the case of CjCas9, the PAM sequence may be 5'-NNNVRYAC-3' (V=G, C or A; R=A or G; Y=C or T) (SEQ ID NO: 194), in the case of *Streptococcus mutans* Cas9 (SmCas9), the PAM sequence may be 5'-NGG-3' and/or 5'-NAAR-3' (R=A or G), and in the case of *Staphylococcus aureus* Cas9 (SaCas9), the PAM sequence may be 5'-NNGRR-3', 5'-NNGRRT-3' (SEQ ID NO: 199) and/or 5'-NNGRRV-3' (SEQ ID NO: 200) (R=A or G; V=G, C or A).

In another example, provided that the CRISPR enzyme is the type V CRISPR enzyme, in the case of Cpf1, the PAM sequence may be 5'-TTN-3'. Here, the N may be A, T, G or C; or A, U, G or C.

The CRISPR enzyme capable of recognizing a specific PAM sequence may be manipulated or modified using the PAM sequence capable of being specifically recognized according to species. For example, the PI domain of SpCas9 may be replaced with the PI domain of CjCas9 so as to have the nuclease activity of SpCas9 and recognize a CjCas9-specific PAM sequence, thereby producing SpCas9 recognizing the CjCas9-specific PAM sequence. A specifically recognized PAM sequence may be changed by substitution or replacement of the PI domain.

CRISPR Enzyme Mutant

The CRISPR enzyme may be modified to improve or inhibit various characteristics such as nuclease activity, helicase activity, an ability to interact with gRNA, and an ability to approach the target gene or nucleic acid, for example, PAM recognizing ability of the CRISPR enzyme.

In addition, the CRISPR enzyme mutant may be a CRISPR enzyme which interacts with gRNA to form a gRNA-CRISPR enzyme complex, that is, a CRISPR complex, and is modified or manipulated to improve target specificity, when approaching or localized to the target gene or nucleic acid, such that only a double or single strand of the target gene or nucleic acid is cleaved without cleavage of a double or single strand of a non-target gene or nucleic acid which partially forms a complementary bond with gRNA and a non-target gene or nucleic acid which does not form a complementary bond therewith.

Here, an effect of cleaving the double or single strand of the non-target gene or nucleic acid partially forming a complementary bond with gRNA and the non-target gene or nucleic acid not forming a complementary bond therewith is referred to as an off-target effect, a position or base sequence of the non-target gene or nucleic acid partially forming a complementary bond with gRNA and the non-target gene or nucleic acid not forming a complementary bond therewith is referred to as an off-target. Here, there may be one or more off-targets. One the other hand, the cleavage effect of the double or single strand of the target gene or nucleic acid is referred to as an on-target effect, and a location or target sequence of the target gene or nucleic acid is referred to as an on-target.

The CRISPR enzyme mutant is modified in at least one of the amino acids of a naturally-occurring CRISPR enzyme, and may be modified, for example, improved or inhibited in one or more of the various characteristics such as nuclease activity, helicase activity, an ability to interact with gRNA, an ability to approach the target gene or nucleic acid and target specificity, compared to the unmodified CRISPR enzyme. Here, the modification may be substitution, removal, addition of an amino acid, or a mixture thereof.

In the CRISPR enzyme mutant, the modification may be a modification of one or two or more amino acids located in a region consisting of amino acids having positive charges, present in the naturally-occurring CRISPR enzyme.

For example, the modification may be a modification of one or two or more amino acids of the positively-charged amino acids such as lysine (K), arginine (R) and histidine (H), present in the naturally-occurring CRISPR enzyme.

The modification may be a modification of one or two or more amino acids located in a region composed of non-positively-charged amino acids present in the naturally-occurring CRISPR enzyme.

For example, the modification may be a modification of one or two or more amino acids of the non-positively-charged amino acids, that is, aspartic acid (D), glutamic acid (E), serine(S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In another example, the modification may be a modification of one or two or more amino acids of non-charged amino acids, that is, serine(S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one or two or more of the amino acids having hydrophobic residues present in the naturally-occurring CRISPR enzyme.

For example, the modification may be a modification of one or two or more amino acids of glycine (G), alanine (A), valine (V), isoleucine (I), leucine (L), methionine (M), phenylalanine (F), tyrosine (Y) and tryptophan (W), present in the naturally-occurring CRISPR enzyme.

The modification may be a modification of one or two or more of the amino acids having polar residues, present in the naturally-occurring CRISPR enzyme.

For example, the modification may be a modification of one or two or more amino acids of serine(S), threonine (T), asparagine (N), glutamine (Q), cysteine (C), proline (P), lysine (K), arginine (R), histidine (H), aspartic acid (D) and glutamic acid (E), present in the naturally-occurring CRISPR enzyme.

In addition, the modification may be a modification of one or two or more of the amino acids including lysine (K), arginine (R) and histidine (H), present in the naturally-occurring CRISPR enzyme.

For example, the modification may be a substitution of one or two or more of the amino acids including lysine (K), arginine (R) and histidine (H), present in the naturally-occurring CRISPR enzyme.

The modification may be a modification of one or two or more of the amino acids including aspartic acid (D) and glutamic acid (E), present in the naturally-occurring CRISPR enzyme.

For example, the modification may be a substitution of one or two or more of the amino acids including aspartic acid (D) and glutamic acid (E), present in the naturally-occurring CRISPR enzyme.

The modification may be a modification of one or two or more of the amino acids including serine(S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

For example, the modification may be a substitution of one or two or more of the amino acid including serine(S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one, two, three, four, five, six, seven or more of the amino acids present in the naturally-occurring CRISPR enzyme.

In addition, in the CRISPR enzyme mutant, the modification may be a modification of one or two or more of the amino acids present in the RuvC domain of the CRISPR enzyme. Here, the RuvC domain may be an RuvCI, RuvCII or RuvCIII domain.

The modification may be a modification of one or two or more of the amino acids present in the HNH domain of the CRISPR enzyme.

The modification may be a modification of one or two or more of the amino acids present in the REC domain of the CRISPR enzyme.

The modification may be one or two or more of the amino acids present in the PI domain of the CRISPR enzyme.

The modification may be a modification of two or more of the amino acids contained in at least two or more domains of the REC, RuvC, HNH and PI domains of the CRISPR enzyme.

In one example, the modification may be a modification of two or more of the amino acids contained in the REC and RuvC domains of the CRISPR enzyme.

In one exemplary embodiment, in the SpCas9 mutant, the modification may be a modification of at least two or more of the A203, H277, G366, F539, I601, M763, D965 and F1038 amino acids contained in the REC and RuvC domains of SpCas9.

In another example, the modification may be a modification of two or more of the amino acids contained in the REC and HNH domains of the CRISPR enzyme.

In one exemplary embodiment, in the SpCas9 mutant, the modification may be a modification of at least two or more of the A203, H277, G366, F539, I601 and K890 amino acids contained in the REC and HNH domains of SpCas9.

In one example, the modification may be a modification of two or more of the amino acids contained in the REC and PI domains of the CRISPR enzyme.

In one exemplary embodiment, in the SpCas9 mutant, the modification may be a modification of at least two or more of the A203, H277, G366, F539, I601, T1102 and D1127 amino acids contained in the REC and PI domains of SpCas9.

In another example, the modification may be a modification of three or more of the amino acids contained in the REC, RuvC and HNH domains of the CRISPR enzyme.

In one exemplary embodiment, in the SpCas9 mutant, the modification may be a modification of at least three or more of the A203, H277, G366, F539, I601, M763, K890, D965 and F1038 amino acids contained in the REC, RuvC and HNH domains of SpCas9.

In one example, the modification may be a modification of three or more of the amino acids contained in the REC, RuvC and PI domains contained in the CRISPR enzyme.

In one exemplary embodiment, in the SpCas9 mutant, the modification may be a modification of at least three or more of the A203, H277, G366, F539, I601, M763, D965, F1038, T1102 and D1127 amino acids contained in the REC, RuvC and PI domains of SpCas9.

In another example, the modification may be a modification of three or more of the amino acids contained in the REC, HNH and PI domains of the CRISPR enzyme.

In one exemplary embodiment, in the SpCas9 mutant, the modification may be a modification of at least three or more of the A203, H277, G366, F539, I601, K890, T1102 and D1127 amino acids contained in the REC, HNH and PI domains of SpCas9.

In one example, the modification may be a modification of three or more of the amino acids contained in the RuvC, HNH and PI domains of the CRISPR enzyme.

In one exemplary embodiment, in the SpCas9 mutant, the modification may be a modification of at least three or more of the M763, K890, D965, F1038, T1102 and D1127 amino acids contained in the RuvC, HNH and PI domains of SpCas9.

In another example, the modification may be a modification of four or more of the amino acids contained in the REC, RuvC, HNH and PI domains of the CRISPR enzyme.

In one exemplary embodiment, in the SpCas9 mutant, the modification may be a modification of at least four or more of the A203, H277, G366, F539, I601, M763, K890, D965, F1038, T1102 and D1127 amino acids contained in the REC, RuvC, HNH and PI domains of SpCas9.

In addition, in the CRISPR enzyme mutant,
the modification may be a modification of one or two or more of the amino acids participating in the nuclease activity of the CRISPR enzyme.

For example, in the SpCas9 mutant, the modification may be a modification of one or two or more of the group consisting of the amino acids D10, E762, H840, N854, N863 and D986, or one or two or more of the group consisting of the amino acids corresponding to other Cas9 orthologs.

The modification may be a modification for partially inactivating the nuclease activity of the CRISPR enzyme, and such a CRISPR enzyme mutant may be a nickase.

Here, the modification may be a modification for inactivating the nuclease activity of the RuvC domain of the CRISPR enzyme, and such a CRISPR enzyme mutant may not cleave a non-complementary strand of a target gene or nucleic acid, that is, a strand which does not form a complementary bond with gRNA.

In one exemplary embodiment, in the case of SpCas9, when residue 10 of the amino acid sequence of SpCas9 is mutated from aspartic acid to alanine, that is, when mutated to D10A, the nuclease activity of the RuvC domain is inactivated, and thus the SpCas9 may be used as a nickase. The nickase produced thereby may not cleave a non-complementary strand of the target gene or nucleic acid, that is, a strand that does not form a complementary bond with gRNA.

In another exemplary embodiment, in the case of CjCas9, when residue 8 of the amino acid sequence of CjCas9 is mutated from aspartic acid to alanine, that is, when mutated to D8A, the nuclease activity of the RuvC domain is inactivated, and thus the CjCas9 may be used as a nickase. The nickase produced thereby may not cleave a non-complementary strand of the target gene or nucleic acid, that is, a strand that does not form a complementary bond with gRNA.

In addition, here, the modification may be a modification for inactivating the nuclease activity of the HNH domain of the CRISPR enzyme, and such a CRISPR enzyme mutant may not cleave a complementary strand of the target gene or nucleic acid, that is, a strand forming a complementary bond with gRNA.

In one exemplary embodiment, in the case of SpCas9, when residue 840 of the amino acid sequence of SpCas9 is mutated from histidine to alanine, that is, when mutated to H840A, the nuclease activity of the HNH domain is inactivated, and thus the SpCas9 may be used as a nickase. The nickase produced thereby may not cleave a complementary strand of the target gene or nucleic acid, that is, a strand that forms a complementary bond with gRNA.

In another exemplary embodiment, in the case of CjCas9, when residue 559 of the amino acid sequence of CjCas9 is mutated from histidine to alanine, that is, when mutated to H559A, the nuclease activity of the HNH domain is inactivated, and thus the CjCas9 may be used as a nickase. The nickase produced thereby may not cleave a complementary strand of the target gene or nucleic acid, that is, a strand that forms a complementary bond with gRNA.

In addition, the modification may be a modification for completely inactivating the nuclease activity of the CRISPR enzyme, and such a CRISPR enzyme mutant may be an inactive CRISPR enzyme.

Here, the modification may be a modification for inactivating the nuclease activities of the RuvC and HNH domains of the CRISPR enzyme, and such a CRISPR enzyme mutant may does not cleave a double strand of the target gene or nucleic acid.

In one exemplary embodiment, in the case of SpCas9, when the residues 10 and 840 in the amino acid sequence of SpCas9 are mutated from aspartic acid and histidine to alanine, that is, mutated to D10A and H840A, respectively, the nuclease activities of the RuvC domain and the HNH domain are inactivated, the double strand of the target gene or nucleic acid may not be completely cleaved.

In another exemplary embodiment, in the case of CjCas9, when residues 8 and 559 of the amino acid sequence of CjCas9 are mutated from aspartic acid and histidine to alanine, that is, mutated to D8A and H559A, respectively, the nuclease activities by the RuvC and HNH domains are inactivated, and thus the double strand of the target gene or nucleic acid may not be completely cleaved.

In addition, the CRISPR enzyme mutant may further include an optionally functional domain, in addition to the innate characteristics of the CRISPR enzyme, and such a CRISPR enzyme mutant may have an additional characteristic in addition to the innate characteristics.

Here, the functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The functional domain, peptide, polypeptide or protein may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in base repair or editing of C into T or U, or G into A.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) 3-galactosidase, 3-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain may be a nuclear localization sequence or signal (NLS) or a nuclear export sequence or signal (NES).

In one example, the CRISPR enzyme may include one or more NLSs. Here, one or more NLSs may be included at an N-terminus of an CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV (SEQ ID NO: 188); NLS from nucleoplasmin (e.g., nucleoplasmin bipartite NLS having the sequence KRPAATKKAGQAKKKK) (SEQ ID NO: 169); c-myc NLS having the amino acid sequence PAAKRVKLD (SEQ ID NO: 189) or RQRRNELKRSP (SEQ ID NO: 170); hRNPA1 M9 NLS having the sequence NQSSNFGPMKGGNFG-GRSSGPYGGGGQYFAKPRNQGGY (SEQ ID NO: 171); the sequence RMRIZFKNKGKDTAELRRRRVEVS-VELRKAKKDEQILKRRNV (SEQ ID NO: 172) of the IBB domain from importin-α; the sequences VSRKRPRP (SEQ ID NO: 190) and PPKKARED (SEQ ID NO: 191) of a myoma T protein; the sequence PQPKKKPL (SEQ ID NO: 196) of human p53; the sequence SALIKKKKKMAP (SEQ ID NO: 173) of mouse c-abl IV; the sequences DRLRR (SEQ ID NO: 197) and PKQKKRK (SEQ ID NO: 198) of influenza virus NS1; the sequence RKLKKKIKKL (SEQ ID NO: 174) of a hepatitis delta virus antigen; the sequence REKKKFLKRR (SEQ ID NO: 175) of a mouse Mx1 protein; the sequence KRKGDEVDGVDEVAKKKSKK (SEQ ID NO: 1176) of a human poly(ADP-ribose) polymerase; or the NLS sequence RKCLQAGMNLEARKTKK (SEQ ID NO: 177), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

Here, the split-type CRISPR enzyme may be a completely, incompletely or partially active enzyme or inactive enzyme.

For example, the SpCas9 may be divided into two parts between the residue 656, tyrosine, and the residue 657, threonine, thereby generating split SpCas9.

In addition, the split-type CRISPR enzyme may selectively include an additional domain, peptide, polypeptide or protein for reconstitution.

Here, the "reconstitution" refers to formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

3. Target Sequence

The term "target sequence" is a base sequence present in a target gene or nucleic acid, and has complementarity to a guide sequence contained in a guide domain of a guide nucleic acid. The target sequence is a base sequence which may vary according to a target gene or nucleic acid, that is, a subject for gene manipulation or correction, which may be designed in various forms according to the target gene or nucleic acid.

The target sequence may form a complementary bond with the guide sequence contained in the guide domain of the guide nucleic acid, and a length of the target sequence may be the same as that of the guide sequence.

The target sequence may be a 5 to 50-base sequence.

In an embodiment, the target sequence may be a 16, 17, 18, 19, 20, 21, 22, 23, 24 or 25-base sequence.

The target sequence may be a nucleic acid sequence complementary to the guide sequence contained in the guide domain of the guide nucleic acid, which has, for example, at least 70%, 75%, 80%, 85%, 90% or 95% or more complementarity or complete complementarity.

In one example, the target sequence may be or include a 1 to 8-base sequence, which is not complementary to the guide sequence contained in the guide domain of the guide nucleic acid.

In addition, the target sequence may be a base sequence adjacent to a nucleic acid sequence that is able to be recognized by an editor protein.

In one example, the target sequence may be a continuous 5 to 50-base sequence adjacent to the 5' end and/or 3' end of the nucleic acid sequence that is able to be recognized by the editor protein.

In one exemplary embodiment, target sequences for a gRNA-CRISPR enzyme complex will be described below.

When the target gene or nucleic acid is targeted by the gRNA-CRISPR enzyme complex, the target sequence has complementarity to the guide sequence contained in the guide domain of gRNA. The target sequence is a base sequence which varies according to the target gene or nucleic acid, that is, a subject for gene manipulation or correction, which may be designed in various forms according to the target gene or nucleic acid.

In addition, the target sequence may be a base sequence adjacent to a PAM sequence which is able to be recognized by the CRISPR enzyme, that is, Cas9 or Cpf1.

In one example, the target sequence may be a continuous 5 to 50-base sequence adjacent to the 5' end and/or 3' end of the PAM sequence which is recognized by the CRISPR enzyme.

In one exemplary embodiment, when the CRISPR enzyme is SpCas9, the target sequence may be a continuous 16 to 25-base sequence adjacent to the 5' end and/or 3' end of a 5'-NGG-3', 5'-NAG-3' and/or 5'-NGA-3' (N=A, T, G or C; or A, U, G or C) sequence.

In another exemplary embodiment, when the CRISPR enzyme is StCas9, the target sequence may be a continuous 16 to 25-base sequence adjacent to the 5' end and/or 3' end of a 5'-NGGNG-3' and/or 5'-NNAGAAW-3' (W=A or T, and N=A, T, G or C; or A, U, G or C) sequence (SEQ ID NO: 192).

In still another exemplary embodiment, when the CRISPR enzyme is NmCas9, the target sequence may be a continuous 16 to 25-base sequence adjacent to the 5' end and/or 3' end of a 5'-NNNNGATT-3' (SEQ ID NO: 193) and/or 5'-NNNGCTT-3' (SEQ ID NO: 195) (N=A, T, G or C; or A, U, G or C) sequence.

In one exemplary embodiment, when the CRISPR enzyme is CjCas9, the target sequence may be a continuous 16 to 25-base sequence adjacent to the 5' end and/or 3' end of a 5'-NNNVRYAC-3' (SEQ ID NO: 194) (V=G, C or A; R=A or G, Y=C or T, N=A, T, G or C; or A, U, G or C) sequence.

In another exemplary embodiment, when the CRISPR enzyme is SmCas9, the target sequence may be a continuous 16 to 25-base sequence adjacent to the 5' end and/or 3' end of a 5'-NGG-3' and/or 5'-NAAR-3' (R=A or G, N=A, T, G or C; or A, U, G or C) sequence.

In yet another exemplary embodiment, when the CRISPR enzyme is SaCas9, the target sequence may be a continuous 16 to 25-base sequence adjacent to the 5' end and/or 3' end of a 5'-NNGRR-3', 5'-NNGRRT-3' (SEQ ID NO: 199) and/or 5'-NNGRRV-3' (SEQ ID NO: 200) (R=A or G, V=G, C or A, N=A, T, G or C; or A, U, G or C) sequence.

In one exemplary embodiment, when the CRISPR enzyme is Cpf1, the target sequence may be a continuous 16 to 25-base sequence adjacent to the 5' end and/or 3' end of a 5'-TTN-3' (N=A, T, G or C; or A, U, G or C) sequence.

In one exemplary embodiment of the present invention, the target sequence may be a nucleic acid sequence contained in the PMP22 gene.

Alternatively, the target sequence may be a partial nucleic acid sequence of the PMP22 gene.

Alternatively, the target sequence may be a nucleic acid sequence of the coding or non-coding region or a mixture thereof of the PMP22 gene.

Alternatively, the target sequence may be a nucleic acid sequence of the Promoter, TATA Box, CAAT Box, Initiation Site, Termination Site, Donor Splice Site, Acceptor Splice Site, Poly A Site, Enhancer, 3' UTR (Untranslated Region), 5' UTR, Attenuator and GC Box or a mixture thereof of the PMP22 gene.

Alternatively, the target sequence may be a nucleic acid sequence of an exon, an intron or a mixture thereof of the PMP22 gene.

Alternatively, the target sequence may be a nucleic acid sequence including or adjacent to a mutated region (e.g., a region different from a wild-type gene) of the PMP22 gene.

Alternatively, the target sequence may be a continuous 5 to 50-nucleic acid sequence of the PMP22 gene.

As one exemplary embodiment of the present invention, the above target sequences of the PMP22 gene are summarized in Table 1, Table 2, Table 3, Table 4, Table 5, Table 6 and Table 7.

[SC Function-Controlling Factor-Manipulated Product]

4. Guide Nucleic Acid-Editor Protein Complex and Use Thereof

A guide nucleic acid-editor protein complex may modify a target.

The target may be a target nucleic acid, gene, chromosome or protein.

For example, the guide nucleic acid-editor protein complex may be used to ultimately regulate (e.g., inhibit, suppress, reduce, increase or promote) the expression of a protein of interest, remove a protein, regulate (e.g., inhibit, suppress, reduce, increase or promote) protein activity, or express a new protein.

Here, the guide nucleic acid-editor protein complex may act at a DNA, RNA, gene or chromosomal level.

For example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of the target DNA.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of target RNA.

In one example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target gene.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target chromosome.

The guide nucleic acid-editor protein complex may act at gene transcription and translation stages.

In one example, the guide nucleic acid-editor protein complex may promote or suppress the transcription of a target gene, thereby regulating (e.g., inhibiting, suppressing, reducing, increasing or promoting) the expression of a protein encoded by the target gene.

In another example, the guide nucleic acid-editor protein complex may promote or suppress the translation of a target gene, thereby regulating (e.g., inhibiting, suppressing, reducing, increasing or promoting) the expression of a protein encoded by the target gene.

The guide nucleic acid-editor protein complex may act at a protein level.

In one example, the guide nucleic acid-editor protein complex may manipulate or modify a target protein, thereby removing the target protein or regulating (e.g., inhibiting, suppressing, reducing, increasing or promoting) protein activity.

In one exemplary embodiment, the present invention provides a guide nucleic acid-editor protein complex used to manipulate a SC function-controlling factor, for example, a PMP22 gene. Preferably, a gRNA-CRISPR enzyme complex is provided.

Particularly, the present invention may provide gRNA including a guide domain capable of forming a complementary bond with a target sequence from a gene, for example, isolated or non-natural gRNA and DNA encoding the same. The gRNA and the DNA sequence encoding the same may be designed to be able to complementarily bind to a target sequence listed in Table 1, Table 2, Table 3, Table 4, Table 5, Table 6 and Table 7.

In addition, a target region of the gRNA is designed to provide a third gene, which has a nucleic acid modification, for example, double or single strand breaks; or a specific function at a target site in a PMP22 gene.

In addition, when two or more gRNAs are used to induce two or more cleaving events in a target gene, for example, a double or single strand break, the two or more cleaving events may occur due to the same or different Cas9 proteins.

The gRNA may target, for example, two or more regions of the PMP22 gene, and
  may independently induce the cleavage of a double strand and/or a single strand of the PMP22 gene, or
  may induce the insertion of one foreign nucleotide into a cleavage site of the PMP22 gene.

In addition, in another exemplary embodiment of the present invention, a nucleic acid constituting the guide nucleic acid-editor protein complex may include:
  (a) a sequence encoding a guide nucleic acid including a guide domain, which is complementary to a target sequence of the PMP22 gene as described herein; and
  (b) a sequence encoding an editor protein.

Here, there may be two or more of the (a) according to a target region, and the (b) may employ the same or two or more editor proteins.

In an embodiment, the nucleic acid may be designed to target an enzymatically active or partially active editor protein thereof to place it sufficiently adjacent to a knockout or a knockdown target site in order to reduce, decrease or inhibit expression of the PMP22 gene.

In another embodiment, the nucleic acid may be designed to target an enzymatically inactive editor protein or a fusion protein (e.g., a transcription repressor domain fusion) thereof to place it sufficiently adjacent to a knockdown target site in order to reduce, decrease or inhibit expression of the PMP22 gene.

Besides, it should be obvious that the above-described structure, function, and all applications of the guide nucleic acid-editor protein complex will be utilized in manipulation of the SC function-controlling factor, that is, the PMP22 gene.

Use of Guide Nucleic Acid-Editor Protein Complex

In an embodiment for the use of the guide nucleic acid-editor protein complex of the present invention, the manipulation or modification of target DNA, RNA, genes or chromosomes using the gRNA-CRISPR enzyme complex will be described below.

Gene Manipulation

A target gene or nucleic acid may be manipulated or corrected using the above-described gRNA-CRISPR enzyme complex, that is, the CRISPR complex. Here, the manipulation or correction of the target gene or nucleic acid includes all of the stages of i) cleaving or damaging the target gene or nucleic acid and ii) repairing the damaged target gene or nucleic acid.

i) Cleavage or Damage of Target Gene or Nucleic Acid i) The cleavage or damage of the target gene or nucleic acid may be cleavage or damage of the target gene or nucleic acid using the CRISPR complex, and particularly, cleavage or damage of a target sequence in the target gene or nucleic acid.

In one example, the cleavage or damage of the target gene or nucleic acid using the CRISPR complex may be complete cleavage or damage to the double strand of a target sequence.

In one exemplary embodiment, when wild-type SpCas9 is used, the double strand of a target sequence forming a complementary bond with gRNA may be completely cleaved.

In another exemplary embodiment, when SpCas9 nickase (D10A) and SpCas9 nickase (H840A) are used, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In still another exemplary embodiment, when SpCas9 nickase (D10A) and SpCas9 nickase (H840A), and two gRNAs having different target sequences are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), and the cleavages may take place sequentially or simultaneously.

In another example, the cleavage or damage of a target gene or nucleic acid using the CRISPR complex may be cleavage or damage to only the single strand of a target sequence. Here, the single strand may be a complementary single strand of a target sequence forming a complementary bond with gRNA, or a non-complementary single strand of the target sequence forming a complementary bond with gRNA.

In one exemplary embodiment, when SpCas9 nickase (D10A) is used, a complementary single strand of a target sequence forming a complementary bond with gRNA may be cleaved by the SpCas9 nickase (D10A), but a non-complementary single strand of the target sequence forming a complementary bond with gRNA may not be cleaved.

In another exemplary embodiment, when SpCas9 nickase (H840A) is used, a non-complementary single strand of a target sequence forming a complementary bond with gRNA may be cleaved by the SpCas9 nickase (H840A), but a complementary single strand of the target sequence forming a complementary bond with gRNA may not be cleaved.

In yet another example, the cleavage or damage of a target gene or nucleic acid using the CRISPR complex may be partial removal of a nucleic acid fragment.

In one exemplary embodiment, when two gRNAs having different target sequences and wild-type SpCas9 are used, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

In another exemplary embodiment, when two gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand may be cleaved by the SpCas9 nickase (H840A), resulting in the removal of nucleic acid fragments by the first and second gRNAs, the wild-type SpCas9, the SpCas9 nickase (D10A) and the SpCas9 nickase (H840A).

In still another exemplary embodiment, when two gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand may be cleaved by the SpCas9 nickase (H840A), a complementary double strand of a target sequence forming a complementary bond with the second gRNA may be cleaved by the SpCas9 nickase (D10A), and a non-complementary single strand may be cleaved by the SpCas9 nickase (H840A), resulting in the removal of nucleic acid fragments by the first and second gRNAs, the SpCas9 nickase (D10A) and the SpCas9 nickase (H840A).

In yet another exemplary embodiment, when three gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand of a target sequence forming a complementary bond with the third gRNA may be cleaved by the SpCas9 nickase (H840A), resulting in the removal of nucleic acid fragments by the first gRNA, the second gRNA, the third gRNA, the wild-type SpCas9, the SpCas9 nickase (D10A) and the SpCas9 nickase (H840A).

In yet another exemplary embodiment, when four gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), a complementary single strand of a target sequence forming a complementary bond with the third gRNA may be cleaved by the SpCas9 nickase (D10A), and a non-complementary single strand of a target sequence forming a complementary bond with fourth gRNA may be cleaved by the SpCas9 nickase (H840A), resulting in the removal of nucleic acid fragments by the first gRNA, the second gRNA, the third gRNA, the fourth gRNA, the SpCas9 nickase (D10A) and the SpCas9 nickase (H840A).

ii) Repair or Restoration of Damaged Target Gene or Nucleic Acid

The target gene or nucleic acid cleaved or damaged by the CRISPR complex may be repaired or restored through NHEJ and homology-directed repairing (HDR).

Non-Homologous End Joining (NHEJ)

NHEJ is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutations in a significant functional domain are probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a gene targeted by the CRISPR complex may be performed using such NHEJ. A double strand or two single strands of a target gene or nucleic acid may be cleaved using the CRISPR enzyme such as Cas9 or Cpf1, and the broken double strand or two single strands of the target gene or nucleic acid may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

Homology Directed Repairing (HDR)

HDR is a correction method without an error, which uses a homologous sequence as a template to repair or restoration a damaged gene or nucleic acid, and generally, to repair or restoration broken DNA, that is, to restore innate information of cells, the broken DNA is repaired using information of a complementary base sequence which is not modified or information of a sister chromatid. The most common type of HDR is homologous recombination (HR). HDR is a repair or restoration method usually occurring in the S or G2/M phase of actively dividing cells.

To repair or restore damaged DNA using HDR, rather than using a complementary base sequence or sister chromatin of the cells, a DNA template artificially synthesized using information of a complementary base sequence or homologous base sequence, that is, a nucleic acid template including a complementary base sequence or homologous base sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the target gene or nucleic acid modified by a mutation to a normal gene or nucleic acid, or a gene or nucleic acid to be expressed in cells, but the present invention is not limited thereto.

In one example, a double or single strand of a target gene or nucleic acid may be cleaved using the CRISPR complex, a nucleic acid template including a base sequence complementary to a base sequence adjacent to the cleavage site may be provided to cells, and the cleaved base sequence of the target gene or nucleic acid may be repaired or restored through HDR.

Here, the nucleic acid template including the complementary base sequence may have broken DNA, that is, a cleaved double or single strand of a complementary base sequence, and further include a nucleic acid sequence or nucleic acid fragment to be inserted into the broken DNA. An additional nucleic acid sequence or nucleic acid fragment may be inserted into a cleaved site of the broken DNA, that is, the target gene or nucleic acid using the nucleic acid template including a nucleic acid sequence or nucleic acid fragment to be inserted into the complementary base sequence. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The complementary base sequence may be a base sequence having complementary bonds with broken DNA, that is, right and left base sequences of the cleaved double or single strand of the target gene or nucleic acid. Alternatively, the complementary base sequence may be a base sequence having complementary bonds with broken DNA, that is, 3' and 5' ends of the cleaved double or single strand of the target gene or nucleic acid. The complementary base sequence may be a 15 to 3000-base sequence, a length or size of the complementary base sequence may be suitably designed according to a size of the nucleic acid template or the target gene. Here, as the nucleic acid template, a double- or single-stranded nucleic acid may be used, or it may be linear or circular, but the present invention is not limited thereto.

In another example, a double- or single-stranded target gene or nucleic acid is cleaved using the CRISPR complex, a nucleic acid template including a homologous base sequence with a base sequence adjacent to a cleavage site is provided to cells, and the cleaved base sequence of the target gene or nucleic acid may be repaired or restored by HDR.

Here, the nucleic acid template including the homologous base sequence may be broken DNA, that is, a cleaved double- or single-stranded homologous base sequence, and further include a nucleic acid sequence or nucleic acid fragment to be inserted into the broken DNA. An additional nucleic acid sequence or nucleic acid fragment may be inserted into broken DNA, that is, a cleaved site of a target gene or nucleic acid using the nucleic acid template including a homologous base sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The homologous base sequence may be broken DNA, that is, a base sequence having homology with cleaved double-stranded base sequence or right and left single-stranded base sequences of a target gene or nucleic acid. Alternatively, the complementary base sequence may be a base sequence having homology with broken DNA, that is, the 3' and 5' ends of a cleaved double or single strand of a target gene or nucleic acid. The homologous base sequence may be a 15 to 3000-base sequence, and a length or size of the homologous base sequence may be suitably designed according to a size of the nucleic acid template or a target gene or nucleic acid. Here, as the nucleic acid template, a double- or single-stranded nucleic acid may be used and may be linear or circular, but the present invention is not limited thereto.

Other than the NHEJ and HDR, there are methods of repairing or restoring broken DNA.

Single-Strand Annealing (SSA)

SSA is a method of repairing double strand breaks between two repeat sequences present in a target nucleic acid, and generally uses a repeat sequence of more than 30 bases. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

SSA, similar to HDR, utilizes a complementary sequence, that is, a complementary repeat sequence, and in contrast, does not requires a nucleic acid template for modifying or correcting a target nucleic acid sequence.

Single-Strand Break Repair (SSBA)

Single strand breaks in a genome are repaired through a separate mechanism, SSBR, from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single base. After DNA gap filling, a DNA ligase promotes end joining.

Mismatch Repair (MMR)

MMR works on mismatched DNA bases. Each of an MSH2/6 or MSH2/3 complex has ATPase activity and thus plays an important role in recognizing a mismatch and initiating a repair, and the MSH2/6 primarily recognizes base-base mismatches and identifies one or two base mismatches, but the MSH2/3 primarily recognizes a larger mismatch.

Base Excision Repair (BER)

BER is a repair method which is active throughout the entire cell cycle, and used to remove a small non-helix-distorting base damaged region from the genome. In the damaged DNA, damaged bases are removed by cleaving an N-glycoside bond joining a base to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary base, and then an end of the newly-filled complementary base is ligated with the backbone by a DNA ligase, resulting in repair of the damaged DNA.

Nucleotide Excision Repair (NER)

NER is an excision mechanism important for removing large helix-distorting damage from DNA, and when the damage is recognized, a short single-strand DNA segment containing the damaged region is removed, resulting in a single strand gap of 22 to 30 bases. The generated gap is filled with a new complementary base, and an end of the newly filled complementary base is ligated with the backbone by a DNA ligase, resulting in the repair of the damaged DNA.

Gene Manipulation Effects

Manipulation or correction of a target gene or nucleic acid may largely lead to effects of knockout, knockdown, and knockin.

Knockout

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or nucleic acid is edited or corrected using a gRNA-CRISPR enzyme complex, that is, a CRISPR complex, the target gene or nucleic acid may be cleaved using the CRISPR complex. The damaged target gene or nucleic acid may be repaired through NHEJ using the CRISPR complex. The damaged target gene or nucleic acid may have indels due to NHEJ, and thereby, specific knockout for the target gene or nucleic acid may be induced.

Knockdown

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when a target gene or nucleic acid is edited or corrected using a gRNA-CRISPR inactive enzyme-transcription inhibitory activity domain complex, that is, a CRISPR inactive complex including a transcription inhibitory activity domain, the CRISPR inactive complex may specifically bind to the target gene or nucleic acid, transcription of the target gene or nucleic acid may be inhibited by the transcription inhibitory activity domain included in the CRISPR inactive complex, thereby inducing knockdown in which expression of the corresponding gene or nucleic acid is inhibited.

Knockin

The term "knockin" refers to insertion of a specific nucleic acid or gene into a target gene or nucleic acid, and here, the "specific nucleic acid" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited or corrected using a gRNA-CRISPR enzyme complex, that is, a CRISPR complex, the target gene or nucleic acid may be cleaved using the CRISPR complex. The target gene or nucleic acid damaged using the CRISPR complex may be repaired through HDR. Here, a specific nucleic acid may be inserted into the damaged gene or nucleic acid using a donor.

The term "donor" refers to a nucleic acid sequence that helps HDR-based repair of the damaged gene or nucleic acid, and here, the donor may include a specific nucleic acid.

The donor may be a double- or single-stranded nucleic acid.

The donor may be present in a linear or circular shape.

The donor may include a nucleic acid sequence having homology with a target gene or nucleic acid.

For example, the donor may include a nucleic acid sequence having homology with each of base sequences at a location into which a specific nucleic acid is to be inserted, for example, upstream (left) and downstream (right) of a damaged nucleic acid. Here, the specific nucleic acid to be inserted may be located between a nucleic acid sequence having homology with a base sequence downstream of the damaged nucleic acid and a nucleic acid sequence having homology with a base sequence upstream of the damaged nucleic acid. Here, the homologous nucleic acid sequence may have at least 50%, 55%, 60%, 65%, 70%, 75%, 80%, 85%, 90% or 95% or more homology or complete homology.

The donor may optionally include an additional nucleic acid sequence. Here, the additional nucleic acid sequence may serve to increase donor stability, knockin efficiency or HDR efficiency.

For example, the additional nucleic acid sequence may be an A, T-rich nucleic acid sequence, that is, an A-T rich domain. In addition, the additional nucleic acid sequence may be a scaffold/matrix attachment region (SMAR).

In one exemplary embodiment relating to a gene manipulation effect of the present invention, a manipulated target gene obtained using a gRNA-CRISPR enzyme complex, that is, a manipulated SC function-controlling factor, preferably, a manipulated PMP22 may have the following constitution.

In one exemplary embodiment, when the PMP22 is a gene,
the constitution of the artificially manipulated PMP22 by the gRNA-CRISPR enzyme complex may include modification of one or more nucleic acids among a deletion or insertion of one or more nucleotides;
a substitution with one or more nucleotides different from a wild-type gene; and
an insertion of one or more foreign nucleotides
in a continuous 1 bp to 50 bp, 1 bp to 40 bp or 1 bp to 30 bp, preferably, 3 bp to 25 bp region in the base sequence, which is located in a PAM sequence in a nucleic acid sequence constituting the PMP22 gene or adjacent to a 5' end and/or 3' end thereof.

In addition, a chemical modification of one or more nucleotides may be included in the nucleic acid sequence constituting the PMP22 gene.

Here, the "foreign nucleotide" is the concept including all exogeneous, for example, heterologous or artificially-synthesized nucleotides, other than nucleotides innately included in the PMP22 gene. The foreign nucleotide also includes a nucleotide with a size of several hundred, thousand or tens of thousands of bp to express a protein having a specific function, as well as a small oligonucleotide with a size of 50 bp or less. Such a foreign nucleotide may be a donor.

The chemical modification may include methylation, acetylation, phosphorylation, ubiquitination, ADP-ribosylation, myristylation, and glycosylation, for example, substitution of some functional groups contained in a nucleotide with any one of a hydrogen atom, a fluorine atom, an —O-alkyl group, an —O-acyl group, and an amino group, but the present invention is not limited thereto. In addition, to increase transferability of a nucleic acid molecule, the functional groups may also be substituted with any one of —Br, —Cl, —R, —R'OR, —SH, —SR, —N3 and —CN (R=alkyl, aryl, alkylene). In addition, the phosphate backbone of at least one nucleotide may be substituted with any one of an alkylphosphonate form, a phosphoroamidate form and a boranophosphate form. In addition, the chemical modification may be a substitution of at least one type of nucleotide contained in the nucleic acid molecule with any one of a locked nucleic acid (LNA), an unlocked nucleic acid (UNA), a morpholino, and a peptide nucleic acid (PNA), and the chemical modification may be bonding of the nucleic acid molecule with one or more selected from the group consisting of a lipid, a cell-penetrating peptide and a cell-target ligand.

To form a desired SC function-controlling system (including an SC function-controlling modification system), artificial modification using a gRNA-CRISPR enzyme complex may be applied to the nucleic acid constituting the SC function-controlling factor, that is, the PMP22 gene.

A region including the nucleic acid modification of the PMP22 gene may be a target region or target sequence.

Such a target sequence may be a target for the gRNA-CRISPR enzyme complex, and the target sequence may include or not include a PAM sequence recognized by the CRISPR enzyme. Such a target sequence may provide a critical standard in a gRNA designing stage to those of ordinary skill in the art.

Such nucleic acid modification includes the "cleavage" of a nucleic acid.

The term "cleavage" in a target region refers to breakage of a covalent backbone of polynucleotides. The cleavage includes enzymatic or chemical hydrolysis of a phosphodiester bond, but the present invention is not limited thereto, and also includes various other methods. The cleavage is able to be performed on both of a single strand and a double strand, and the cleavage of a double strand may result from distinct single-strand cleavage. The double-strand cleavage may generate blunt ends or staggered ends.

When an inactivated CRISPR enzyme is used, it may induce a factor possessing a specific function to approach a certain region of the target region or the PMP22 gene without the cleavage process. Chemical modification of one or more nucleotides in the nucleic acid sequence of the PMP22 gene may be included according to such a specific function.

In one example, various indels may occur due to target and non-target activities through the nucleic acid cleavage formed by the gRNA-CRISPR enzyme complex.

The term "indel" is the generic term for an insertion or deletion mutation occurring in-between some bases in a DNA base sequence. The indel may be introduced into a target sequence during repair by an HDR or NHEJ mechanism when the gRNA-CRISPR enzyme complex cleaves the nucleic acid (DNA or RNA) of the neovascularization-associated factor as described above.

The artificially manipulated PMP22 gene of the present invention refers to modification of the nucleic acid sequence of a native gene by cleavage, indels, or insertion using a donor of such a nucleic acid, and contributes to a desired SC function-controlling system (including an SC function-controlling factor modification system), for example, exhibition of an effect of controlling the functions of Schwann cells through expression and/or function modification of PMP22.

For example, the expression and activity of a specific protein may be inhibited by the artificially manipulated PMP22 gene.

The specific protein may be inactivated by the artificially manipulated PMP22 gene.

As an example, a specific target site of the PMP22 gene in the genome may be cleaved to knockdown or knockout the gene.

As another example, the targeted knockdown may be mediated by using an enzymatically inactivated CRISPR enzyme fused to a transcription repressor domain or chromatin modification protein in order to change the transcription, for example, block, reduce or decrease the transcription of the PMP22 gene.

The growth of Schwann cells may be suppressed or inhibited, or may be promoted or increased by the artificially manipulated SC function-controlling factor, that is, the artificially manipulated PMP22 gene.

The progression of the cell cycle of Schwann cells may be interrupted or arrested, or may be promoted by the artificially manipulated SC function-controlling factor, that is, the artificially manipulated PMP22 gene.

The differentiation of Schwann cells may be promoted or suppressed by the artificially manipulated SC function-controlling factor, that is, the artificially manipulated PMP22 gene.

The death of Schwann cells may be promoted or suppressed by the artificially manipulated SC function-controlling factor, that is, the artificially manipulated PMP22 gene.

The survival of peripheral nerve cells may be helped or interfered with by the artificially manipulated SC function-controlling factor, that is, the artificially manipulated PMP22 gene.

The maintenance and signaling of peripheral nerve cells may be helped or interfered with by the artificially manipulated SC function-controlling factor, that is, the artificially manipulated PMP22 gene.

The myelin sheath formation of nerve cell axons may be controlled by the artificially manipulated SC function-controlling factor, that is, the artificially manipulated PMP22 gene.

In this case, the myelin sheath formation includes the overall process of the myelin sheath formation such as production of the myelin sheath, degeneration of the myelin sheath, regeneration of the myelin sheath, maintenance of the myelin sheath, and compact myelin of the myelin sheath and all mechanisms associated with myelin sheath degeneration or the function of the myelin sheath.

The alleviation and treatment of dysfunctional or defective Schwann cells Schwann cells may be used by the artificially manipulated SC function-controlling factor, that is, the artificially manipulated PMP22 gene.

Further, it is possible to control all mechanisms that suppress or inhibit the growth of fibroblasts or glial cells, or promote or increase the growth of fibroblasts or glial cells by the artificially manipulated SC function-controlling factor, that is, the artificially manipulated PMP22 gene.

It is possible to control all mechanisms that are involved in the activity of fibroblasts or glial cells by the artificially manipulated SC function-controlling factor, that is, the artificially manipulated PMP22 gene.

In one exemplary embodiment of the present invention, the artificially manipulated SC function-controlling factor, that is, the artificially manipulated PMP22 gene may provide various artificially manipulated PMP22 gene according to the constitutional characteristic of the gRNA-CRISPR enzyme complex (e.g., included in a target region of the PMP22 gene or different in the adjacent major PAM sequence).

Hereinafter, while representative examples of CRISPR enzymes have been illustrated, they are merely specific examples, and thus the present invention is not limited thereto.

For example, when the CRISPR enzyme is a SpCas9 protein, the PAM sequence is 5'-NGG-3' (N is A, T, G, or C), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NGG-3' sequence in a target gene.

The present application may provide an artificially manipulated PMP22 gene, which is prepared by
a) deletion of one or more nucleotides of a continuous 1 bp to 25 bp, for example, 17 bp to 23 bp, region in the base sequence adjacent to the 5' end and/or 3' end of the 5'-NGG-3' (N is A, T, C or G) sequence,
b) substitution of one or more nucleotides of a continuous 1 bp to 25 bp, for example, 17 bp to 23 bp, region in the base sequence adjacent to the 5' end and/or 3' end of the 5'-NGG-3' sequence with nucleotides different from those of the wild-type gene,
c) insertion of one or more nucleotides into a continuous 1 bp to 25 bp, for example, 17 bp to 23 bp, region in the base sequence adjacent to the 5' end and/or 3' end of the 5'-NGG-3' sequence, or
d) a combination of two or more selected from a) through c)
in the nucleic acid sequence of the PMP22 gene.

For example, when the CRISPR enzyme is a CjCas9 protein, the PAM sequence is 5'-NNNNRYAC-3' (SEQ ID NO: 194) (each N is independently A, T, C or G, R is A or G, and Y is C or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNRYAC-3' sequence (SEQ ID NO: 194) in a target gene.

The present invention may provide an artificially manipulated PMP22 gene, which is prepared by
a') deletion of one or more nucleotides of a continuous 1 bp to 25 bp, for example, 17 bp to 23 bp, region in the base sequence adjacent to the 5' end and/or 3' end of the 5'-NNNNRYAC-3' (SEQ ID NO: 194) (each N is independently A, T, C or G, R is A or G, and Y is C or T),
b') substitution of one or more nucleotides of a continuous 1 bp to 25 bp, for example, 17 bp to 23 bp, region in the base sequence adjacent to the 5' end and/or 3' end of the 5'-NNNNRYAC-3' sequence (SEQ ID NO: 194) with nucleotides different from those of the wild-type gene,
c') insertion of one or more nucleotides into a continuous 1 bp to 25 bp, for example, 17 bp to 23 bp, region in the base sequence adjacent to the 5' end and/or 3' end of the 5'-NNNNRYAC-3' sequence (SEQ ID NO: 194), or d') a combination of two or more selected from a') through c') in the nucleic acid sequence of the PMP22 gene.

For example, when the CRISPR enzyme is an StCas9 protein, the PAM sequence is 5'-NNAGAAW-3' (SEQ ID NO: 192) (each N is independently A, T, C or G, and W is A or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNAGAAW-3' sequence (SEQ ID NO: 192) in a target gene.

The present invention may provide an artificially manipulated PMP22 gene, which is prepared by
- a'') deletion of one or more nucleotides of a continuous 1 bp to 25 bp, for example, 17 bp to 23 bp, region in the base sequence adjacent to the 5' end and/or the 3' end of the 5'-NNAGAAW-3' sequence (SEQ ID NO: 192) (each N is independently A, T, C or G, and W is A or T),
- b'') substitution of one or more nucleotides of a continuous 1 bp to 25 bp, for example, 17 bp to 23 bp, region in the base sequence adjacent to the 5' end and/or 3' end of the 5'-NNAGAAW-3' sequence (SEQ ID NO: 192) with nucleotides different from those of the wild-type gene,
- c'') insertion of one or more nucleotides into a continuous 1 bp to 25 bp, for example, 17 bp to 23 bp, region in the base sequence adjacent to the 5'-NNAGAAW-3' sequence (SEQ ID NO: 192), or
- d') a combination of two or more selected from a'') through c'') in the nucleic acid sequence of the PMP22 gene.

For example, when the CRISPR enzyme is a NmCas9 protein, the PAM sequence is 5'-NNNNGATT-3' (SEQ ID NO: 193) (each N is independently A, T, C or G), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNGATT-3' sequence (SEQ ID NO: 193) in a target gene.

The present invention may provide an artificially manipulated PMP22 gene, which is prepared by
- a''') deletion of one or more nucleotides of a continuous 1 bp to 25 bp, for example, 17 bp to 23 bp, region in the base sequence adjacent to the 5' end and/or 3' end of the 5'-NNNNGATT-3' (SEQ ID NO: 193) (each N is independently A, T, C or G),
- b''') substitution of one or more nucleotides of a continuous 1 bp to 25 bp, for example, 17 bp to 23 bp, region in the base sequence adjacent to the 5' end and/or 3' end of the 5'-NNNNGATT-3' sequence with nucleotides different from those of the wild-type gene,
- c''') insertion of one or more nucleotides into a continuous 1 bp to 25 bp, for example, 17 bp to 23 bp, region in the base sequence adjacent to the 5' end and/or 3' end of the 5'-NNNNGATT-3' sequence (SEQ ID NO: 193), or
- d''') a combination of two or more selected from a''') through c''') in the nucleic acid sequence of the PMP22 gene.

For example, when the CRISPR enzyme is an SaCas9 protein, the PAM sequence is 5'-NNGRR (T)-3' (SEQ ID NO: 199) (each N is independently A, T, C or G, R is A or G, and (T) is a randomly addable sequence), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNGRR (T)-3' sequence (SEQ ID NO: 199) in a target gene.

The present invention may provide an artificially manipulated PMP22 gene, which is prepared by
- a'''') deletion of one or more nucleotides of a continuous 1 bp to 25 bp, for example, 17 bp to 23 bp region, in the base sequence adjacent to the 5' end and/or the 3' end of the 5'-NNGRR (T)-3' sequence (SEQ ID NO: 199) (each N is independently A, T, C or G, R is A or G, and (T) is a randomly addable sequence),
- b'''') substitution of one or more nucleotides of a continuous 1 bp to 25 bp, for example, 17 bp to 23 bp, region in the base sequence adjacent to the 5' end and/or 3' end of the 5'-NNGRR (T)-3' sequence (SEQ ID NO: 199) with nucleotides different from those of the wild-type gene,
- c'''') insertion of one or more nucleotides into a continuous 1 bp to 25 bp, for example, 17 bp to 23 bp, region in the base sequence adjacent to the 5'-NNGRR (T)-3' (SEQ ID NO: 199) sequence, or
- d'''') a combination of two or more selected from a'''') through c'''') in the nucleic acid sequence of the PMP22 gene.

For example, when the CRISPR enzyme is a Cpf1 protein, the PAM sequence is 5'-TTN-3' (N is A, T, C or G), and the cleaved base sequence region (target region) may be a continuous 10 bp to 30 bp, for example, 15 bp to 26 bp, 17 bp to 30 bp or 17 bp to 26 bp, region in the base sequence adjacent to the 5' end or the 3' end of the 5'-TTN-3' sequence.

The Cpf1 protein may be derived from a microorganism such as Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), Candidatus Methanoplasma *termitum*, or *Eubacterium eligens*, for example, Parcubacteria bacterium (GWC2011_GWC2_44_17), Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Leptospira inadai*, Lachnospiraceae bacterium (MA2020), *Francisella novicida* (U112), Candidatus Methanoplasma *termitum*, or *Eubacterium eligens*, but the present invention is not limited thereto.

The present invention may provide an artificially manipulated PMP22 gene, which is prepared by
- a''''') deletion of one or more nucleotides of a continuous 10 bp to 30 bp, for example, 15 bp to 26 bp, region in the base sequence adjacent to the 5' end and/or the 3' end of the 5'-TTN-3' sequence (N is A, T, C or G),
- b''''') substitution of one or more nucleotides of a continuous 10 bp to 30 bp, for example, 15 bp to 26 bp, region in the base sequence adjacent to the 5' end and/or 3' end of the 5'-TTN-3' sequence with nucleotides different from those of the wild-type gene,
- c''''') insertion of one or more nucleotides of a continuous 10 bp to 30 bp, for example, 15 bp to 26 bp, region in the base sequence adjacent to the 5' end and/or 3' end of the 5'-TTN-3' sequence, or d''''') a combination of two or more selected from a''''') through c''''') in the nucleic acid sequence of the PMP22 gene.

In another exemplary embodiment, when the PMP22 is a protein, the artificially manipulated protein includes all proteins involved in formation of new or modified blood vessels by a direct or indirect action of the gRNA-CRISPR enzyme complex.

For example, the artificially manipulated protein may be a protein expressed by a PMP22 gene artificially manipulated by the gRNA-CRISPR enzyme complex or another protein increased or reduced by an influence by such protein activity, but the present invention is not limited thereto.

The artificially manipulated PMP22 protein may have an amino acid composition and activity corresponding to the composition of the artificially manipulated PMP22 gene.

As an embodiment, an (i) artificially manipulated protein which is changed in expression characteristics may be provided.

For example, protein modification may have one or more characteristics:
- a decrease or increase in expression level according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the PMP22 gene or adjacent to the 5' end and/or the 3' end thereof;
- a decrease or increase in expression level according to the substitution with one or more nucleotides different from those of a wild-type gene;
- a decrease or increase in expression level, expression of a fusion protein or independent expression of a specific protein according to the insertion of one or more foreign nucleotides; and
- a decrease or increase in expression level of a third protein influenced by expression characteristics of the above-described proteins.

An (ii) artificially manipulated protein which is changed in structural characteristics may be provided.

For example, protein modification may have one or more characteristics:
- a change in codons, amino acids and three-dimensional structure according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the PMP22 gene or adjacent to the 5' end and/or the 3' end thereof;
- a change in codons, amino acids, and three-dimensional structure thereby according to the substitution with one or more nucleotides different from a wild-type gene;
- a change in codons, amino acids, and three-dimensional structure, or a fusion structure with a specific protein or independent structure from which a specific protein is separated according to the insertion of one or more foreign nucleotides; and
- a change in codons, amino acids, and three-dimensional structure of a third protein influenced by the above-described protein changed in structural characteristic.

An (iii) artificially manipulated protein changed in functional characteristics may be provided.

For example, protein modification may have one or more characteristics:
- the activation or inactivation of a specific function or introduction of a new function by protein modification caused by a deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the PMP22 gene or adjacent to the 5' end and/or the 3' end thereof;
- the activation or inactivation of a specific function or introduction of a new function by protein modification caused by substitution with one or more nucleotides different from those of a wild-type gene;
- the activation or inactivation of a specific function or introduction of a new function by protein modification caused by insertion of one or more foreign nucleotides, particularly, introduction of a third function to an existing function due to fusion or independent expression of a specific protein; and
- the change in the function of a third protein influenced by the above-described protein changed in functional characteristics.

In addition, a protein artificially manipulated by the chemical modification of one or more nucleotides in the nucleic acid sequence constituting the PMP22 gene may be included.

For example, one or more of the expression, structural and functional characteristics of a protein caused by methylation, acetylation, phosphorylation, ubiquitination, ADP-ribosylation, myristylation and glycosylation may be changed.

For example, the third structure and function may be achieved by binding of a third protein into the nucleic acid sequence of the gene due to the chemical modification of nucleotides.

5. Other Additional Components

An additional component may be selectively added to increase the efficiency of a guide nucleic acid-editor protein complex or improve the repair efficiency of a damaged gene or nucleic acid.

The additional component may be selectively used to improve the efficiency of the guide nucleic acid-editor protein complex.

Activator

The additional component may be used as an activator to increase the cleavage efficiency of a target nucleic acid, gene or chromosome of the guide nucleic acid-editor protein complex.

The term "activator" refers to a nucleic acid serving to stabilize the bonding between the guide nucleic acid-editor protein complex and the target nucleic acid, gene or chromosome, or to allow the guide nucleic acid-editor protein complex to more easily approach the target nucleic acid, gene or chromosome.

The activator may be a double-stranded nucleic acid or single-stranded nucleic acid.

The activator may be linear or circular.

The activator may be divided into a "helper" that stabilizes the bonding between the guide nucleic acid-editor protein complex and the target nucleic acid, gene or chromosome, and an "escorter" that serves to allow the guide nucleic acid-editor protein complex to more easily approach the target nucleic acid, gene or chromosome.

The helper may increase the cleavage efficiency of the guide nucleic acid-editor protein complex with respect to the target nucleic acid, gene or chromosome.

For example, the helper includes a nucleic acid sequence having homology with the target nucleic acid, gene or chromosome. Therefore, when the guide nucleic acid-editor protein complex is bonded to the target nucleic acid, gene or chromosome, the homologous nucleic acid sequence included in the helper may form an additional complementary bond with the target nucleic acid, gene or chromosome to stabilize the bonding between the guide nucleic acid-editor protein complex and the target nucleic acid, gene or chromosome.

The escorter may increase the cleavage efficiency of the guide nucleic acid-editor protein complex with respect to the target nucleic acid, gene or chromosome.

For example, the escorter includes a nucleic acid sequence having homology with the target nucleic acid, gene or chromosome. Here, the homologous nucleic acid sequence included in the escorter may partly form a complementary bond with a guide nucleic acid of the guide nucleic acid-editor protein complex. Therefore, the escorter partly forming a complementary bond with the guide nucleic acid-editor protein complex may partly form a complementary bond with the target nucleic acid, gene or chromosome, and as a result, may allow the guide nucleic acid-editor protein complex to accurately approach the position of the target nucleic acid, gene or chromosome.

The homologous nucleic acid sequence may have at least 50%, 55%, 60%, 65%, 70%, 75%, 80%, 85%, 90% or 95% or more homology, or complete homology.

In addition, the additional component may be selectively used to improve the repair efficiency of the damaged gene or nucleic acid.

Assistor

The additional component may be used as an assistor to improve the repair efficiency of the damaged gene or nucleic acid.

The term "assistor" refers to a nucleic acid that serves to participate in a repair process or increase the repair efficiency of the damaged gene or nucleic acid, for example, the gene or nucleic acid cleaved by the guide nucleic acid-editor protein complex.

The assistor may be a double-stranded nucleic acid or single-stranded nucleic acid.

The assistor may be present in a linear or circular shape.

The assistor may be divided into an "NHEJ assistor" that participates in a repair process using NHEJ or improves repair efficiency and an "HDR assistor" that participates in a repair process using HDR or improves repair efficiency according to a repair method.

The NHEJ assistor may participate in a repair process or improve the repair efficiency of the damaged gene or nucleic acid using NHEJ.

For example, the NHEJ assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and include a nucleic acid sequence having homology with the nucleic acid sequence at the other end (e.g., the 5' end) of the damaged nucleic acid sequence. In addition, a nucleic acid sequence having homology with each of the base sequences upstream and downstream of the damaged nucleic acid sequence may be included. The nucleic acid sequence having such homology may assist two parts of the damaged nucleic acid sequence to be placed in close proximity, thereby increasing the repair efficiency of the damaged nucleic acid by NHEJ.

The HDR assistor may participate in the repair process or improve repair efficiency of the damaged gene or nucleic acid using HDR.

For example, the HDR assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and a nucleic acid sequence having homology with the nucleic acid sequence at the other end (e.g., the 5' end) of the damaged nucleic acid sequence. Alternatively, a nucleic acid sequence having homology with each of the base sequences upstream and downstream of the damaged nucleic acid sequence may be included. The nucleic acid sequence having such homology may serve as a template of the damaged nucleic acid sequence to increase the repair efficiency of the damaged nucleic acid by HDR.

In another example, the HDR assistor may include a nucleic acid sequence having homology with a part of the damaged nucleic acid sequence and a specific nucleic acid, for example, a nucleic acid or gene to be inserted. Here, the homologous nucleic acid sequence may include a nucleic acid sequence having homology with each of the base sequences upstream and downstream of the damaged nucleic acid sequence. The specific nucleic acid may be located between a nucleic acid sequence having homology with a base sequence downstream of the damaged nucleic acid and a nucleic acid sequence having homology with a base sequence upstream of the damaged nucleic acid. The nucleic acid sequence having such homology and specific nucleic acid may serve as a donor to insert a specific nucleic acid into the damaged nucleic acid, thereby increasing HDR efficiency for knockin.

The homologous nucleic acid sequence may have at least 50%, 55%, 60%, 65%, 70%, 75%, 80%, 85%, 90% or 95% or more homology or complete homology.

6. Subject

The term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells or human cells, but the present invention is not limited thereto.

The tissue may be animal or human body tissue such as skin, liver, kidney, heart, lung, brain or muscle tissue.

The subject may be a specimen or sample including a target nucleic acid, gene, chromosome or protein of the guide nucleic acid-editor protein complex.

The specimen or sample may be obtained from an organism including a target nucleic acid, gene, chromosome or protein and may be saliva, blood, skin tissue, Schwann cells, cancer cells or stem cells.

In the present invention, as a specific example, the subject may include a target gene or nucleic acid of the guide nucleic acid-editor protein complex.

Here, the target gene may be a SC function-controlling factor.

The SC function-controlling factor may be a PMP22 gene.

The target gene may be a wild type, or a modified form in the wild-type.

In one exemplary embodiment of the present invention, the subject may include a gene or nucleic acid manipulated by the guide nucleic acid-editor protein complex.

Here, the manipulated gene may be a SC function-controlling factor.

The SC function-controlling factor may be a PMP22 gene.

Here, the guide nucleic acid may target a PMP22 gene.

The guide nucleic acid may be a nucleic acid sequence complementary to a target sequence of the PMP22 gene.

The guide nucleic acid may target one or more genes.

The guide nucleic acid may simultaneously target two or more genes. Here, the two or more genes may be homologous or heterologous genes.

The guide nucleic acid may target one or more target sequences.

The guide nucleic acid may be designed in various forms according to the number or locations of the target sequences.

In one exemplary embodiment of the present invention, the guide nucleic acid may be a nucleic acid sequence complementary to one or more target sequences of the sequences listed in Table 1, Table 2, Table 3, Table 4, Table 5, Table 6 and Table 7.

In a certain embodiment, for artificial manipulation of the PMP22 gene, a guide nucleic acid sequence corresponding to any one of the target sequences of SEQ ID NOs: 1 to 66.

In a certain embodiment, for artificial manipulation of the PMP22, an editor protein that interacts with a guide nucleic acid sequence corresponding to, for example, forming a complex with any one of the target sequences of SEQ ID NOs: 1 to 66, for example, SEQ ID NOs: 1 to 8, 14 to 29 or 41 to 53 is provided.

In a certain embodiment, a nucleic acid modification product of each gene in which artificial manipulation occurs at a target sequence region of any one of SEQ ID NOs: 1 to 66, for example, SEQ ID NOs: 1 to 79, 14 to 29 or 41 to 53 and an expression product thereof are provided.

7. Delivery

The guide nucleic acid, editor protein or guide nucleic acid-editor protein complex may be delivered or introduced into a subject by various delivering methods and various forms.

The guide nucleic acid may be delivered or introduced into a subject in the form of DNA, RNA or a mixed form.

The editor protein may be delivered or introduced into a subject in the form of DNA, RNA, a DNA/RNA mixture, a peptide, a polypeptide, which encodes the editor protein, or a protein.

The guide nucleic acid-editor protein complex may be delivered or introduced into a target in the form of DNA, RNA or a mixture thereof, which encodes each component, that is, a guide nucleic acid or an editor protein.

The guide nucleic acid-editor protein complex may be delivered or introduced into a subject as a complex of a guide nucleic acid having a form of DNA, RNA or a mixture thereof and an editor protein having a form of a peptide, polypeptide or protein.

In addition, an additional component capable of increasing or inhibiting the efficiency of the guide nucleic acid-editor protein complex may be delivered or introduced into a subject by various delivering methods and in various forms.

The additional component may be delivered or introduced into a subject in the form of DNA, RNA, a DNA/RNA mixture, a peptide, a polypeptide or a protein.

i) Delivery in Form of DNA, RNA or Mixture Thereof

The form of DNA, RNA or a mixture thereof, which encodes the guide nucleic acid and/or editor protein may be delivered or introduced into a subject by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

Vector-Based Introduction

The nucleic acid sequence encoding the guide nucleic acid and/or editor protein may be delivered or introduced into a subject by a vector.

The vector may include a nucleic acid sequence encoding a guide nucleic acid and/or editor protein.

For example, the vector may simultaneously include nucleic acid sequences, which encode the guide nucleic acid and the editor protein, respectively.

For example, the vector may include the nucleic acid sequence encoding the guide nucleic acid.

As an example, domains included in the guide nucleic acid may be contained all in one vector, or may be divided and then contained in different vectors.

For example, the vector may include the nucleic acid sequence encoding the editor protein.

In one example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

Non-Vector-Based Introduction

A nucleic acid sequence encoding a guide nucleic acid and/or editor protein may be delivered or introduced into a subject using a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, particle bombardment, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

As an example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nanovesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

Other additives may be included.

ii) Delivery in Form of Peptide, Polypeptide or Protein

An editor protein in the form of a peptide, polypeptide or protein may be delivered or introduced into a subject by a method known in the art The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

iii) Delivery in Form of Nucleic Acid-Protein Mixture

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

In the present invention, as an embodiment of a method for delivering the guide nucleic acid and/or editor protein into a subject, the delivery of gRNA, a CRISPR enzyme or a gRNA-CRISPR enzyme complex will be described below.

In an embodiment of the present invention, a nucleic acid sequence encoding the gRNA and/or CRISPR enzyme will be delivered or introduced into a subject using a vector.

The vector may include the nucleic acid sequence encoding the gRNA and/or CRISPR enzyme.

For example, the vector may simultaneously include the nucleic acid sequences encoding the gRNA and the CRISPR enzyme.

For example, the vector may include the nucleic acid sequence encoding the gRNA.

In one example, domains contained in the gRNA may be contained in one vector, or may be divided and then contained in different vectors.

For example, the vector may include the nucleic acid sequence encoding the CRISPR enzyme.

In one example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The gRNA and/or CRISPR enzyme may be introduced into a subject using a virus having such a characteristic. The gRNA and/or CRISPR enzyme introduced using the virus may be temporarily expressed in the subject (e.g., cells). Alternatively, the gRNA and/or CRISPR enzyme introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector only including gRNA or a CRISPR enzyme or a viral vector including both of gRNA and a CRISPR enzyme may be designed. Alternatively, a viral vector including gRNA, a CRISPR enzyme and additional components may be designed.

In one example, a nucleic acid sequence encoding gRNA and/or a CRISPR enzyme may be delivered or introduced by a recombinant lentivirus.

In another example, a nucleic acid sequence encoding gRNA and/or a CRISPR enzyme may be delivered or introduced by a recombinant adenovirus.

In still another example, a nucleic acid sequence encoding gRNA and/or a CRISPR enzyme may be delivered or introduced by recombinant AAV.

In yet another example, a nucleic acid sequence encoding gRNA and/or a CRISPR enzyme may be delivered or introduced by one or more hybrids of hybrid viruses, for example, the viruses described herein.

In one exemplary embodiment of the present invention, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

8. Transformant

The term "transformant" refers to an organism into which a guide nucleic acid, editor protein or guide nucleic acid-editor protein complex is introduced, an organism in which a guide nucleic acid, editor protein or guide nucleic acid-editor protein complex is expressed, or a specimen or sample obtained from the organism.

The transformant may be an organism into which a guide nucleic acid, editor protein or guide nucleic acid-editor protein complex is introduced in the form of DNA, RNA or a mixture thereof.

For example, the transformant may be an organism into which a vector including a nucleic acid sequence encoding a guide nucleic acid and/or editor protein is introduced. Here, the vector may be a non-viral vector, viral vector or recombinant viral vector.

In another example, the transformant may be an organism into which a nucleic acid sequence encoding a guide nucleic acid and/or editor protein is introduced in a non-vector form. Here, the non-vector may be naked DNA, a DNA complex, mRNA or a mixture thereof.

The transformant may be an organism into which a guide nucleic acid, editor protein or guide nucleic acid-editor protein complex is introduced in the form of a peptide, polypeptide or protein.

The transformant may be an organism into which a guide nucleic acid, editor protein or guide nucleic acid-editor protein complex is introduced in the form of DNA, RNA, a peptide, a polypeptide, a protein or a mixture thereof.

For example, the transformant may be an organism into which a guide nucleic acid-editor protein complex including an RNA-type guide nucleic acid and a protein-type editor protein is introduced.

The transformant may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells, or human cells, but the present invention is not limited thereto.

The tissue may be an animal or human body tissue such as skin, liver, kidney, heart, lung, brain, or muscle tissue.

The transformant may be an organism into which a guide nucleic acid, editor protein or guide nucleic acid-editor protein complex is introduced or expressed, or a specimen or sample obtained from the organism.

The specimen or sample may be saliva, blood, skin tissue, Schwann cells, cancer cells or stem cells.

[Use]

An embodiment of the present invention is a use of treating a subject with a Schwann cell dysfunction associated disease using an SC function-controlling factor, preferably, a composition for artificially manipulating PMP22, or an artificially manipulated SC function-controlling factor, preferably, artificially manipulated PMP22.

The subject to be treated may be a mammal including a primate such as a human and a monkey, a rodent such as a rat and a mouse, and the like.

Diseases to be Treated

In embodiments, a disease to be treated may be an SC dysfunction associated disease.

The "SC dysfunction associated disease" refers to all states generated by abnormal functions of Schwann cells. The "SC dysfunction associated disease" includes a disease due to abnormal or defective Schwann cells, which may occur during the overall development and growth process ranging from the growth and differentiation of Schwann cells to the death of Schwann cells, and also includes all diseases due to an abnormality or defect in a function, such as the survival and maintenance of peripheral nerve cells of Schwann cells and the myelin sheath formation (myelination) in the axons.

Further, the SC dysfunction associated disease also includes all states generated by abnormal functions of fibroblasts and/or glial cells. The SC dysfunction associated disease includes a disease due to abnormal or defective cells, which may occur during the overall development and growth process ranging from the growth and differentiation of fibroblasts and/or glial cells to the death of fibroblasts and/or glial cells.

Examples of the SC dysfunction associated disease include Charcot-Marie-Tooth disease (CMT), Guillain-Barre syndrome (GBS), acute inflammatory demyelinating polyradiculopathy type, schwannomatosis, and chronic inflammatory demyelinating polyneuropathy (CIDP), but are not limited thereto.

In an example, the SC dysfunction associated disease may be a demyelinating disease.

In this case, the demyelinating disease includes all diseases occurring due to the damage, defects, instability, degeneration, and remyelination of a myelin sheath.

In addition, the SC dysfunction associated disease includes an SC function-controlling factor associated disease.

The "SC function-controlling factor associated disease" refers to all states occurring due to the mutation of the SC function-controlling factor, the duplication of the SC function-controlling gene, the abnormal expression of the SC function-controlling factor, and the like.

Examples of the SC function-controlling factor associated disease include Charcot-Marie-Tooth disease (CMT), Dejerine-Sottas disease, Congenital Hypomyelination Neuropathy (CHN), Roussy-Levy syndrome (RLS), and Hereditary Neuropathy with liability to Pressure Palsies (HNPP), but are not limited thereto.

In an example, the SC function-controlling factor associated disease may be a PMP22 associated disease.

In this case, the PMP22 associated disease includes all diseases occurring due to the mutation of PMP22, the duplication of the PMP22 gene, the abnormal expression of PMP22, and the like.

In an embodiment, the SC function-controlling factor associated disease may be a disease occurring due to the duplication of the PMP22 gene.

Preferably, the SC function-controlling factor associated disease may be Charcot-Marie-Tooth disease type 1A (CMT1A), Dejerine-Sottas disease (DSS), Congenital Hypomyelination Neuropathy (CHN), or Roussy-Levy syndrome (RLS).

Charcot-Marie-Tooth Disease (CMT)

The CMT disease is a hereditary disease caused by gene duplication that occurs in human chromosomes, and genes involved in the development of peripheral nerves in the hands and feet are duplicated by mutations, thereby causing a deformation such as a shape like an inverted champagne bottle. The CMT disease is a relatively common neurological genetic disease that occurs in 36 out of 100,000 people in the United States, and the number of patients is 2.8 million worldwide and estimated to be around 17,000 even in Korea. The CMT disease is largely classified into a total of 5 types of CMT1, CMT2, CMT3, CMT4, and CMTX according to the inherited aspect, CMT1, CMT2 and CMT3 are dominant and inherited with a 50% probability in children, and CMT4 is recessive and inherited with a probability of 25%. CMT1 and CMT2 are dominantly inherited in most domestic patients (80% and 20 to 40%, respectively), and CMT3 and CMT4 are extremely rare. CMTX is inherited through the maternal line along X chromosomes, but the frequency thereof is 10 to 20%.

CMT1 is a disease caused by the inability to perform the normal process of gene expression due to gene duplication involved in the formation of proteins of the myelin sheath surrounding the neuronal axon. CMT1A is an autosomal dominant genetic disease, caused by duplication of the PMP22 gene located on chromosome No. 17 17p11.2-p12, resulting in the structural and functional abnormalities of the myelin sheath caused by the overexpression of PMP22, which is an important component of the myelin sheath.

CMT2 is associated with axonal abnormalities, and is a neuropathy with a considerably reduced action potential of motor sensory nerves while the nerve conduction velocity is close to the normal state, and CMT3 occurs in early childhood as an extremely rare autosomal recessive genetic disease and is a type in which clinical symptoms and a decrease in nerve conduction velocity are very severe. CMT4 is also a type in which the onset age is early and clinical symptoms are severe, is autosomal recessive inherited, and CMTX occurs while being associated with X chromosomes and the symptoms thereof in men are more severe than those in women.

Dejerine-Sottas Disease, (DSS)

DSS is a demyelinating motor sensory neuropathy occurring at an early age and is a disease which is usually autosomal dominantly inherited but is also autosomal recessively inherited, exhibits a severe demyelinating neuropathy, exhibits abnormalities of motor nerves from infancy, and is characterized by exhibiting very slow nerve conduction and an increase in specific proteins in cerebrospinal fluid. Dejerine-Sottas disease has a very rapid rate of progression, and is characterized in that gait disturbance starts from an early age and is also inherited, but also occurs sporadically. Similarly to CMT1A, PMP22 duplication is found among some patients with DSS, and in addition, it was confirmed that a missense mutation of the corresponding gene was present.

Congenital Hypomyelination Neuropathy (CHN)

CHN is a nervous system disease whose symptoms appear immediately after birth, and as the main symptoms thereof, respiratory failure, muscle weakness, muscle movement dissonance, a decrease in muscle tonicity, areflexia, motor incoordination (kinesioneurosis; ataxia), and paralysis or dysesthesia appear, and affect men and women at the same rate. CHN is a genetic disease, in which a disorder occurs in motor and sensory nerves, and is characterized by a reduction in myelin sheath formation while demyelination and remyelination of the myelin sheath are repeated.

Roussy-Levy Syndrome (RLS)

RLS is a rare type of hereditary motor sensory neuropathy and was first described by Roussy and Levy, et al., in 1926, and is a case where tremors of limbs, gait loss, and the like are more severe than other hereditary motor sensory neuropathies, but the same symptoms were later found in various hereditary motor sensory neuropathy subtypes, so that RLS is currently regarded as one symptom that appears in the hereditary motor sensory neuropathy. For RLS, a mutation of an MPZ gene as a myelin protein zero gene was found in a genetic test of patients who were first reported to have RLS, and in other patients, a case where there is a duplication of a PMP22 gene as a gene of myelin protein 22 of the peripheral nerves has been reported.

In other embodiments, the present invention may provide an additional system for controlling a third in vivo mechanism, concomitant with various functions of a specific factor (for example, an SC function-controlling factor) whose functions are artificially modified.

For example, the artificially modified specific factor may be a PMP22 gene.

The third mechanism may be an in vivo mechanism in which the gene is involved, other than the function of Schwann cells.

Pharmaceutical Composition

One exemplary embodiment of the present invention relates to a composition to be used in treatment of a disease using an artificially manipulated SC function-controlling factor.

The composition may include a manipulation composition capable of artificially manipulating the SC function-controlling factor. The composition may be referred to as a therapeutic composition or pharmaceutical composition.

In an exemplary embodiment, the composition may include a manipulation composition capable of artificially manipulating a SC function-controlling factor.

The manipulation composition may include a guide nucleic acid-editor protein complex.

The manipulation composition may include a guide nucleic acid and/or editor protein.

The manipulation composition may include a nucleic acid encoding the guide nucleic acid and/or editor protein.

The manipulation composition may include a virus comprising a nucleic acid encoding the guide nucleic acid and/or editor protein.

In another exemplary embodiment, the composition may further include an additional element.

The additional element may include a suitable carrier for delivery into the body of a subject.

In one exemplary embodiment, the following therapeutic compositions will be provided:
  a composition for treating an SC dysfunction disorder and/or SC function-controlling factor associated disease, which includes a guide nucleic acid capable of forming a complementary bond with each of one or more target sequences in nucleic acid sequences of a PMP22 gene, or a nucleic acid sequence encoding the same, and
  an editor protein or a nucleic acid sequence encoding the same;
  a composition for treating a SC dysfunction disorder and/or SC function-controlling factor associated disease, which includes a guide nucleic acid capable of forming a complementary bond with each of the target sequences of SEQ ID NOs: 1 to 66, for example, SEQ ID NOs: 1 to 8, 14 to 29 or 41 to 53 of nucleic acid sequences of a PMP22 gene, or a nucleic acid sequence encoding the same; and
  an editor protein or a nucleic acid sequence encoding the same.
  a composition for treating a SC dysfunction disorder and/or SC function-controlling factor associated disease, which includes a complex formed of a guide nucleic acid capable of forming a complementary bond with each of the target sequences of SEQ ID NOs: 1 to 66, for example, SEQ ID NOs: 1 to 8, 14 to 29 or 41 to 53 of nucleic acid sequences of a PMP22 gene or a nucleic acid sequence encoding the same; and an editor protein.

Here, the guide nucleic acid or nucleic acid sequence encoding the same; and a nucleic acid sequence encoding the editor protein may be present in the form of one or more vectors. The guide nucleic acid or nucleic acid sequence encoding the same; and a nucleic acid sequence encoding the editor protein may be present in the form of homologous or heterologous vectors.

Treatment Method

In another exemplary embodiment of the present invention, a method for treating a disease in a patient, which includes producing the above-described composition and administering an effective amount of the composition to a patient requiring the same, is provided.

Gene Manipulating Treatment

A treatment method for regulating SC function-controlling factor, preferably, expression of a PMP22 gene by manipulating a gene of a living organism may be used. Such a treatment method may be achieved by directly injecting a composition for manipulating a gene to manipulate the gene of a living organism into the organism.

The composition for gene manipulation may include a guide nucleic acid-editor protein complex.

The composition for gene manipulation may be injected into a specific location of the body.

Here, the specific location of the body may be a tissue in which expression and/or function of SC function-controlling factor, preferably PMP22, is abnormal; or a location close to the tissue. For example, the specific location of the body may be, for example, the peripheral nerve tissue.

Subjects for administration of the composition may be mammals including primates such as a human or a monkey, rodents such as a mouse or a rat, etc.

The composition may be administered by any convenient method such as injection, transfusion, implantation or transplantation. The composition may be administered subcutaneously, intradermally, intraocularly, intravitreally, intratumorally, intranodally, intramedullary, intramuscularly, intravenously, intralymphatically, or intraperitoneally.

A dose (pharmaceutically effective amount to obtain a predetermined, desired effect) of the composition may be selected from all integers in the value ranges of 104-109 cells, for example, 105 to 106 cells/kg (body weight), per kg of the subject of administration, but the present invention is not limited thereto. The composition may be suitably prescribed in consideration of the age, health condition and body weight of the subject of administration, the types of treatments simultaneously received, if they were, frequency of the co-treatments, and characteristics of a desired effect.

In one aspect, the present invention provides a method for modifying a target polynucleotide in prokaryotic cells, which may be achieved in vivo, ex vivo, or in vitro.

In some embodiments, the method may include sampling cells or a cell population from a human or non-human animal, and modifying the cell or cells. Culturing may occur at any step ex vivo. The cell or cells may also be reintroduced into a non-human animal or plant. The reintroduced cells are most preferably stem cells.

In still another exemplary embodiment, the present invention may provide a method for artificially manipulating cells, which includes: introducing (a) a guide nucleic acid capable of forming a complementary bond with the target sequences of SEQ ID NOs: 1 to 66, for example, SEQ ID NOs: 1 to 8, 14 to 29 or 41 to 53 of nucleic acid sequences of a PMP22 gene or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, or a nucleic acid sequence encoding the same to cells.

The guide nucleic acid and the editor protein may be present in one or more vectors in the form of a nucleic acid sequence, or in a complex of a combination of the guide nucleic acid and the editor protein.

The introduction step may be carried out in vivo or ex vivo.

A technique of the above-described "7. Delivery" section may be referenced before the introduction step.

For example, the introduction stage may be achieved by one or more methods selected from electroporation, liposomes, plasmids, viral vectors, nanoparticles, and a protein translocation domain (PTD) fusion protein method.

For example, the viral vector may be one or more selected from the group consisting of a retrovirus, a lentivirus, an adenovirus, adeno-associated virus (AAV), vaccinia virus, a poxvirus and a herpes simplex virus.

When an SC function-controlling factor, preferably, PMP22 is artificially manipulated by the method and composition of some embodiments of the present invention, it is possible to control the abnormal expression and/or function of PMP22, and by controlling the abnormal expression and/or function of PMP22, the expression and/or function of abnormal PMP22 are/is normally improved, so that it is possible to obtain effects of recovering from or improving abnormal functions of Schwann cells, and the like caused by the abnormal expression of PMP22.

Additional Uses

In a certain embodiment, the present invention may provide a kit for preparing a composition for treating SC dysfunction disorder and/or SC function-controlling factor associated disease.

The kit may be prepared by a conventional preparation method known in the art.

The kit may further include a detectable label. The term "detectable label" refers to an atom or molecule for specifically detecting a molecule containing a label among the same type of molecules without a label. The detectable label may be attached to an antibody specifically binding to a protein or a fragment thereof, an interaction protein, a ligand, nanoparticles, or an aptamer. The detectable label may include a radionuclide, a fluorophore, and an enzyme.

In a certain embodiment, the present invention may provide a method for screening a material capable of regulating the expression level of an artificially manipulated SC function-controlling factor, preferably, a PMP22 gene.

In a certain embodiment, the present invention may provide a method for providing information on the sequence of a target site which is able to be artificially manipulated in a subject by analyzing the sequences of SC function-controlling factor, preferably a PMP22 gene.

In addition, a method for constructing a library using the information provided by such a method.

Here, a known database may be used.

In specific embodiments, an animal or cells which can be used for research using the method of the present invention may be provided.

An animal or cells which includes chromosome editing in one or more nucleic acid sequences associated with a disease may be prepared using the above-described method. Such a nucleic acid sequence may be a reference sequence which may encode a disease-associated protein sequence or may be associated with a disease.

In one exemplary embodiment, an effect of mutation and occurrence and/or progression of a disease may be studied in an animal or cells using measurements conventionally used in disease research with the animal or cells prepared by the method of the present invention. Alternatively, a pharmaceutical effect of an active compound in a disease using such an animal or cells may be studied.

In another exemplary embodiment, the effect of the strategy of a possible gene therapy may be evaluated using the animal or cells prepared by the method of the present invention. That is, the development and/or progression of a corresponding disease may be suppressed or reduced by modifying a chromosome sequence encoding a disease-associated protein. Particularly, this method includes forming a modified protein by editing a chromosome sequence encoding a disease-associated protein, resulting in the achievement of a modified response of the animal or cells. Therefore, in some embodiments, a genetically-modified animal may be compared with an animal vulnerable to the development of a corresponding disease, thereby evaluating the effect of a gene therapy process.

The use may include a disease model, a pharmacological model, a developmental model, a cell functional model, and a humanized model. For example, the use may include an abnormal function associated disease model, a pharmacological model, a developmental model, a cell functional model, and a humanized model of Schwann cells by PMP22.

An artificially manipulated SC function-controlling factor and an SC function-controlling system (SC function-controlling modification system) thereby may be used to treat an effective SC dysfunction and/or SC function-controlling factor associated disease, for example, a PMP22 overexpression or PMP22 gene duplication associated disease. Further, through various in vivo mechanisms in which the SC function-controlling factor, preferably, PMP22, is involved, it is possible to improve an efficacy of an SC function-controlling system (including an SC function-controlling factor modification system).

Hereinafter, the present invention will be described in further detail with reference to examples.

The examples are merely provided to describe the present invention in further detail, and it might be obvious to those of ordinary skill in the art that the scope of the present invention is not limited to the following examples.

EXPERIMENTAL METHOD

1. Design of gRNA

CRISPR/Cas9 target sites of a human PMP22 gene were selected using CRISPR RGEN Tools (www.rgenome.net). The target sites of the PMP22 gene may vary depending on the type of CRISPR enzyme, target sequences of a coding site (coding sequence, CDS), a TATA-box site, and an enhancer site (for example, an EGR2-, SOX10- or TEAD1-binding site; or a distal enhancer site (distal enhancer region) B or C) of the PMP22 gene for SpCas9 are summarized in Tables 1, 3, 5, and 7 described above, and target sequences of a coding site (coding sequence, CDS), a TATA-box site, and an enhancer site (for example, an EGR2- or SOX10-binding site) of the PMP22 gene for CjCas9 are summarized in Tables 2, 4, and 6.

All gRNAs were produced in the form of chimeric single stranded RNA (sgRNA). Backbone sequences of Cj- and Sp-specific sgRNAs except for the target sequence are 5'-GUUUUAGUCCCUGAAAAGGGACUAAAAUA-AAGAGUUUGCGGGACUCUGCGGGGUUACA AUCCCCUAAAACCGCUUUU-3' (SEQ ID NO: 167) and 5'-GUUUUAGAGCUAGAAAUAGCAAGUUAAAA-UAAGGCUAGUCCGUUAUCAACUUGAAAAAG UGGCACCGAGUCGGUGC-3' (SEQ ID NO: 168), respectively.

2. Construction and Synthesis of gRNA sgRNA was packed into an AAV vector or synthesized with RNA. In order to insert the sgRNA into a viral vector, a DNA oligonucleotide corresponding to 20 to 22 base sequences of the sgRNA was designed and annealed, and ligated into a pRGEN-CAS9 (developed in-house) vector using a BsmBI site. Cas9 and the sgRNa including a variable target sequence at the 5' end were expressed through the CMV and U6 promoters, respectively.

Furthermore, for a delivery system by RNP, the sgRNA was transcribed by T7 RNA polymerase after a template was produced by annealing two partially complementary oligonucleotides produced by Phusion Taq-mediated polymerization. The transcribed sgRNA was purified and quantified using spectrometry.

3. Purification of Cas9 Protein

Codon-optimized Cas9 DNA sequences including NLS and HA epitopes were subcloned into a pET28 vector and expressed in BL21 (DE3) using IPTG under optimal culture conditions. The expressed Cas9 protein was purified using Ni-NTA agarose beads and dialyzed with an appropriate buffer. The activity of Cas9 was confirmed through an in vitro cleavage test using a well-known effective sgRNA.

4. Cell Culture

A human Schwann-like cell line (ATCC) and human primary Schwann cells (ScienCell) were cultured according to the manufacturer's manual. The human Schwann-like cells were cultured in Dulbecco's modified Eagle's medium (DMEM) (WelGene) containing a high concentration of glucose supplemented with 1× penicillin/streptomycin (Wel-Gene) and 10% fetal calf serum (WelGene).

The human primary Schwann cells were maintained in a Schwann cell culture solution (ScienCell) provided by a vendor. For differentiation, the cells were cultured in DMEM (WelGene) containing a low concentration of glucose supplemented with a 1% fetal calf serum (WelGene), 100 ng/mL Nrg1 (Peprotech) for myelin sheath formation (myelination) signals, and 100 UM dbcAMP (Sigma-Aldrich) for 7 days.

5. Transduction (Transfection)

For transduction (transfection), an RNP complex containing 4 μg of the Cas9 protein (ToolGen) and 1 μg of sgRNA was incubated at room temperature for 15 minutes. Thereafter, the RNP complex was electroporated by using a 10 μl electroporation tip and a Neon electroporator (ThermoFisher) and delivered to $2\times10^5$ cells. For targeted deep sequencing, genomic DNA (gDNA) was collected from transduced cells 72 hours after transduction.

6. In Vitro Real Time PCR (qRT-PCR)

mRNA was extracted from human primary Schwann cells according to the manufacturer's protocol using an RNeasy minikit (Qiagen). Thereafter, 100 ng mRNA was reverse transcribed using a high-capacity cDNA reverse transcription kit (ThermoFisher). qRT-PCR was performed with 10 ng of Taqman Gene expression master mix according to the manufacturer's protocol using QuantStudio 3 (ThermoFisher). PMP22 expression levels were calculated using Ct values, and GAPDH was used as an endogenous control. The Taqman probes (ThermoFisher) used in the present study are summarized in Table 8 below.

TABLE 8

| Target Gene | Taqman Gene Experssion Assay | Accession number |
|---|---|---|
| PMP22 | Hs00165556_m1 | NM_000304.3 |
| GAPDH | HS02786624_g1 | NM_001256799.2 |

7. Targeted Deep Sequencing

An on-target site was amplified by PCR from gDNA extracted from transduced cells using Phusion polymerase taq (New England BioLabs). Thereafter, paired-end deep sequencing was performed using Mi-Seq (Illumina) as the PCR amplification product. The deep sequencing results were analyzed using an online Cas-Analyzer tool (www.rgenome.net). It was confirmed whether a mutation occurred at 3 bp upstream from a PAM sequence as a result of indels by Cas9. The primers used in the present study are summarized in Table 8 below.

TABLE 9

| | Target site | Primer-F (5' to 3') | Primer-R (5' to 3') |
|---|---|---|---|
| On-Target | hPMP22-TATA | CACAGGGCAGTCAGAGACCC (SEQ ID NO: 67) | GCAAACAAAG TTGGACACTG (SEQ ID NO: 68) |
| | mRosa26 | AGACTCCCGCCCATCTTCTAG AAA (SEQ ID NO: 69) | AAGTCGCTCTGAGTTGTTATCA GT (SEQ ID NO: 70) |
| | AAVS1 | CAGTGAAACGCACCAGACG (SEQ ID NO: 71) | AATCTGCCTAACAGGAGGTG (SEQ ID NO: 72) |
| Off-target (In silico, in vitro) | hPMP22-TATA Off1 | GAGGGAATGGGGACCAAAGG CATT (SEQ ID NO: 73) | TCATGTGGGGTGATGTTCAGG AAG (SEQ ID NO: 74) |
| | hPMP22-TATA Off2 | AGAGCAGCTGACCTGAGGTCC AA (SEQ ID NO: 75) | CCCAAGGGTAGAGTGCAAGTA AAC (SEQ ID NO: 76) |
| | hPMP22-TATA Off3 | GCATCCTAGCTCATTTGGTCTG CT (SEQ ID NO: 77) | GAGAGGATTCCTCATGAATGG GAT (SEQ ID NO: 78) |
| | hPMP22-TATA Off4 | ACCAAACACTACACTTGGTTAC TG (SEQ ID NO: 79) | CTCCCACTAGCAATTTTAAAGT CT (SEQ ID NO: 80) |
| | hPMP22-TATA Off5 | GAATGTTCAGCACAGGTTTCC TTG (SEQ ID NO: 81) | GGTCAAAAGGAGCTCCATATTT GA (SEQ ID NO: 82) |

TABLE 9-continued

|  | Target site | Primer-F (5' to 3') | Primer-R (5' to 3') |
|---|---|---|---|
|  | hPMP22-TATA Off6 | CAGGACACCCATGGCCAAATCCAG (SEQ ID NO: 83) | CAGAGCCTCCTGCAGGGATGTCAA (SEQ ID NO: 84) |
|  | hPMP22-TATA Off7 | GCCTGCCAAGGTGACTCTCATCTA (SEQ ID NO: 85) | TGCCCAGGCTGATCTTGAACTCCT (SEQ ID NO: 86) |
|  | hPMP22-TATA Off8 | CCCAGAGTTAAGAGGTTCTTTCCT (SEQ ID NO: 87) | GAAGCTACTCCAGTGCAACTAGCT (SEQ ID NO: 88) |
|  | hPMP22-TATA Off9 | ACGCAGTCTGTTCTGTGCAGTGT (SEQ ID NO: 89) | AGGCCTTCCCAAGGAAGACCCTGA (SEQ ID NO: 90) |
|  | hPMP22-TATA Off10 | GCTGATCACTGGCCAAATCCAGCT (SEQ ID NO: 91) | GGGAAACAATGGGATCAAGCTGCA (SEQ ID NO: 92) |
|  | hPMP22-TATA Off11 | GCCCCTTTGTAAGTTGAGGAGCAT (SEQ ID NO: 93) | CCCTCTACCTCTCAATGGGCTT (SEQ ID NO: 94) |
|  | hPMP22-TATA Off12 | CAGACAAGCAAATGCTGAGAGATT (SEQ ID NO: 95) | CCTGTCATTATGATGTTCGCTAGT (SEQ ID NO: 96) |
|  | hPMP22-TATA Off13 | CCAGAGTTGGCCTCCTACAGAGAT (SEQ ID NO: 97) | GTGGATGCCCCACTACTGTTCATT (SEQ ID NO: 98) |
|  | hPMP22-TATA Off14 | TACCCAATTTGCCAGTCTGTGTCT (SEQ ID NO: 99) | ACCACCAGGCCTGCCCTACAAGA (SEQ ID NO: 100) |
|  | hPMP22-TATA Off15 | TGTGAATTTGATCCTGGCATTATG (SEQ ID NO: 101) | TACAGACAAGCAGATGCTGAGAGA (SEQ ID NO: 102) |
|  | hPMP22-TATA Off16 | CAGTCAACAGAGCTCTAACCTCCT (SEQ ID NO: 103) | AGCACCTGGTTGCACATCAACTT (SEQ ID NO: 104) |
|  | hPMP22-TATA Off17 | CATGTGGTCCCTGAACGTGAATGA (SEQ ID NO: 105) | GTCTGTCGCTTGCCCTCTTCTCT (SEQ ID NO: 106) |
|  | hPMP22-TATA Off18 | ATGCAGGGCCTCTAGACCATTTCA (SEQ ID NO: 107) | CTCAGCCCTTTGTGCACTCACCT (SEQ ID NO: 108) |
| Off-target (Digenome-seq, in vitro) | hPMP22-TATA Off1 | TGCACATCGCAAACATTTCG (SEQ ID NO: 109) | TGGGTATCGCACTGTGTCAG (SEQ ID NO: 110) |
|  | hPMP22-TATA Off2 | AGGTTCACATGGCTTGTGGT (SEQ ID NO: 111) | ATATCTGAAATGCCCGCAGG (SEQ ID NO: 112) |
|  | hPMP22-TATA Off3 | TGCACATCGCAAACATTTCG (SEQ ID NO: 113) | TGGGTATCGCACTGTGTCAG (SEQ ID NO: 114) |
|  | hPMP22-TATA Off4 | TCTTTAAAGGCCTTATCTCC (SEQ ID NO: 115) | TTCTGCTTGAGAATTCATCC (SEQ ID NO: 116) |
|  | hPMP22-TATA Off5 | CTCCTAATCTTTCACTTAGG (SEQ ID NO: 117) | CAAAGCCTGGTATAACATAG (SEQ ID NO: 118) |
|  | hPMP22-TATA Off6 | TCACTTCGAGCATCTGTGG (SEQ ID NO: 119) | CCAAATGACAGGCTGAGCT (SEQ ID NO: 120) |
|  | hPMP22-TATA Of17 | AGCAGGAAGTGAAGGCTAAG (SEQ ID NO: 121) | ATGTAACGTGGCAACTCTGG (SEQ ID NO: 122) |
|  | hPMP22-TATA Off8 | GTGTTGCTCTCGTCAATTAG (SEQ ID NO: 123) | AGGTGTTGTACATGGAGAAG (SEQ ID NO: 124) |
|  | hPMP22-TATA Off9 | TGTGAGCCACCATACCCAGC (SEQ ID NO: 125) | CCTGCAGTCCTTTGCGGATC (SEQ ID NO: 126) |
| Off-target (In silico, In vivo) | hPMP22-TATA Off1 | TCGCTGCCAGTATAACATGC (SEQ ID NO: 127) | AACTCCAGTCTCTAGACTCG (SEQ ID NO: 128) |
|  | hPMP22-TATA Off2 | AATAGTTTGACGTTGGAGCC (SEQ ID NO: 129) | ACTCCCAACATGTTCTCCTG (SEQ ID NO: 130) |
|  | hPMP22-TATA Off3 | ATCATCGCTCACAGAGTCC (SEQ ID NO: 131) | ACGACTGCAGGATCTTAATG (SEQ ID NO: 132) |
|  | hPMP22-TATA Off4 | TGGATGGAGGTTGGGAATCC (SEQ ID NO: 133) | TTGAGGCAGCAGCACTCTCC (SEQ ID NO: 134) |
|  | hPMP22-TATA Off5 | AGTCTATCCTAGCAGCTCC (SEQ ID NO: 135) | ACTGAGACCAGATAATGCAG (SEQ ID NO: 136) |
|  | hPMP22-TATA Off6 | AAGAGATGCGAGTTGTTCC (SEQ ID NO: 137) | CCTCTTCTACTCTGAGTGG (SEQ ID NO: 138) |
|  | hPMP22-TATA Off7 | ACCTGGTTTATCACAAGCTA (SEQ ID NO: 139) | AACGTGAACAGAAGGATTTC (SEQ ID NO: 140) |
|  | hPMP22-TATA Off8 | ATCACTCCATCAGAGTCAGG (SEQ ID NO: 141) | TGGCTCCTTCTATTCTCTCC (SEQ ID NO: 142) |

8. Design of in Silico Off-Target Site

An off-target potential site was designed in silico using an online tool (www.rgenome.net). A maximum of a 3 bp mismatch was considered as an off-target site.

9. Digenome-Seq

Genomic DNA of Hela cells was purified according to the vendor's protocol using a DNeasy Blood & Tissue Kit (Qiagen). The Cas9 protein (100 nM) and the sgRNA (300 nM) incubated in advance were mixed with genomic DNA (10 µg) in 1 mL of a reaction solution (100 mM NaCl, 50 mM Tris-HCl, 10 mM MgCl2, 100 µg/ml BSA, PH 7.9) at 37° C. for 8 hours. Truncated genomic DNA was treated with RNase A (50 µg/mL), and purified again using a DNeasy Tissue Kit (Qiagen). 1 µg of the truncated genomic DNA was split into fragments using a Covaris system, and an adaptor for producing a library was connected to the DNA fragments. Thereafter, the library was subjected to whole genome sequencing (WGS) using a HiSeq×Ten Sequencer (Illumina) at a sequencing depth of 30 to 40× (Macrogen). In vitro cleavage scores were calculated by a DNA cleavage scoring system at the positions of each base sequence cleaved in the genome.

10. Mice and Intraneural Injection

C22 mouse lines (B6; CBACa-Tg (PMP22) C22Clh/H) used in the present study were purchased from MRC Harwell (Oxfordshire, UK). C22 mice (4 males and 7 females) were treated with PMP22-TATA RNP. Intraneural injection was performed in the same manner as a previous study (Daisuke Ino., J Vis Exp., (2016) 115). 6-day old mice were anesthetized, and the mouse sciatic nerves were exposed by surgery. In order to minimize nerve damage, intraneural injection was immediately performed at the end of the sciatic notch was immediately using a pulled glass micropipettes attached to a microinjector. An RNP complex of 11 µg of the Cas9 protein and 2.75 µg of sgRNA per mouse was injected into the mice along with Lipofectamine 3000 (Invitrogen, Carlsbad, CA, USA). The management, use, and treatment of all animals used in the present study were performed under the guidelines prepared by the Samsung Animal Management and Use Committee (SMC-20170206001) in accordance with the Association for Assessment and Accreditation of Laboratory Animal Care International.

11. Rotarod Experiment (Rotarod Test)

Motor coordination was evaluated using a rotarod device (B.S. Technolab INC., Korea). This experiment was performed to evaluate the balance and motor coordination of the mice. Prior to the experiment, mice went through a 3-day training period. In the experiment, a horizontal rotating rod (21 rpm) was used for the rotarod experiment. The retention time on the rotating rod of the mouse was measured, and the mouse was allowed to stay on the rod for up to 300 seconds.

12. Electrophysiological Test

In order to evaluate the electrophysiological state, a nerve conduction test (NCS) was performed in the same manner as in a previous study (Jinho Lee., J Biomed Sci., (2015) 22, 43). In summary, mice were anesthetized with carbon dioxide gas, and the anesthesia was maintained using a nose cone to supply 1.5% isoflurane during the experiment. Hair was completely removed from the end to the hind paw. The NCS was performed using a Nicolet VikingQuest device (Natus Medical). For a motor nerve conduction test of the sciatic nerve, responses from a distal part and a proximal part were each determined by placing an activity recording needle electrode on the gastrocnemius muscle with a reference electrode attached to the tendon, and disposing a stimulating negative electrode at a position close to a recording electrode at a distance of 6 mm toward the body center inside the hip and the center line of the post-orbital portion thigh. The distal latency (DL), the motor nerve conduction velocity (MNCV), and the amplitude of the compound muscle action potential (CMAP) were measured. The CMAP was measured at the maximal overstimulation.

13. Nerve Histology and Images

The sciatic nerves of the mice were biopsied and a pathological examination of the affected sample was performed by analysis with a microscope. The samples were respectively fixed using a 25 mM cacodylate buffer containing 2% glutaraldehyde. Semi-thin sections were stained with toluidine blue. After incubation in 1% $OsO_4$ for 1 hour, the samples were dehydrated in an ethanol series, and then allowed to pass through propylene oxide and embedded in an epoxy resin (Epon 812, Oken, Nagano, Japan). The cells were sliced to a certain thickness (1 µm) using Leica ultra-microtome (Leica Microsystems), and stained with toluidine blue for 30 to 45 seconds. The g-ratio (axon diameter/fiber diameter) was calculated by measuring the inner diameter and the outer diameter of myelin using the Zeiss Zen 2 program (Carl Zeiss, Oberkochen, Germany).

14. Statistical Analysis

The statistical significance of data associated with mRNA expression levels was evaluated by a one-way ANOVA using multiple comparisons of post-hoc Tukey's. Other types of presented data were calculated using a Mann-Whitney U test (http://www.socscistatistics.com/tests/mann-whitney/Default2.aspx). Data and graphs produced from the present study were analyzed using GraphPad Prism. The significance level was set at 0.05.

Example 1. sgRNA Screening

In order to screen for therapeutically effective sgRNA sequences which may reduce the expression of human PMP22 to a normal range, human cell lines were transduced with various sgRNAs and Cas9s designed to target coding sequences (CDS) and TATA-box and intronic enhancer binding sites of a PMP gene. In brief, Jurkat human T cells were used for SpCas9 screening, and HEK293T cells were used for CjCas9. gDNA was collected from the cells and subjected to targeted deep sequencing. Various patterns of mutations induced by the sgRNA sequences were identified by an NHEJ-mediated indel. Several SpCas9-sgRNAs strongly induced indels in CDS and two regulatory sites (FIG. 1). It was confirmed that 30 to 40% of indels were induced in a specific CjCas9-sgRNA (FIG. 2).

Example 2. Gene Manipulation of Schwann-Like Cells

Although effective indel mutations caused by sgRNA were identified in human cells, it is uncertain whether the effect would also be possible in Schwann cells. Thus, in order to investigate the effects of PMP22 expression inhibition and gene manipulation in Schwann cells, the SpCas9-sgRNA effect was confirmed using sNF2.0 cells, which are Schwann-like cells. The effective SpCas9-sgRNA identified in Jurkat cells was repeatedly tested in sNF02.0 cells. After transduction, it was confirmed through deep sequencing analysis that the same high indel frequency was obtained by the same sgRNA. In particular, it was confirmed that almost 70 to 80% of the indels were in a frame shift of PMP22 occurring due to the sgRNA targeting CDS (FIG. 4). Transduction of a single sgRNA targeting promoter (TATA-box) site and enhancer-binding positions induced indels of 31% and 59%, respectively (FIG. 3). Interestingly, a 40 to 50 bp small deletion containing a main controlling factor (for example, EGR or SOX10-binding position) of a myelin gene, or an important TATA-box was found in a very large number of cells of cells treated with dual sgRNA (FIG. 5).

Example 3. Expression Control of PMP22 by Gene Manipulation

Figure 6:
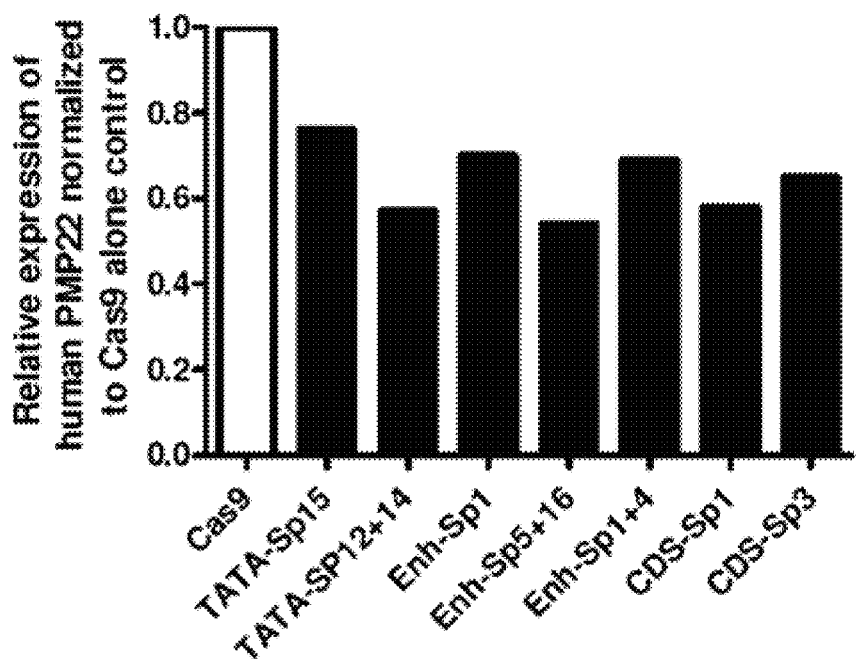
FIG. 6 is a graph illustrating a decrease in mRNA expression of human PMP22 by SpCas9-sgRNA in human Schwann-like cells.

In order to evaluate the change in expression of PMP22 by an effective sgRNA, Schwann-like cells were differentiated, and qRT-PCR was performed. As a result, most of the sgRNAs targeting PMP22 effectively inhibited the expression of PMP22 (FIG. 6). When single sgRNA was used, the expression of PMP22 was decreased by about 30% as compared to a control treated with only Cas9, and when dual sgRNA was used, the expression of PMP22 was decreased by about 50% as compared to the control treated with only Cas9.

Example 4. Gene Manipulation of Schwann Cells

Figure 7A:
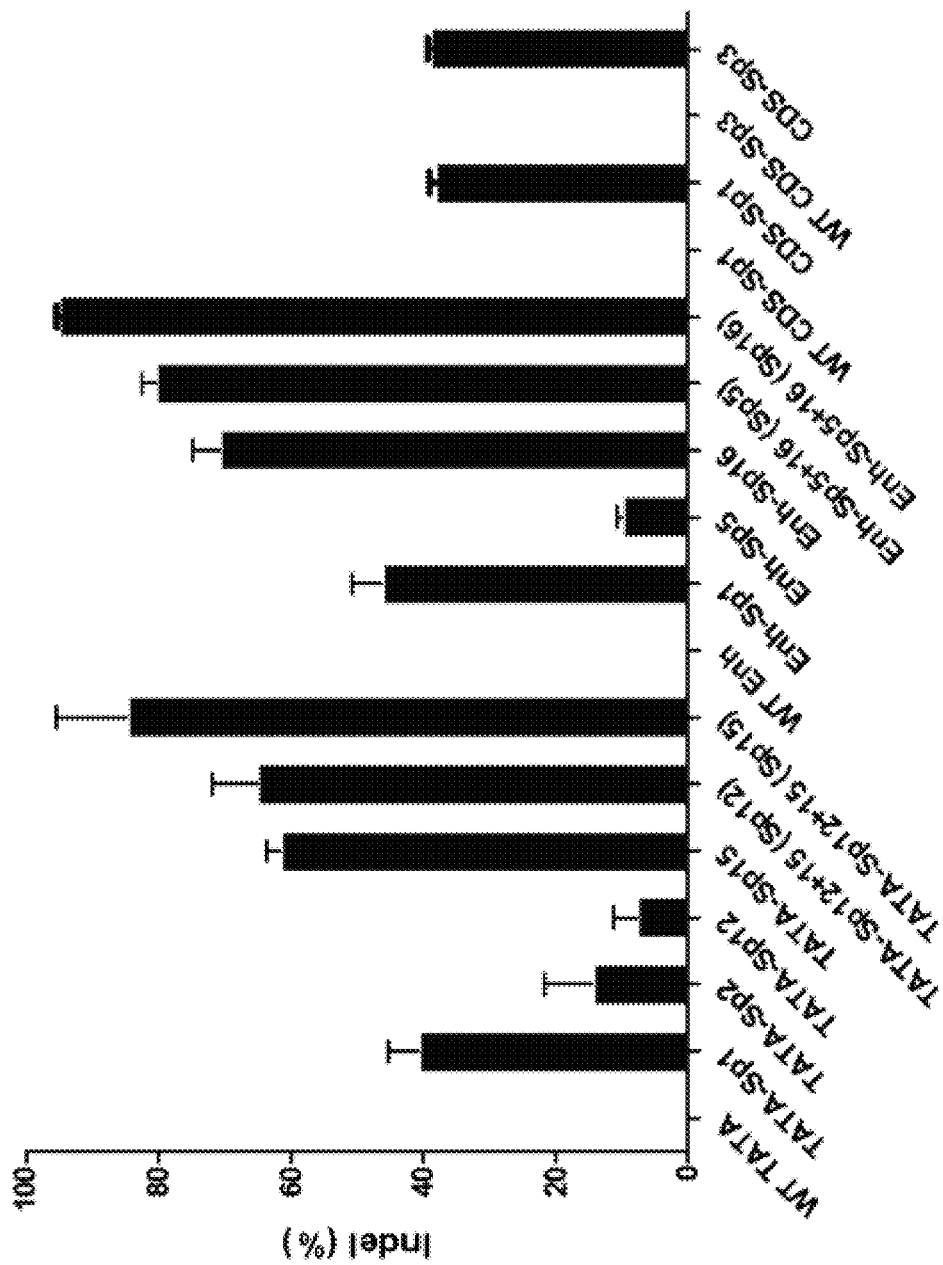
FIG. 7 is a graph illustrating effective and specific expression decreases of PMP22 by SpCas9-sgRNA at each target site of a human PMP22 gene in human primary Schwann cells, and (a) illustrates indel frequency measurement results by SpCas9-sgRNA at each target site, (b) illustrates relative mRNA expression comparison results of PMP22, which are measured by qRT-PCR with or without a treatment of a myelination signal factor and an RNP complex for each target site (n=3, One-way ANOVA and Tukey post-hoc tests: *p<0.05), and (c) illustrates indel frequency measurement results by SpCas9-sgRNA targeting distal enhancer sites (distal enhancer regions) B and C.

After expression inhibition and gene manipulation effects of PMP22 were previously confirmed in Schwann-like cells, it was confirmed whether the previous result exhibited a similar effect in human primary Schwann cells. The indel frequency according to the target site was observed using the SpCas9-sgRNA at each target site of the human PMP22 gene in human primary Schwann cells. As a result, it was confirmed that the indel frequency was high at the target site in most of the sgRNAs targeting TATA-box, enhancer, and coding sequences of the PMP22 gene (FIG. 7A). Further, even when dual sgRNAs each targeting TATA-box and an enhancer was used, a high indel frequency was exhibited. It was confirmed that an indel occurred at the target site using an sgRNA additionally targeting sequences encoding distal enhancer sites B and C (FIG. 7C), and in this case, an sgRNA targeting APOC3 was used as a control.

Figure 7B:
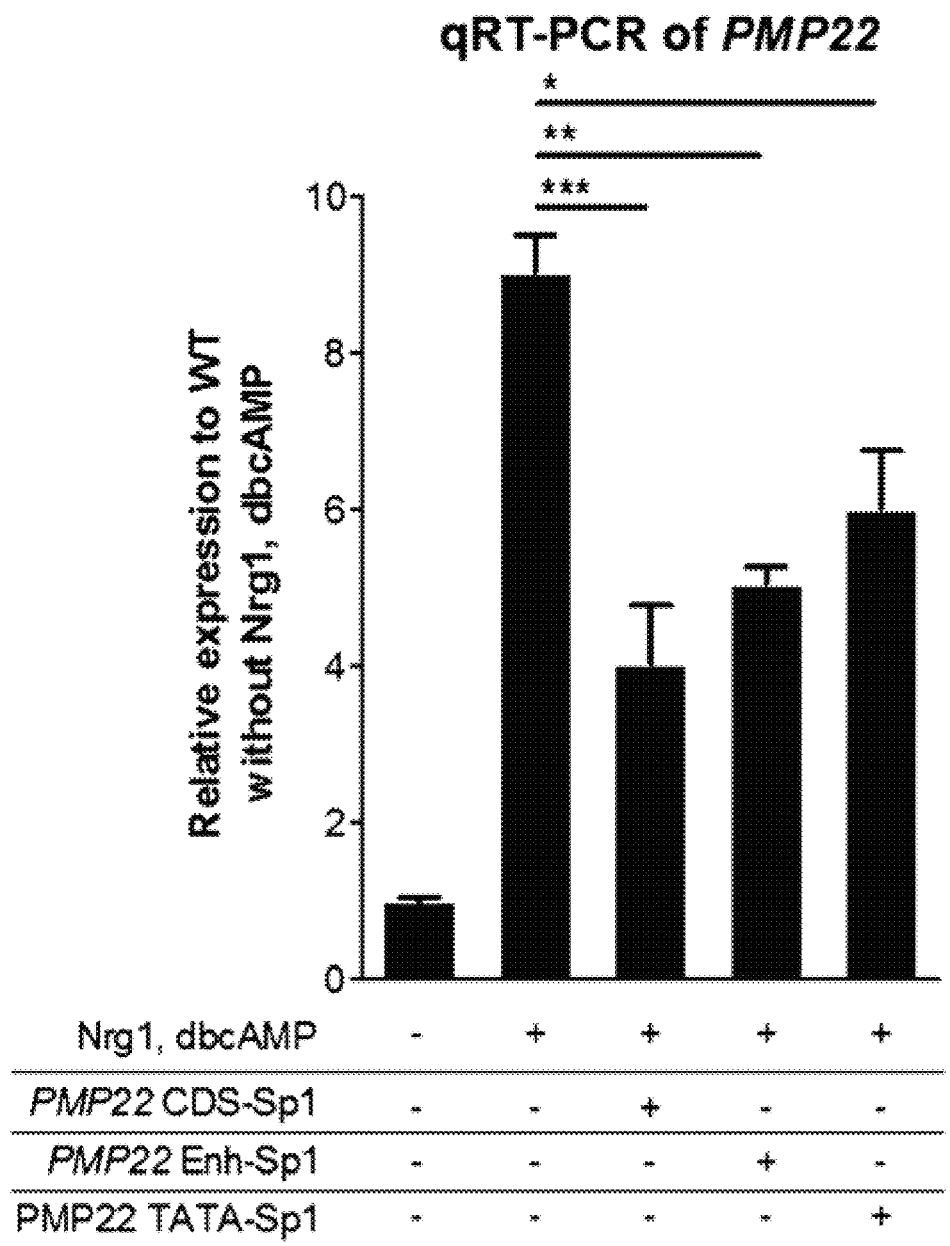
Figure 7C:
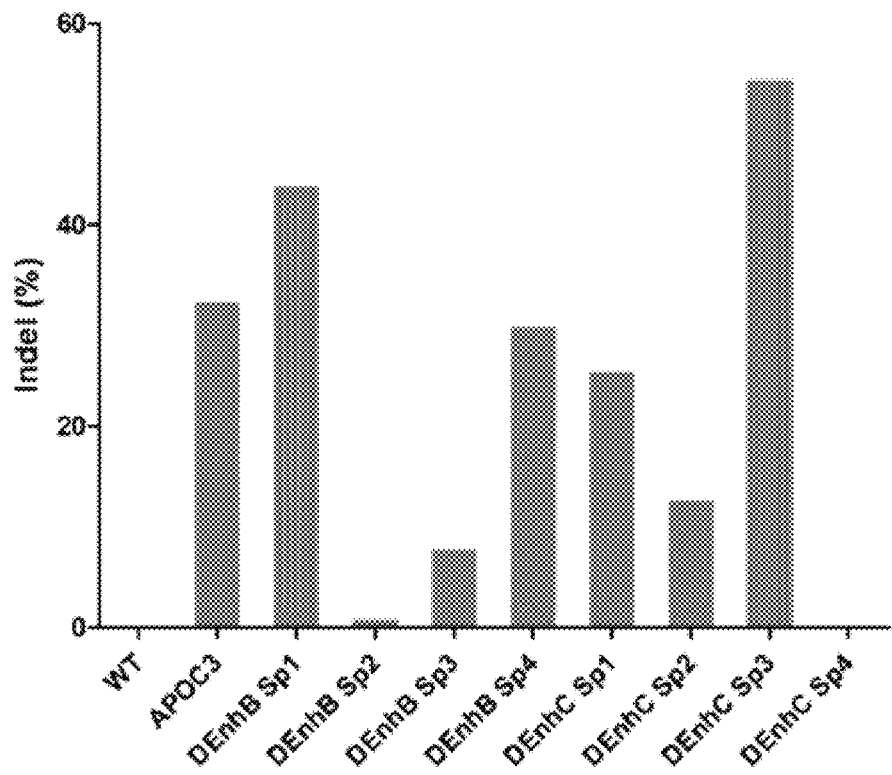

In addition, in order to confirm whether the SpCas9-sgRNA at each target site causes a decrease in expression of the PMP22 gene, a qRT-PCR analysis was performed. Since PMP22 is transcribed at the final stage of differentiation of Schwann cells, human primary Schwann cells were treated with a well-known different signal factor including Neuregulin-1 (Nrg1) and dibutyryl cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, when cells were treated with SpCas9-sgRNA at each target site, it was confirmed that the expression of PMP22 was induced 4 to 6-fold. This is determined to be due to the expression inhibition of PMP22 due to each target site modification of PMP22 by SpCas9-sgRNA at each target site (FIG. 7B).

Figure 8A:
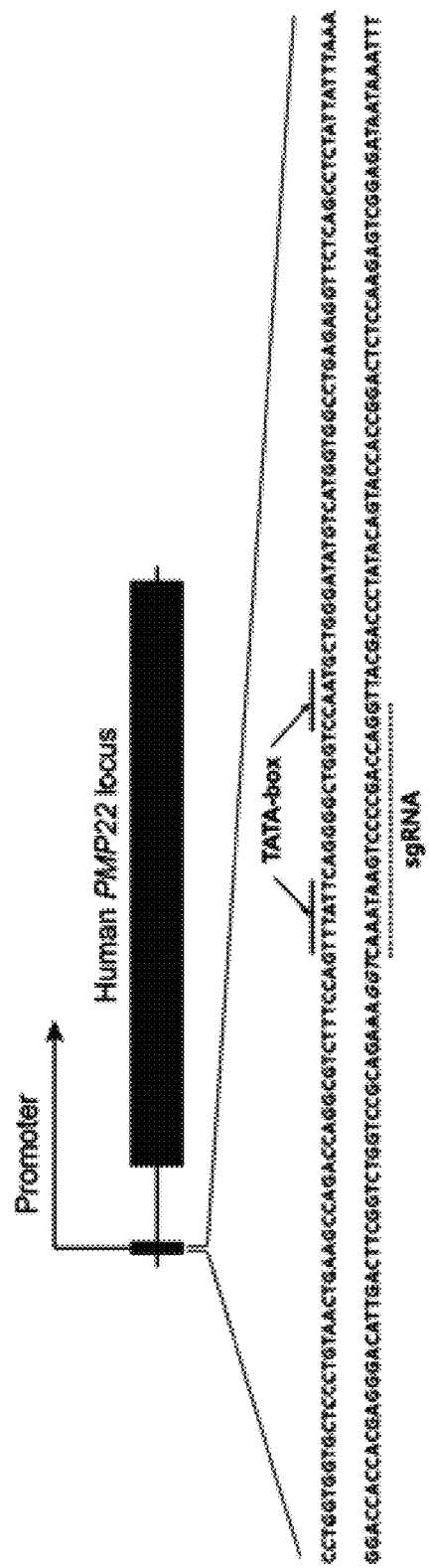
FIG. 8 is a graph illustrating effective and specific expression decreases of PMP22 through CRISPR-Cas9 targeting a TATA-box site of a human PMP22 gene in vitro, and (a) illustrates a target sequence targeting a promoter site of a human PMP22 position, and the leftmost graph, the middle graph, and the rightmost graph in (b) illustrate indel frequency measurement results using targeted deep sequencing in human primary Schwann cells, TATA-box 1 mutation frequency measurement results (n=3) among the total indel frequencies, and relative mRNA expression comparison results of PMP22, which are measured by qRT-PCR with or without a treatment of a myelination signal factor and an RNP complex in human primary Schwann cells (n=3, One-way ANOVA and Tukey post-hoc tests: *p<0.05), respectively. The sequence shown in FIG. 8A represents SEQ ID NO: 252.
Figure 8B:
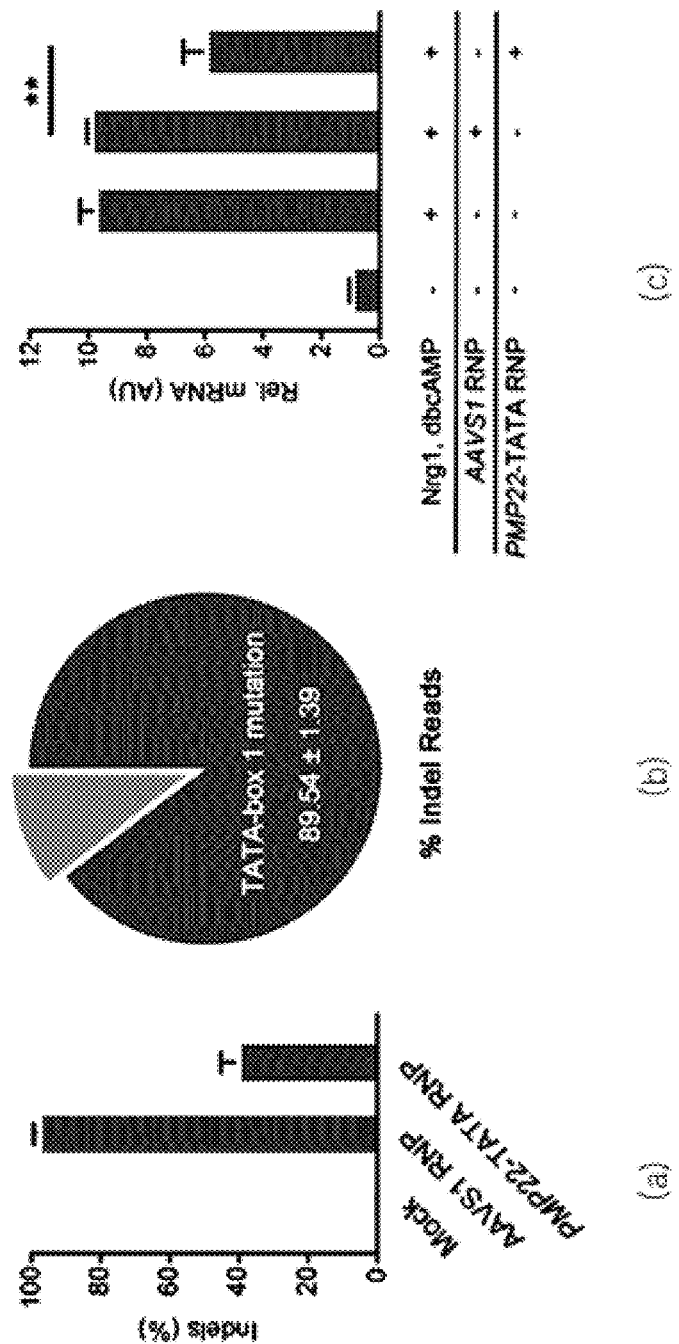

Example 5. Effects of Decrease in Effective and Specific Expression of PMP22 Using CRISPR/Cas9 Targeting TATA-Box Site of Human PMP22 Gene An experiment was performed in human primary Schwann cells by selecting sgRNA_TATA_Sp #1 (hereinafter, described as PMP22-TATA sgRNA) which exhibits a high indel efficiency among sgRNAs targeting a TATA-box site previously screened and may target the TATA-box. An indel was induced by transducing human primary Schwann cells with an RNP complex including an sgRNA and Cas9 protein (FIG. 8B), and it was confirmed through a targeted deep sequencing analysis that 89.54±1.39% of the total indels were generated at the TATA-boxy site of human PMP22 (FIG. 8C).

In addition, to confirm whether a mutation formed at the TATA-box of PMP22 caused a decrease in expression of the PMP22 gene, a qRT-PCR analysis was performed. Since PMP22 is transcribed at the final stage of differentiation of Schwann cells, human primary Schwann cells were treated with a well-known different signal factor including Neuregulin-1 (Nrg1) and dibutyryl cyclic AMP (dbcAMP) for 7 days. As a result, it was confirmed that the expression of PMP22 was increased by 9 times in cells treated with Nrg1 and dbcAMP as compared to cells which were not treated with Nrg1 nor dbcAMP. In contrast, it was confirmed that when cells were treated together with PMP22-TATA RNP, the expression of PMP22 was induced 6-fold. This is determined to be due to expression inhibition of PMP22 by TATA modification of PMP22 by CRISPR/Cas9 (FIG. 8D). In a control treated with both the differentiation signal factor and the AAVS1 target RNP, no difference in differentiation of the PMP22 gene could be confirmed.

Figure 9A:
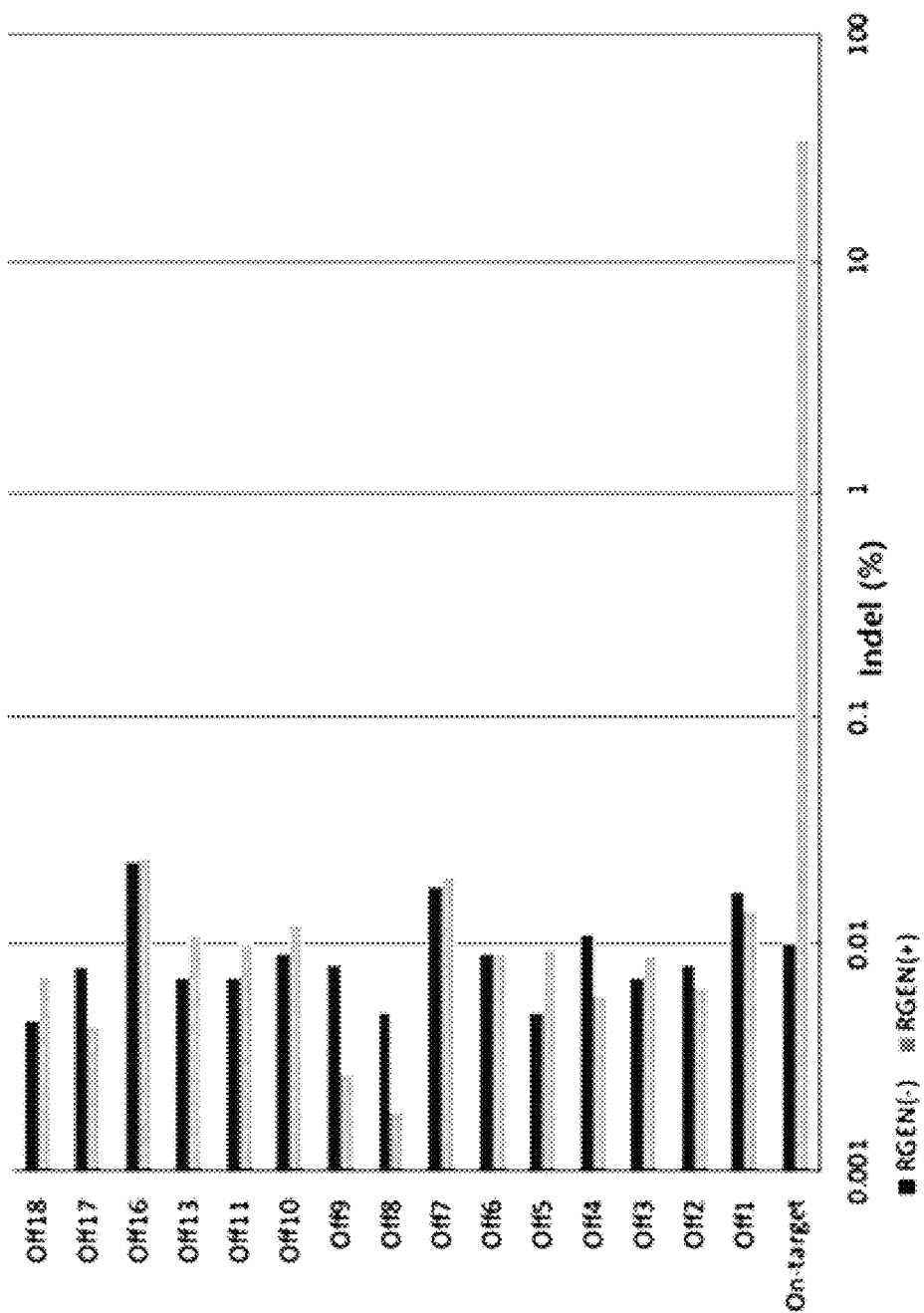
FIG. 9 illustrates indel frequencies by PMP22-TATA RNP in off-targets and on-targets found through an in silico off-target analysis by target deep sequencing in human primary Schwann cells, and (a) is a graph illustrating indel frequencies, (b) illustrates indel patterns with a high frequency, and (c) shows off-target positions found through an in silico off-target analysis. The wildtype sequence and indel sequences −1, −2, +1, −3, and −4 of FIG. 9B are represented by SEQ ID NOs: 210-215, respectively. The on-target and Off1-Off18 sequences of FIG. 9C are represented by SEQ ID NOs: 216-234, respectively.
Figure 10A:
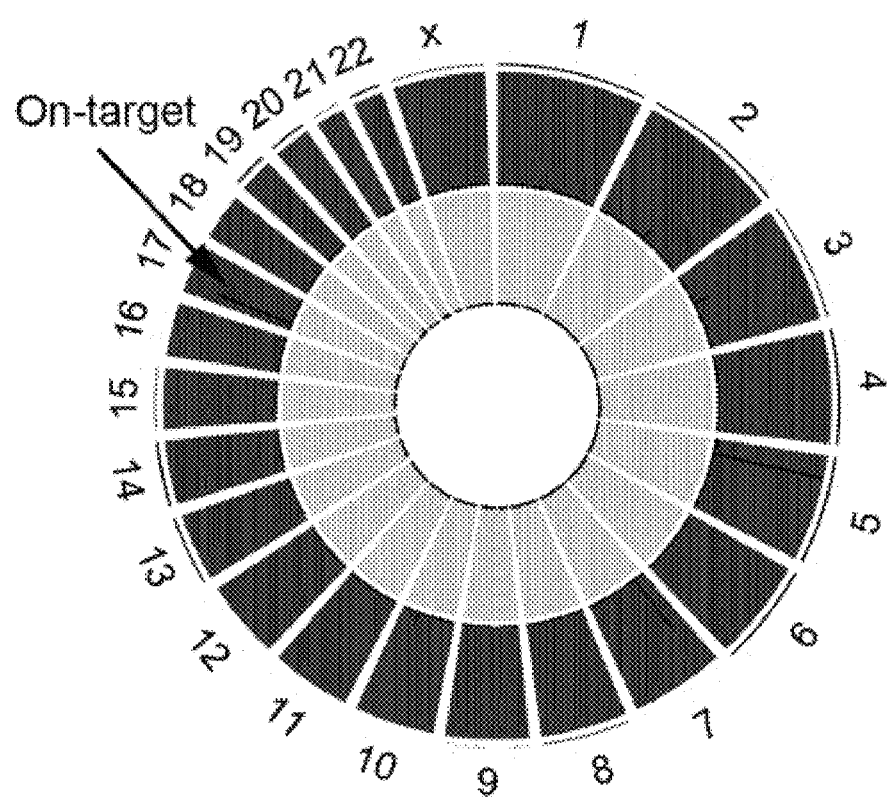
FIG. 10 is a set of results illustrating positions cleaved by PMP22-TATA RNP in a human's entire genome, and (a) illustrates a Genome-wide Circos plot, (b) illustrates off-target positions appearing by the Digenome-seq among off-target positions found through an in silico off-target analysis, and (c) is a graph illustrating indel frequencies in off-target positions. The on-target and Off1-Off9 sequences of FIGS. 10B and 10C are represented by SEQ ID NOs: 216 and 235-243, respectively.
Figure 10C:
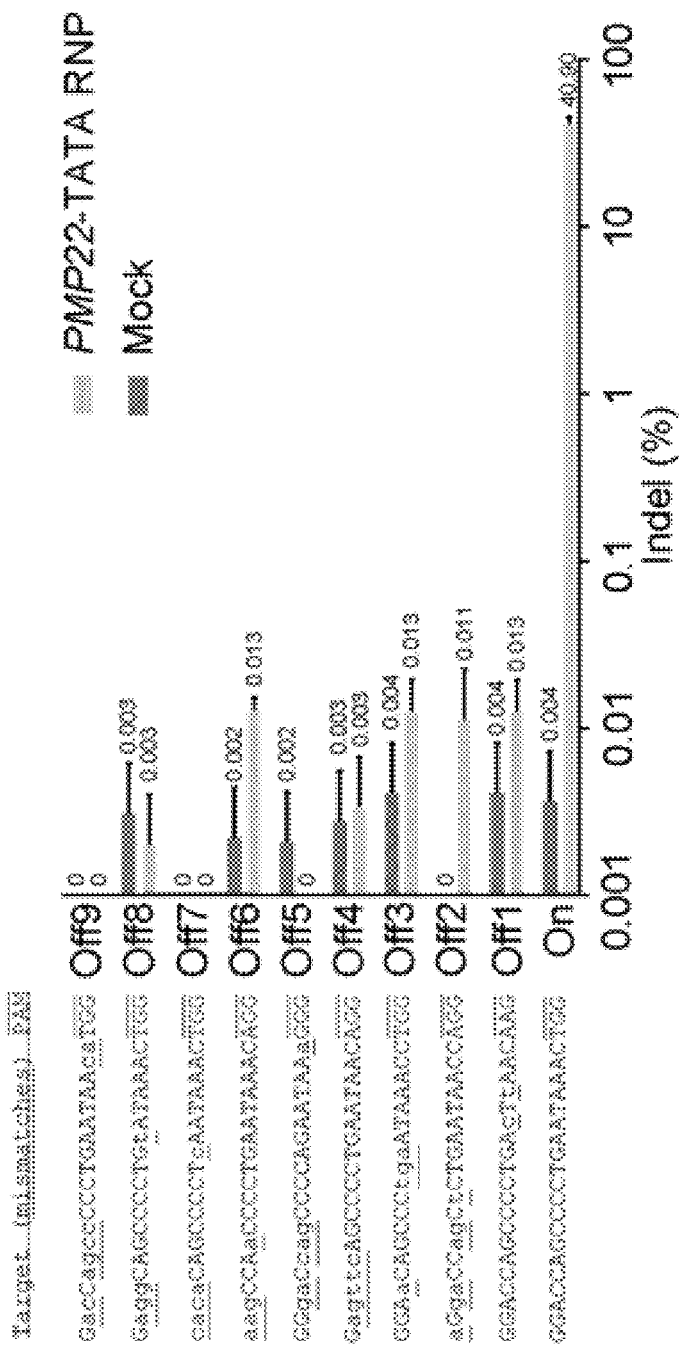

In order to confirm the specificity of PMP22-TATA RNP, an in silico-based off-target analysis was performed. Through the targeted deep sequencing, no indel mutation exceeding a sequencing error ratio (0.1% on average) was confirmed at the off-target position confirmed by an in silico analysis (FIG. 9). Since the in silico-based off-target analysis may be a biased approach, Digenome-seq (a whole sequencing-based off-target analysis which is not biased) was also performed. As a result, it was possible to confirm nine off-target positions cleaved by PMP22-TATA RNP in vitro (FIG. 10A, FIG. 10B). However, as a result of a re-analysis through the targeted deep sequencing, an abnormal indel mutation was not found at the off-target position (FIG. 10C).

These results show that the effective and specific modification of the TATA-box of PMP22 by PMP22-TATA RNP may control the transcription level of PMP22 in human primary Schwann cells.

Figure 11:
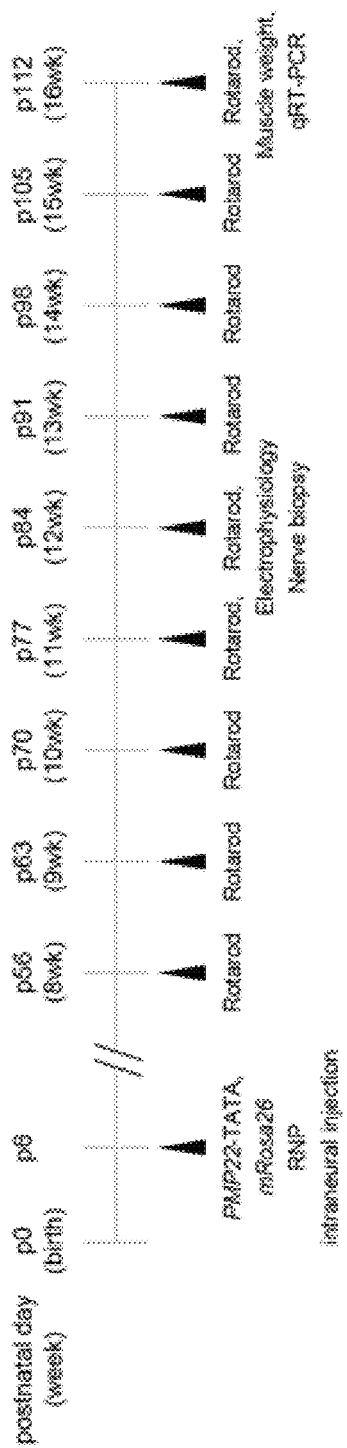
FIG. 11 schematically illustrates a therapeutic approach using PMP22-TATA RNA therapy in C22 mice.
Figure 12:
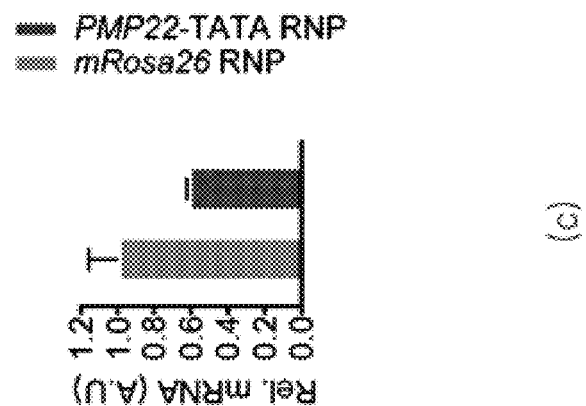
FIG. 12 is a set of results illustrating the alleviation of a disease phenotype through expression inhibition of PMP22 by CRISPR/Cas9 in CMT1A mice, and (a) is a graph illustrating indel frequencies using targeted deep sequencing in a sciatic nerve treated with mRosa26 or a PMP22-TATA RNP complex (n=3), (b) is a TATA-box 1 mutation frequency measurement result (n=3) among the total indel frequencies, and (c) is a graph comparing the relative amounts of mRNA expressed of PMP22 using qRT-PCR from the sciatic nerve treated with mRosa26 or a PMP22-TATA RNP complex.
Figure 12:
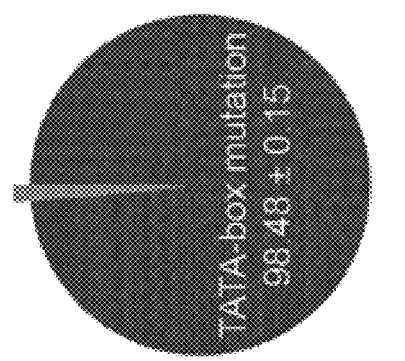
Figure 12:
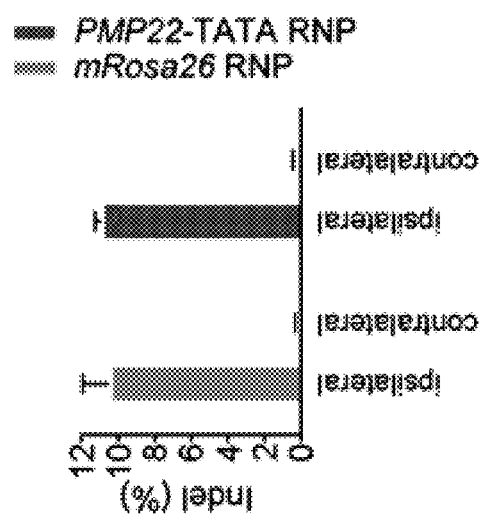

Example 6. Alleviation Effects of Disease Phenotype by Expression Inhibition of CRISPR/Cas9-Mediated PMP22 in CMT1A Mice In order to test the PMP22 transcription control by PMP22-TATA RNP in vivo, PMP22-TATA RNP enclosed by liposomes was directly injected into the sciatic nerve of the C22 mouse (FIG. 11). In this case, an RNP complex targeting Rosa26 (mRosa26) was used as a control. mRosa26 RNP or PMP22-TATA RNP was injected intraneurally into and delivered to the left sciatic nerve (ipsilateral) of a 6-day old (p6) mouse, and the right sciatic nerve was used as an internal control (contralateral). Four weeks after injection, the intraneural delivery efficiency of the RNP complex was confirmed through targeted deep sequencing by collecting genomic DNA from the sciatic nerve. As a result, all the sciatic nerves treated with mRosa26 RNP and PMP22-TATA RNP showed indel efficiencies of about 11% (FIG. 12A). Further, a TATA-box mutation of 98.48±0.15% was confirmed in the overall indel sequencing read consistent with the in vitro results (FIG. 12B).

In addition, in order to confirm the expression inhibition of PMP22 by the TATA-box mutation in vivo, a qRT-PCR analysis of mRNA extracted from the whole sciatic nerve was performed on the RNP-treated sciatic nerve. Similar to the in vitro results, it was confirmed that the expression of the PMP22 gene was reduced by 38% as compared to the control (FIG. 12C).

Figure 13B:
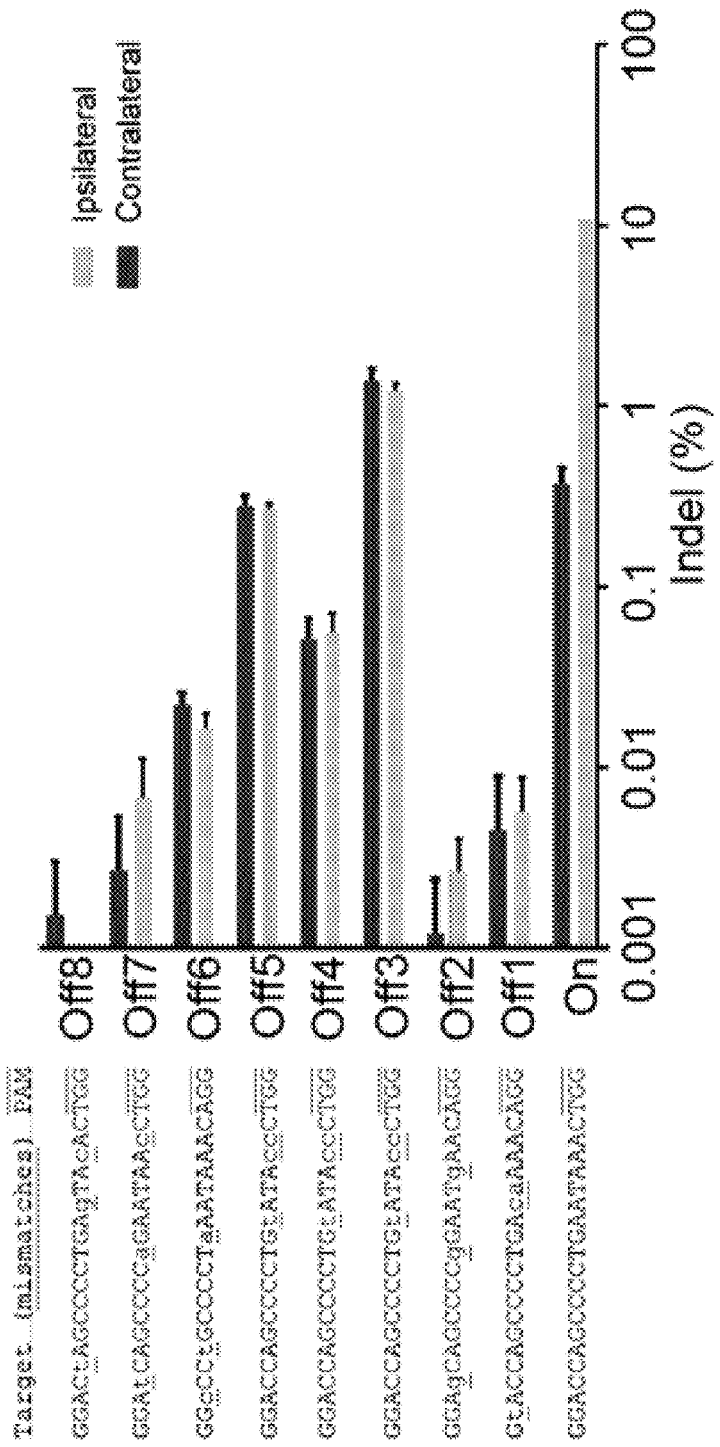
FIG. 13 is a set of results illustrating off-target positions and indel frequencies of PMP22-TATA sgRNA in a mouse genome by an in silico analysis, and (a) illustrates off-target positions and (b) is a graph illustrating an indel frequency at each off-target position. The on-target and Off1-Off8 sequences of FIGS. 13A and 13B are represented by SEQ ID NOs: 216 and 244-251.

In order to confirm whether the off-target mutation occurred in the sciatic nerve by PMP22-TATA RNP, an in silico-based off-target analysis was performed. As a result, eight off-targets including 3 bp or more mismatches were confirmed from the mouse genome (FIG. 13A), and as a result of performing targeted deep sequencing, no indel mutation exceeding the sequencing error ratio was confirmed from the nerve (ipsilateral) treated with PMP22-TATA RNP (FIG. 13B).

Figure 14A:
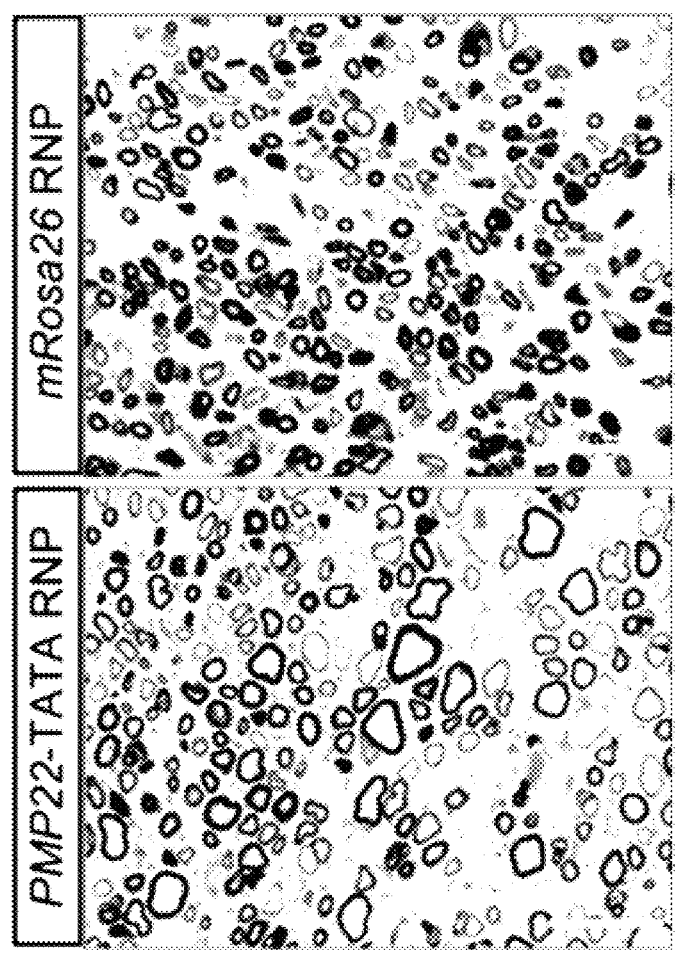
FIG. 14 is a set of results illustrating the alleviation of a disease phenotype through expression inhibition of PMP22 by CRISPR/Cas9 in CMT1A mice, and (a) is a set of images of a semithin section of the sciatic nerve tissue treated with mRosa26 or a PMP22-TATA RNP complex, and the upper graph and the low graph in (b) are a scatter plot illustrating that the g-ratio is increased in mice treated with PMP22-TATA RNP and a graph illustrating that the diameter of the myelinated axon is increased in mice treated with MP22-TATA RNP, respectively.
Figure 14B:
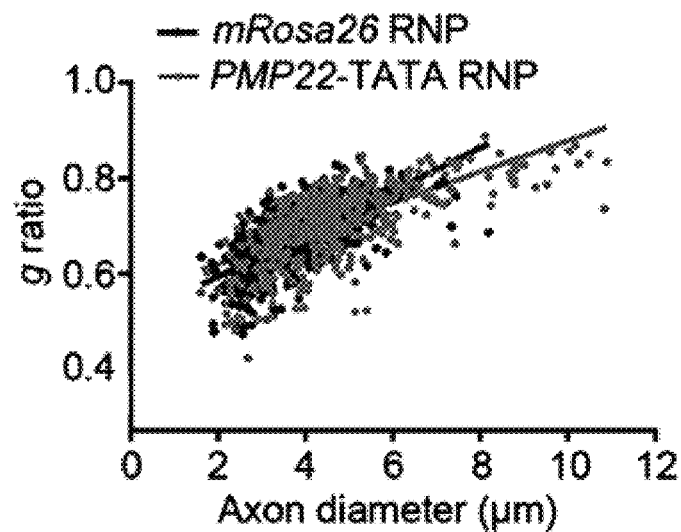
Figure 14B:
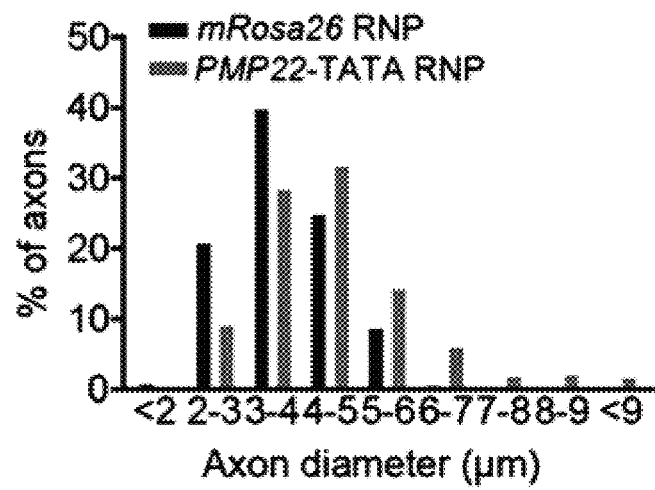

In order to test whether a decrease in transcription of PMP22 caused by PMP22-TATA RNA could prevent demyelination, the sciatic nerve of the C22 mouse treated with PMP22-TATA RNP or mRosa26 RNP was obtained, and the semi-thin cross sections thereof were stained with toluidine-blue (myelin staining). Furthermore, in order to measure the g-ratio, the axon diameter and the fiber (axon including myelin) diameter were measured. As a result, it could be confirmed that a thicker myelin sheet was formed in an experimental group treated with PMP22-TATA RNP (FIG. 14A, FIG. 14B). In addition, when the experimental group was treated with PMP22-TATA RNP, as compared to a control treated with mRosa26 RNP, it was found that the number of axons having a large diameter was increased (FIG. 14A, FIG. 14B). A result of measuring the number of large myelinated fibers having a diameter of 6 μm or more in an experimental group (16.5%) treated with PMP22-TATA RNP exhibits a clearer therapeutic effect than that in the control (2.6%, p<0.01).

Figure 15:
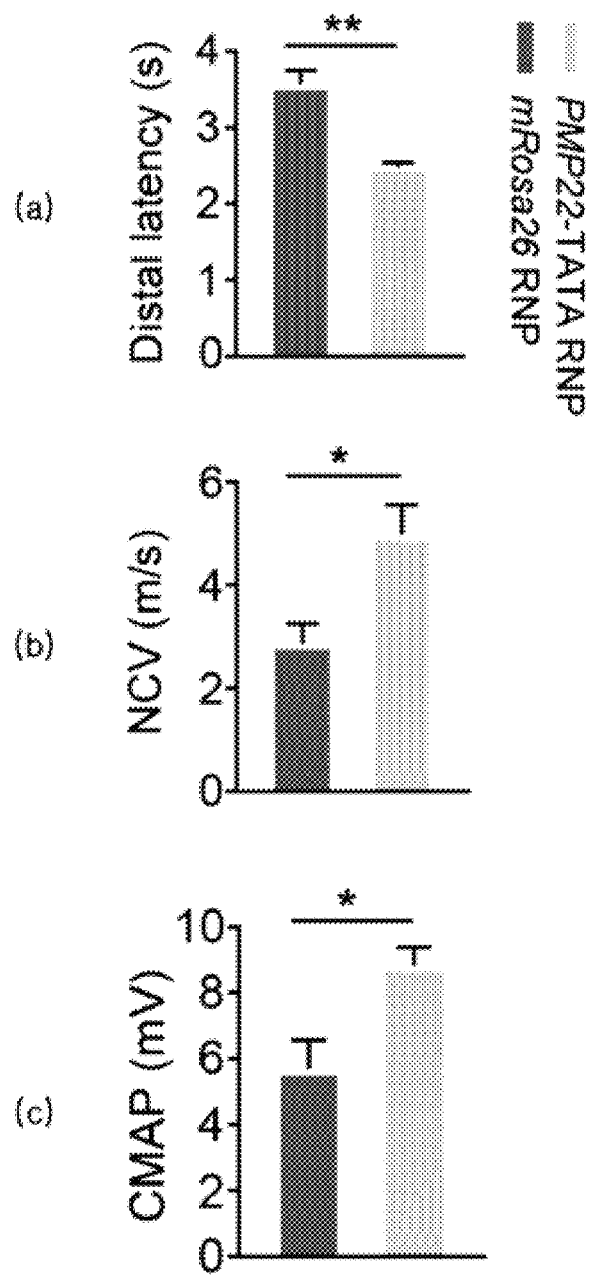
FIG. 15 is a set of results illustrating electrophysiological changes through expression inhibition of PMP22 by CRISPR/Cas9 in CMT1A mice, and (a) is a graph illustrating the change in distal latency (DL), (b) is a graph illustrating the change in motor nerve conduction velocity (NCV), and (c) is a graph illustrating the change in compound muscle action potential (CMAP) (n=7 for mRosa26 RNP; n=10 for PMP22-TATA).

In consideration of a considerable improvement in myelination histological analysis, electrophysiological profiles of the two groups were investigated. As a result, it was confirmed that the distal latency (DL) was decreased and the motor nerve conduction velocity (NCV) was increased in the sciatic nerve of the experimental group treated with PMP22-TATA RNP as compared to a control treated with mRosa26 RNP (FIG. 15A, FIG. 15B), and the results correspond to the increases in myelin thickness and axon diameter in the nerve treated with PMP22-TATA RNP. Further, it was confirmed that the amplitude of the compound muscle action potential (CMAP) was considerably increased in the nerve treated with PMP22-TATA RNP (FIG. 15C), which corresponds to the previous result.

Figure 16A:
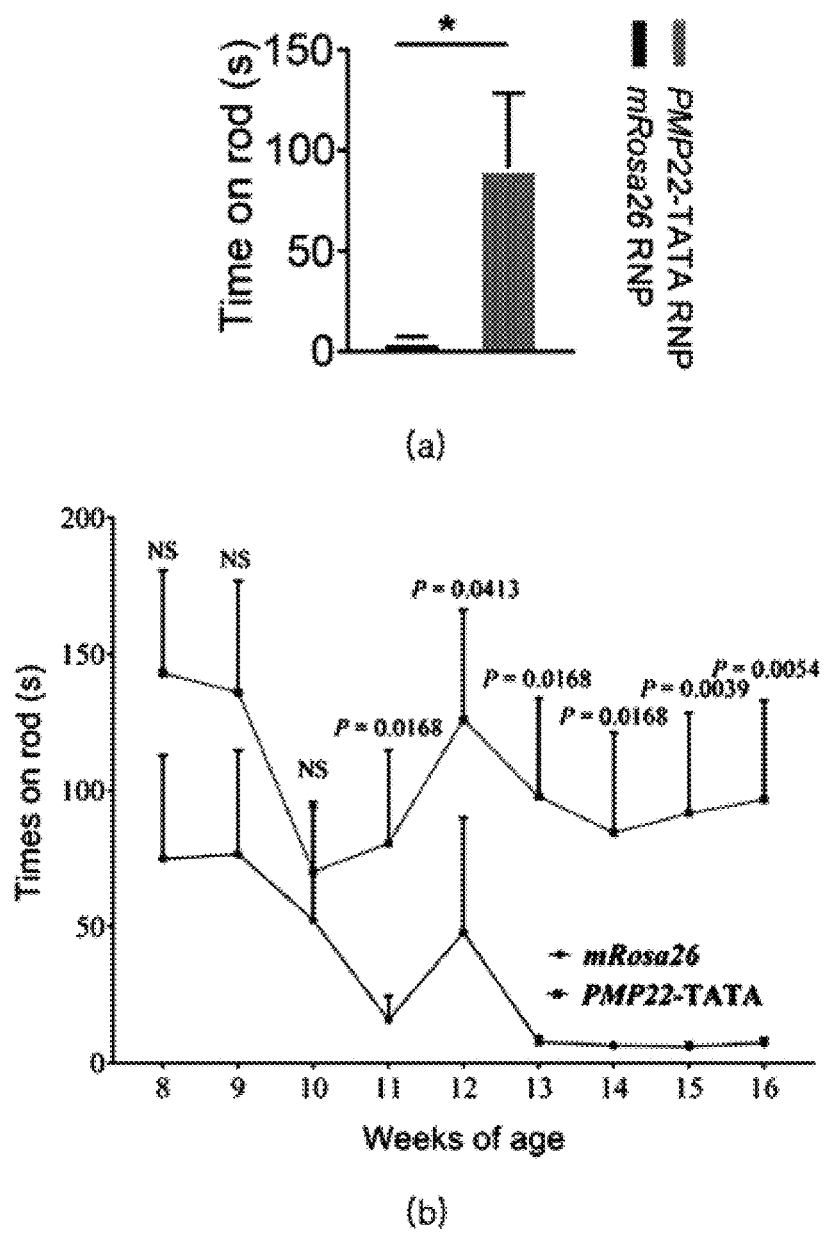
FIG. 16 is a set of analysis results of locomotor behavior due to the expression inhibition of PMP22 by CRISPR/Cas9 in CMT1A mice, and the upper graph and the lower graph in (a) are a rotarod test result (n=7 for mRosa26 RNP, n=11 for PMP22-TATA) and a rotarod test result measured weekly until the mice became 8 weeks old to 16 weeks old (n=7 for mRosa26 RNP, n=11 for PMP22-TATA), respectively, and the upper graph and the lower image in (b) are a graph illustrating the ratio of gastrocnemius muscle weight/body weight of a C22 mouse treated with mRosa26 or a PMP22-TATA RNP complex and a set of gastrocnemius muscle images of a C22 mouse treated with mRosa26 or a PMP22-TATA RNP complex, respectively.
Figure 16B:
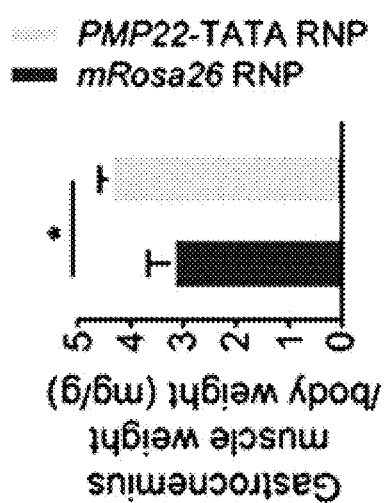
Figure 16B:
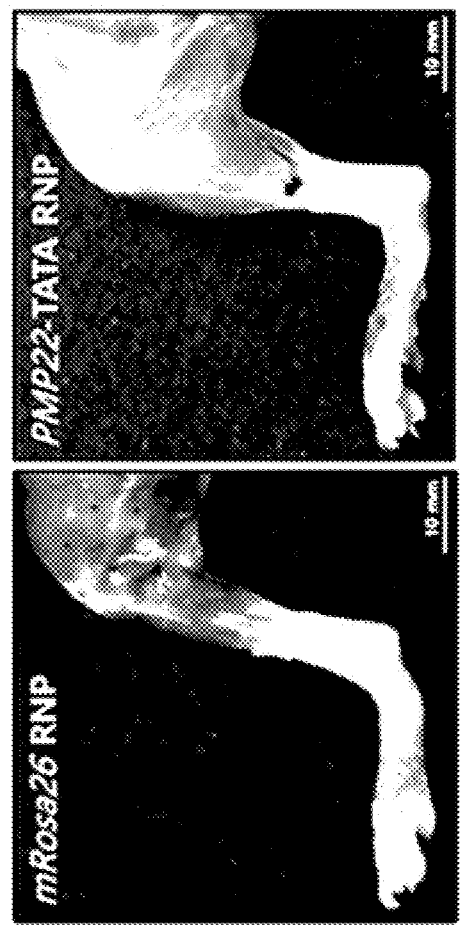

In consideration of the histologically and electrophysiologically improved effects by PMP22-TATA RNP, the locomotor behavior of mice was analyzed by a rotarod experiment. As a result, it was confirmed that mice (11 to 16 week old) treated with PMP22-TATA RNP remained longer on the rod than mice (11 to 16 week old) treated with mRosa26 RNP (FIG. 16A). Further, it was confirmed that mice treated with MP22-TATA RNP were increased in muscle as compared to mice treated with mRosa26 RNP (FIG. 16B).

These results show a therapeutic effect of PMP22-TATA RNP for alleviating or treating demyelination by overexpression of PMP22, such as CMT1A.

Accordingly, the aforementioned results show the expression inhibition effect of PMP22 using CRISPR/Cas9 targeting the promoter site of PMP22. Furthermore, the results show that a direct non-viral delivery of PMP22-TATA RNP to the sciatic nerve of the C22 mouse may improve the clinical and neuropathological phenotypes associated with the demyelination caused by the overexpression of PMP22. Therefore, it is believed that the CRISPR/Cas9-mediated modification of the controlling-factor site of PMP22 may be a good strategy for the treatment of CMT1A and other diseases that exhibit demyelinating neuropathies.

INDUSTRIAL APPLICABILITY

An artificially manipulated SC function-controlling factor and an SC function-controlling system whose functions are artificially modified by the same may be used for effective treatment of an SC dysfunction disorder, for example, an SC function-controlling factor associated disease such as Charcot-Marie-Tooth disease type 1A (CMT1A), Dejerine-Sottas disease (DSS), Congenital Hypomyelination Neuropathy (CHN), or Roussy-Levy syndrome (RLS). Through various in vivo mechanisms that SC function-controlling factors are involved in, the efficacy of an SC function-controlling system may be improved.

What is claimed is:

1. A composition for editing a PMP22 gene in a cell, comprising:
   a Cas9 protein derived from *Streptococcus pyogenes* or a nucleic acid encoding the Cas9 protein; and
   a guide RNA comprising a crRNA and a tracrRNA or a nucleic acid encoding the guide RNA,
   wherein the guide RNA targets a sequence of SEQ ID NOs: 14 to 17, which is a TATA-box site of a human PMP22 gene.

2. The composition of claim 1, wherein the guide RNA is in the form of chimeric single stranded RNA (sgRNA).

3. The composition according to claim 2, wherein the composition comprises the Cas9 protein and the guide RNA, in which the Cas9 protein are complexed with the guide RNA as a form of ribonucleoprotein (RNP).

4. The composition according to claim 2, wherein the composition is in the form of one or more vectors.

5. The composition according to claim 4, wherein the vector is a viral or non-viral vector, wherein the non-viral vector is plasmids, and wherein the viral vector is selected from a group consisting of a retrovirus, a lentivirus, an adenovirus, adeno-associated virus (AAV), vaccinia virus, a poxvirus and a herpes simplex virus.

* * * * *